United States Patent
Song

(10) Patent No.: US 10,066,019 B2
(45) Date of Patent: Sep. 4, 2018

(54) OPTIMISED HEAVY CHAIN AND LIGHT CHAIN SIGNAL PEPTIDES FOR THE PRODUCTION OF RECOMBINANT ANTIBODY THERAPEUTICS

(71) Applicant: Agency for Science, Technology and Research, Singapore (SG)

(72) Inventor: Zhiwei Song, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/435,094

(22) PCT Filed: Aug. 21, 2013

(86) PCT No.: PCT/SG2013/000360
§ 371 (c)(1),
(2) Date: Apr. 10, 2015

(87) PCT Pub. No.: WO2014/058389
PCT Pub. Date: Apr. 17, 2014

(65) Prior Publication Data
US 2015/0225482 A1      Aug. 13, 2015

(30) Foreign Application Priority Data
Oct. 12, 2012   (SG) .................................. 201207629

(51) Int. Cl.
| C07K 16/22 | (2006.01) |
| C07K 16/32 | (2006.01) |
| C07K 16/28 | (2006.01) |
| C12N 15/63 | (2006.01) |
| C07K 16/24 | (2006.01) |
| C07K 16/30 | (2006.01) |

(52) U.S. Cl.
CPC .......... *C07K 16/2887* (2013.01); *C07K 16/22* (2013.01); *C07K 16/241* (2013.01); *C07K 16/2863* (2013.01); *C07K 16/3015* (2013.01); *C07K 16/3061* (2013.01); *C07K 16/32* (2013.01); *C12N 15/635* (2013.01); *C07K 2317/24* (2013.01); *C07K 2319/02* (2013.01)

(58) Field of Classification Search
CPC .... C07K 16/22; C07K 16/2863; C07K 16/32; C07K 2317/24; C07K 2319/02
USPC ......... 424/113.1, 178.1; 530/387.3; 536/23.4
See application file for complete search history.

(56) References Cited

U.S. PATENT DOCUMENTS

| 5,506,132 A | 4/1996 | Lake et al. |
| 2009/0208491 A1 | 8/2009 | Gurney et al. |

FOREIGN PATENT DOCUMENTS

| WO | WO-2003/085089 | 10/2003 |
| WO | WO-2004/031362 | 4/2004 |
| WO | WO-2005/017107 | 2/2005 |
| WO | WO-2007/045465 | 4/2007 |
| WO | WO-2010/108153 | 9/2010 |
| WO | WO-2011/053699 | 5/2011 |
| WO | WO-2014/058389 | 4/2014 |

OTHER PUBLICATIONS

Compound | definition of compound by on-line Medical dictionary (pp. 1-7; Dec. 29, 2017).*
"International Application No. PCT/SG2013/000360, International Search Report and Written Opinion dated Nov. 1, 2013", (dated Nov. 1, 2013), 12 pgs.
Klatt, Stephan, et al., "Secretory signal peptide modification for optimized antibody-fragment expression-secretion in Leishmania tarentolae", Microbial Cell Factories 2012, 11:97, Jul. 25, 2012, (Jul. 25, 2012), 10 pgs.
"European Application No. 13845618.1, Extended European Search Report dated Mar. 31, 2016", (dated Mar. 31, 2016), 14 pgs.
Haryadi, Ryan, et al., "Optimization of Heavy Chain and Ligh Chain Signal Peptides for High Level Expression of Therapeutic Antibodies in CHO Cells", PLoS ONE 10(2):e0116878, (Feb. 23, 2015), 16 pgs.
Ho, Steven C.L., et al., "Comparison of Internal Ribosome Entry Site (IRES) and Furin-2A (F2A) for Monoclonal Antibody Expression Level and Quality in CHO Cells", PLoS ONE 8(5):e63247, (May 21, 2013), 12 pgs.

* cited by examiner

*Primary Examiner* — Lynn A Bristol
(74) *Attorney, Agent, or Firm* — Schwegman Lundberg & Woessner, P.A.

(57) ABSTRACT

Antibodies of interest comprising a heavy chain signal peptide and/or a light chain signal peptide or combination thereof and compositions are described. The method of determining the signal peptide including creating data set of antibodies signal peptides, clustering, selecting and creating recombinant antibodies for enhanced expression and secretion are described.

16 Claims, 24 Drawing Sheets
Specification includes a Sequence Listing.

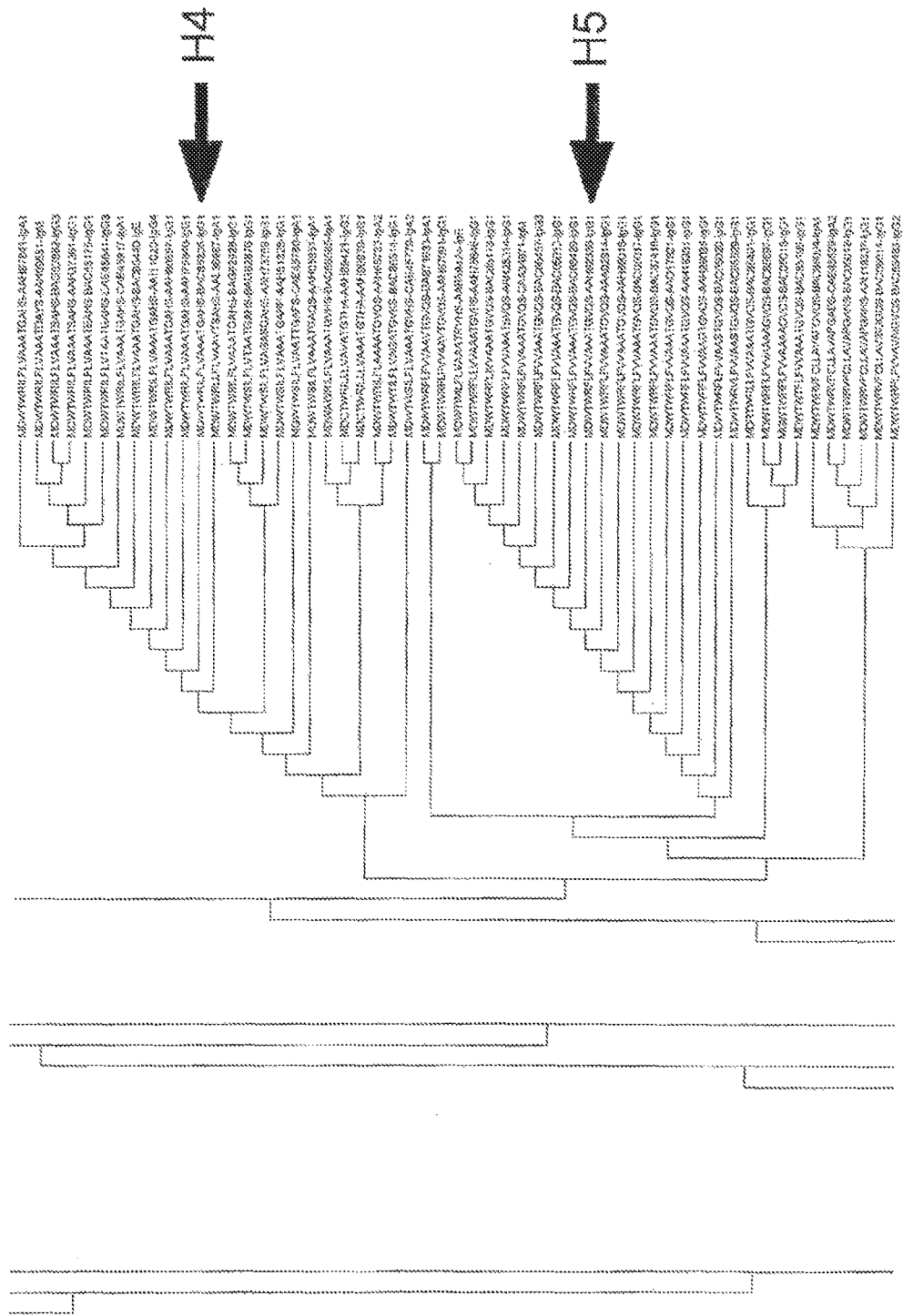

| Heavy chain | SEQ ID NO: | Amino acid sequence | SEQ ID NO: | Corresponding nucleotide sequence |
|---|---|---|---|---|
| H1 | 5 | MELGLSWIFLLAILKGVQC | 283 | ATGGAGTTGGGACTGAGCTGGATTTTCCTTTGGCTATTTTAA AAGGTGTCCAGTGT |
| H2 | 6 | MELGLRWVFLVAILEGVQC | 284 | ATGGAACTGGGGCTCCGCTGGGTTTTCCTTGTTGCTATTTAG AAGGTGTCCAGTGT |
| H3 | 7 | MKHLWFFLLLVAAPRWVLS | 285 | ATGAAACACCTGTGGTTCTTCCTCCTGCTGGTGGCAGCTCCA GATGGGTCTGTGTCC |
| H4 | 8 | MDWTWRILFLVYAAATGAHS | 286 | ATGGACTGGACCTGGAGGATCCTCTTCTTGGTGGCAGCAGCA ACAGGTGCCACTCG |
| H5 | 1 | MDWTWRFLFVVAAATGVQS | 287 | ATGGAGTTGGGCTGAGCTGGCTTTTCTTGTGGCTTTTCTAA AAGGTGTCCAGTGT |
| H6 | 9 | MEFGLSWLFLVAILKGVQC | 288 | ATGGAGTTTGGCTGAGCTGGCTTTTCTTGTGGCTTTTCTAA AAGGTGTCCAGTGT |
| H7 | 3 | MEFGLSWVFLVALFRGVQC | 289 | ATGGAGTTTGGGCTGAGCTGGGTTTTCCTCGTCTCTTTTA GAGGTGTCCAGTGT |
| H8 | 10 | MDLLHKNMKHLWFLLLVAAPRWVLS | 290 | ATGGACCTCCTGCACAAGAACATGAAACACCTGGTTCTTC CTCCTCCTGGTGGCAGCTCCCAGATGGGTGTCC |

| Light chain | SEQ ID NO: | Amino acid sequence | SEQ ID NO: | Corresponding nucleotide sequence |
|---|---|---|---|---|
| L1 | 2 | MDMRVPAQLLGLLLLWLSGARC | 291 | ATGGACATGAGGGTCCCTGCTCAGCTCCTGGGGCTCCTGCTG CTCTGGCTCTCAGGTGCCAGATGT |
| L2 | 4 | MKYLLPTAAAGLLLLAAQPAMA | 292 | ATGAAATACCTATTGCCTACGGCAGCCGCTGGATTGTATTAC TGCCGCGCCCAGCCATGGCC |

```
             1         10         19
             |---------+---------|
H7           MEFGLSWYFLVALFRGVQC
H1           MELGLSWIFLLAILKGVQC
H6           MEFGLSWLFLVAILKGVQC
H2           MELGLRWYFLVAILEGVQC
H3           MKHLWFFLLLVAAPRWVLS
H8   MDLLHKNMKHLWFFLLLVAAPRWVLS
H4           MDWTHRILFLVAAATGAHS
H5           MDWTHRFLFVVAAATGVQS
Consensus  ..M...w..lflvAa..gvqs
```

```
  1      6 7       14 15   19
  |------|  |-------|  |----|
  N-domain   H-domain   C-domain
```

B

```
H7 :  MEFGLS WVFLVALF RGVQC
H7a:  MEFGWS WVFLVALF RGVQC
H7b:  MEFGLS WLFLVALF RGVQC
H7c:  MEFGLS WVFLVAAF RGVQC
H7d:  MEFGLS WVFLVALF RGVQS
H7e:  MEFGWS WLFLVAAF RGVQC
H7f:  MEFGWS WLFLVAAF RGVQS
```

FIG. 10-1

Herceptin heavy chain:
M------------CEVQLVESGGGLVQPGGSLRLSCAASGFNIKDTYIHWVRQAPGKGLE......

Herceptin light chain:
M------------CDIQMTQSPSSLSASVGDRVTITCRASQDVNTAVAWYQQKPGKA......

SEQUENCE LISTING

```
<160> NUMBER OF SEQ ID NOS: 331

<210> SEQ ID NO 1
<211> LENGTH: 19
<212> TYPE: PRT
<213> ORGANISM: Homo sapiens

<400> SEQUENCE: 1

Met Asp Trp Thr Trp Arg Phe Leu Phe Val Val Ala Ala Ala Thr Gly
1               5                   10                  15

Val Gln Ser

<210> SEQ ID NO 2
<211> LENGTH: 22
<212> TYPE: PRT
<213> ORGANISM: Homo sapiens

<400> SEQUENCE: 2
```

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 3
<211> LENGTH: 19
<212> TYPE: PRT
<213> ORGANISM: Homo sapiens

<400> SEQUENCE: 3

Met Glu Phe Gly Leu Ser Trp Val Phe Leu Val Ala Leu Phe Arg Gly
1               5                   10                  15

Val Gln Cys

<210> SEQ ID NO 4
<211> LENGTH: 22
<212> TYPE: PRT
<213> ORGANISM: Homo sapiens

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 5
<211> LENGTH: 19
<212> TYPE: PRT
<213> ORGANISM: Homo sapiens

<400> SEQUENCE: 5

Met Glu Leu Gly Leu Ser Trp Ile Phe Leu Leu Ala Ile Leu Lys Gly
1               5                   10                  15

Val Gln Cys

<210> SEQ ID NO 6
<211> LENGTH: 19
<212> TYPE: PRT
<213> ORGANISM: Homo sapiens

<400> SEQUENCE: 6

Met Glu Leu Gly Leu Arg Trp Val Phe Leu Val Ala Ile Leu Glu Gly
1               5                   10                  15

Val Gln Cys

<210> SEQ ID NO 7
<211> LENGTH: 19
<212> TYPE: PRT
<213> ORGANISM: Homo sapiens

<400> SEQUENCE: 7

Met Lys His Leu Trp Phe Phe Leu Leu Leu Val Ala Ala Pro Arg Trp
1               5                   10                  15

Val Leu Ser

<210> SEQ ID NO 8
<211> LENGTH: 19
<212> TYPE: PRT
<213> ORGANISM: Homo sapiens

```
<400> SEQUENCE: 8

Met Asp Trp Thr Trp Arg Ile Leu Phe Leu Val Ala Ala Ala Thr Gly
1               5                   10                  15

Ala His Ser

<210> SEQ ID NO 9
<211> LENGTH: 19
<212> TYPE: PRT
<213> ORGANISM: Homo sapiens

<400> SEQUENCE: 9

Met Glu Phe Gly Leu Ser Trp Leu Phe Leu Val Ala Ile Leu Lys Gly
1               5                   10                  15

Val Gln Cys

<210> SEQ ID NO 10
<211> LENGTH: 26
<212> TYPE: PRT
<213> ORGANISM: Homo sapiens

<400> SEQUENCE: 10

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 11
<211> LENGTH: 450
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
```

```
            195                 200                 205
Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 453
<212> TYPE: PRT
<213> ORGANISM: Homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110
```

Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
        450

<210> SEQ ID NO 13
<211> LENGTH: 450
<212> TYPE: PRT
<213> ORGANISM: Homo sapiens

<400> SEQUENCE: 13

Glu Val Lys Leu Glu Glu Ser Gly Gly Gly Leu Val Gln Pro Gly Gly
1               5                   10                  15
Ser Met Lys Leu Ser Cys Val Ala Ser Gly Phe Ile Phe Ser Asn His
            20                  25                  30

-continued

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
 50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
             100                 105                 110

Gly Thr Thr Leu Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
     210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Lys
    450

<210> SEQ ID NO 14
<211> LENGTH: 451
<212> TYPE: PRT
<213> ORGANISM: Homo sapiens

<400> SEQUENCE: 14

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 15
<211> LENGTH: 451
<212> TYPE: PRT
<213> ORGANISM: Homo sapiens

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 16
<211> LENGTH: 214
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 17
<211> LENGTH: 214
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 214
<212> TYPE: PRT
<213> ORGANISM: Homo sapiens

<400> SEQUENCE: 18

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80
```

-continued

```
Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 213
<212> TYPE: PRT
<213> ORGANISM: Homo sapiens

<400> SEQUENCE: 19

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 20

```
<211> LENGTH: 214
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 1353
<212> TYPE: DNA
<213> ORGANISM: Homo sapiens

<400> SEQUENCE: 21
gaggttcagc tggtggagtc tggcggtggc ctggtgcagc cggggggctc tctccgtttg    60
tcctgtgcag cttctggctt caacattaaa gacacctata tccactgggt gcgtcaggct   120
ccgggtaagg gcctggagtg ggttgcaagg atttatccta cgaatggtta tactcgttat   180
gccgatagcg tcaagggccg tttcactata agcgcagaca cttcgaaaaa cacagcctac   240
ctccagatga acagcctgcg tgctgaggac actgccgtct attattgtag cagatggggt   300
ggggacggct ctatgctat ggactactgg ggtcaaggta cactagtcac cgtcagcagc   360
gctagcacca agggcccatc ggtcttcccc ctggcaccct cctccaagag cacctctggg   420
ggcacagcgg ccctgggctg cctggtcaag gactacttcc ccgaaccggt gacggtgtca   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggga   720
```

```
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

<210> SEQ ID NO 22
<211> LENGTH: 1362
<212> TYPE: DNA
<213> ORGANISM: Homo sapiens

<400> SEQUENCE: 22

```
gaggttcagc tggtggagtc tggcggtggc ctggtgcagc caggggctc actccgtttg      60 tcctgtgcag cttctggcta cacctttacc aactacggca tgaactgggt gcgtcaggcc    120
ccaggtaagg gcctggaatg ggttgggtgg ataaacacct acactggaga gccaacatat    180
gctgctgact tcaagagacg gtttaccttc tctttggaca cctctaagag cacagcctac    240
ctgcaaatga acagcctgcg tgctgaggac actgccgtct attattgtgc taaatacccc    300
cactactacg gctctagcca ctggtatttt gacgtctggg gtcaaggaac cctggtcacc    360
gtctcctcgg ctagcaccaa gggcccatcg gtcttccccc tggcaccctc ctccaagagc    420
acctctgggg gcacagcggc cctgggctgc ctggtcaagg actacttccc cgaaccggtg    480
acggtgtcat ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca aatcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagcccga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat ga                      1362
```

<210> SEQ ID NO 23

<211> LENGTH: 1353
<212> TYPE: DNA
<213> ORGANISM: Homo sapiens

<400> SEQUENCE: 23

```
gaagtgaagc ttgaggagtc tggaggaggc ttggtgcaac ctggaggatc catgaaactc      60
tcctgtgttg cctctggatt catttttcagt aaccactgga tgaactgggt ccgccagtct     120
ccagagaagg ggcttgagtg ggttgctgaa attagatcaa aatctattaa ttctgcaaca     180
cattatgcgg agtctgtgaa agggaggttc accatctcaa gagatgattc caaaagtgct     240
gtctacctgc aaatgaccga cttaagaact gaagacactg gcgttttatta ctgttccagg     300 aattactacg gtagtaccta cgactactgg ggccaaggca ccactctcac agtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag cgccctgac cagcggcgtg cacaccttcc cggctgtcct acagtcctca     540
ggactctact ccctcagcag cgtggtgacc gtgcctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720 ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                  1353
```

<210> SEQ ID NO 24
<211> LENGTH: 1356
<212> TYPE: DNA
<213> ORGANISM: Homo sapiens

<400> SEQUENCE: 24

```
caggtacaac tgcagcagcc tgggggctgag ctggtgaagc ctggggcctc agtgaagatg      60
tcctgcaagg cttctggcta cacatttacc agttacaata tgcactgggt aaaacagaca     120
cctggtcggg gcctggaatg gattggagct atttatcccg gaaatggtga tacttcctac     180
aatcagaagt tcaaaggcaa ggccacattg actgcagaca aatcctccag cacagcctac     240
atgcagctca gcagcctgac atctgaggac tctgcggtct attactgtgc aagatcgact     300
tactacggcg gtgactggta cttcaatgtc tggggcgcag ggaccacggt caccgtctct     360
gcagctagca ccaagggccc atcggtcttc ccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
```

| | |
|---|---|
| acctacatct gcaacgtgaa tcacaagccc agcaacacca aggtggacaa gaaagcagag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaatga | 1356 |

<210> SEQ ID NO 25
<211> LENGTH: 1356
<212> TYPE: DNA
<213> ORGANISM: Homo sapiens

<400> SEQUENCE: 25

| | |
|---|---|
| gaggtgcagc tggtggagtc tgggggaggc ttggtacagc ccggcaggtc cctgagactc | 60 |
| tcctgtgcgg cctctggatt cacctttgat gattatgcca tgcactgggt ccggcaagct | 120 |
| ccagggaagg gcctgaatg gtctcagct atcacttgga atagtggtca catagactat | 180 |
| gcggactctg tggagggccg attcaccatc tccagagaca cgccaagaa ctccctgtat | 240 |
| ctgcaaatga acagtctgag agctgaggat acggccgtat attactgtgc gaaagtctcg | 300 |
| taccttagca ccgcgtcctc ccttgactat tggggccaag gtaccctggt caccgtctcg | 360 |
| agtgctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcatggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |

```
acgcagaaga gcctctccct gtctccgggt aaatga                              1356
```

<210> SEQ ID NO 26
<211> LENGTH: 645
<212> TYPE: DNA
<213> ORGANISM: Homo sapiens

<400> SEQUENCE: 26

```
gatatccaga tgacccagtc cccgagctcc ctgtccgcct ctgtgggcga tagggtcact     60
atcacctgcc gtgccagtca ggatgtgaat actgctgtag cctggtatca acagaaaccc   120
ggaaaggccc cgaaactgct gatttactcg gcatccttcc tctactctgg agtcccttct   180
cgcttctctg gttcccgctc tgggacggat ttcactctga ccatcagctc cctgcagccg   240
gaagacttcg caacttatta ctgtcagcaa cactatacta ctcctccgac gttcggacag   300
ggtaccaagg tggagatcaa acgtaccgtg gcggcgccat ctgtcttcat cttcccgcca   360
tctgatgagc agttgaaatc tggaactgcc tctgttgtgt gcctgctgaa taacttctat   420
cccagagagg ccaaagtaca gtggaaggtg ataacgccc  tccaatcggg taactcccag   480
gagagtgtca cagagcagga cagcaaggac agcacctaca gcctcagcag cacccctgacg  540
ctgagcaaag cagactacga aaacacaaa gtctacgcct gcgaagtcac ccatcagggc   600
ctgagctcgc ccgtcacaaa gagcttcaac aggggagagt gttag                   645
```

<210> SEQ ID NO 27
<211> LENGTH: 645
<212> TYPE: DNA
<213> ORGANISM: Homo sapiens

<400> SEQUENCE: 27

```
gatatccaga tgacccagtc cccgagctcc ctgtccgcct ctgtgggcga tagggtcacc     60
atcacctgtt ccgccagtca ggacatctct aattatctca actggtatca acagaaacca   120
ggaaaagctc cgaaagtgct gatttacttt acctcctccc tgcactctgg agtcccttct   180
cgcttctctg gttctggttc tgggacggat ttcactctga ccatcagcag tctgcaaccg   240
gaggacttcg caacttatta ctgtcagcaa tattctactg tgccgtggac gttcggacag   300
ggtaccaagg tggagatcaa acgtaccgtg gcggcgccat ctgtcttcat cttcccgcca   360
tctgatgagc agttgaaatc tggaactgcc tctgttgtgt gcctgctgaa taacttctat   420
cccagagagg ccaaagtaca gtggaaggtg ataacgccc  tccaatcggg taactcccag   480
gagagtgtca cagagcagga cagcaaggac agcacctaca gcctcagcag cacccctgacg  540
ctgagcaaag cagactacga aaacacaaa gtctacgcct gcgaagtcac ccatcagggc   600
ctgagctcgc ccgtcacaaa gagcttcaac aggggagagt gttag                   645
```

<210> SEQ ID NO 28
<211> LENGTH: 645
<212> TYPE: DNA
<213> ORGANISM: Homo sapiens

<400> SEQUENCE: 28

```
gacatcttgc tgactcagtc tccagccatc ctgtctgtga gtccaggaga aagagtcagt     60
ttctcctgca gggccagtca gttcgttggc tcaagcatcc actggtatca gcaagaaca    120
aatggttctc caaggcttct cataaagtat gcttctgagt ctatgtctgg gatcccttcc   180
aggtttagtg gcagtggatc aggacagat tttactctta gcatcaacac tgtggagtct    240
gaagatattg cagattatta ctgtcaacaa agtcatagct ggccattcac gttcggctcg   300
```

```
gggacaaatt tggaagtaaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttga                    645

<210> SEQ ID NO 29
<211> LENGTH: 642
<212> TYPE: DNA
<213> ORGANISM: Homo sapiens

<400> SEQUENCE: 29
caaattgttc tctcccagtc tccagcaatc ctgtctgcat ctccagggga aaggtcaca     60 atgacttgca gggccagctc aagtgtaagt tacatccact ggttccagca gaagccagga    120
tcctccccca aaccctggat ttatgccaca tccaacctgg cttctggagt ccctgttcgc    180
ttcagtggca gtgggtctgg gacttcttac tctctcacaa tcagcagagt ggaggctgaa    240
gatgctgcca cttattactg ccagcagtgg actagtaacc cacccacgtt cggaggggggg   300 accaagctgg aaatcaaacg tacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ga                       642

<210> SEQ ID NO 30
<211> LENGTH: 645
<212> TYPE: DNA
<213> ORGANISM: Homo sapiens

<400> SEQUENCE: 30
gacatccaga tgacccagtc tccatcctcc ctgtctgcat ctgtagggga cagagtcacc    60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa acgtaccgtg gcggcgccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 31
<211> LENGTH: 36
<212> TYPE: DNA
<213> ORGANISM: Homo sapiens
```

<400> SEQUENCE: 31
ccaccatgga gtttgggtgg agctgggttt tcctcg                                    36

<210> SEQ ID NO 32
<211> LENGTH: 36
<212> TYPE: DNA
<213> ORGANISM: Homo sapiens

<400> SEQUENCE: 32
cgaggaaaac ccagctccac ccaaactcca tggtgg                                    36

<210> SEQ ID NO 33
<211> LENGTH: 39
<212> TYPE: DNA
<213> ORGANISM: Homo sapiens

<400> SEQUENCE: 33
gagtttgggc tgagctggct cttcctcgtt gctcttttt                                 39

<210> SEQ ID NO 34
<211> LENGTH: 39
<212> TYPE: DNA
<213> ORGANISM: Homo sapiens

<400> SEQUENCE: 34
aaaaagagca acgaggaaga gccagctcag cccaaactc                                 39

<210> SEQ ID NO 35
<211> LENGTH: 40
<212> TYPE: DNA
<213> ORGANISM: Homo sapiens

<400> SEQUENCE: 35
ctgggttttc ctcgttgctg cttttagagg tgtccagtgt                                40

<210> SEQ ID NO 36
<211> LENGTH: 40
<212> TYPE: DNA
<213> ORGANISM: Homo sapiens

<400> SEQUENCE: 36
acactggaca cctctaaaag cagcaacgag gaaaacccag                                40

<210> SEQ ID NO 37
<211> LENGTH: 38
<212> TYPE: DNA
<213> ORGANISM: Homo sapiens

<400> SEQUENCE: 37
tttttagagg tgtccagtcc gaggttcagc tggtggag                                  38

<210> SEQ ID NO 38
<211> LENGTH: 38
<212> TYPE: DNA
<213> ORGANISM: Homo sapiens

<400> SEQUENCE: 38
ctccaccagc tgaacctcgg actggacacc tctaaaaa                                  38

<210> SEQ ID NO 39
<211> LENGTH: 48
<212> TYPE: DNA
<213> ORGANISM: Homo sapiens -continued

<400> SEQUENCE: 39
gccaccatgg agtttgggtg gagctggctc ttcctcgttg ctgcttttt                48

<210> SEQ ID NO 40
<211> LENGTH: 48
<212> TYPE: DNA
<213> ORGANISM: Homo sapiens

<400> SEQUENCE: 40
aaaagcagca acgaggaaga gccagctcca cccaaactcc atggtggc                 48

<210> SEQ ID NO 41
<211> LENGTH: 38
<212> TYPE: DNA
<213> ORGANISM: Homo sapiens

<400> SEQUENCE: 41
cttttagagg tgtccagtcc gaggttcagc tggtggag                            38

<210> SEQ ID NO 42
<211> LENGTH: 38
<212> TYPE: DNA
<213> ORGANISM: Homo sapiens

<400> SEQUENCE: 42
ctccaccagc tgaacctcgg actggacacc tctaaaag                            38

<210> SEQ ID NO 43
<211> LENGTH: 19
<212> TYPE: PRT
<213> ORGANISM: Homo sapiens

<400> SEQUENCE: 43

Met Glu Phe Gly Leu Ser Trp Val Phe Leu Val Ala Ile Leu Lys Gly
1               5                   10                  15

Val Gln Cys

<210> SEQ ID NO 44
<211> LENGTH: 19
<212> TYPE: PRT
<213> ORGANISM: Homo sapiens

<400> SEQUENCE: 44

Met Glu Leu Gly Leu Ser Trp Val Phe Leu Val Ala Ile Leu Lys Gly
1               5                   10                  15

Val Gln Cys

<210> SEQ ID NO 45
<211> LENGTH: 19
<212> TYPE: PRT
<213> ORGANISM: Homo sapiens

<400> SEQUENCE: 45

Met Glu Ser Gly Leu Thr Trp Leu Phe Leu Val Ala Ile Leu Lys Gly
1               5                   10                  15

Val His Cys

<210> SEQ ID NO 46
<211> LENGTH: 19
<212> TYPE: PRT
<213> ORGANISM: Homo sapiens

```
<400> SEQUENCE: 46

Met Lys His Leu Trp Phe Phe Leu Leu Leu Val Ala Ala Pro Arg Trp
1               5                   10                  15

Val Leu Ser

<210> SEQ ID NO 47
<211> LENGTH: 19
<212> TYPE: PRT
<213> ORGANISM: Homo sapiens

<400> SEQUENCE: 47

Met Lys His Leu Trp Phe Phe Leu Leu Leu Val Ala Ala Pro Arg Trp
1               5                   10                  15

Val Leu Ser

<210> SEQ ID NO 48
<211> LENGTH: 19
<212> TYPE: PRT
<213> ORGANISM: Homo sapiens

<400> SEQUENCE: 48

Met Asp Trp Thr Trp Arg Ile Leu Phe Leu Val Ala Ala Ala Thr Gly
1               5                   10                  15

Ala His Ser

<210> SEQ ID NO 49
<211> LENGTH: 19
<212> TYPE: PRT
<213> ORGANISM: Homo sapiens

<400> SEQUENCE: 49

Met Glu Leu Gly Leu Arg Trp Val Phe Leu Val Ala Phe Leu Glu Gly
1               5                   10                  15

Val Gln Cys

<210> SEQ ID NO 50
<211> LENGTH: 19
<212> TYPE: PRT
<213> ORGANISM: Homo sapiens

<400> SEQUENCE: 50

Met Asp Trp Thr Trp Arg Ile Leu Phe Leu Val Ala Ala Ala Thr Gly
1               5                   10                  15

Ala His Ser

<210> SEQ ID NO 51
<211> LENGTH: 26
<212> TYPE: PRT
<213> ORGANISM: Homo sapiens

<400> SEQUENCE: 51

Met Asp Leu Met Cys Lys Lys Met Lys His Leu Trp Phe Phe Leu Leu
1               5                   10                  15

Leu Val Ala Ala Pro Arg Trp Val Leu Ser
                20                  25

<210> SEQ ID NO 52
<211> LENGTH: 19
<212> TYPE: PRT
<213> ORGANISM: Homo sapiens
```

```
<400> SEQUENCE: 52

Met Glu Leu Gly Leu Tyr Trp Val Phe Leu Val Ala Ile Leu Glu Gly
1               5                   10                  15

Val Gln Cys

<210> SEQ ID NO 53
<211> LENGTH: 19
<212> TYPE: PRT
<213> ORGANISM: Homo sapiens

<400> SEQUENCE: 53

Met Glu Leu Gly Leu Arg Trp Val Phe Leu Val Thr Phe Phe Trp Gly
1               5                   10                  15

Val Gln Cys

<210> SEQ ID NO 54
<211> LENGTH: 19
<212> TYPE: PRT
<213> ORGANISM: Homo sapiens

<400> SEQUENCE: 54

Met Glu Leu Gly Leu Ser Trp Ile Phe Leu Leu Ala Ile Leu Lys Gly
1               5                   10                  15

Val Gln Cys

<210> SEQ ID NO 55
<211> LENGTH: 19
<212> TYPE: PRT
<213> ORGANISM: Homo sapiens

<400> SEQUENCE: 55

Met Gln Phe Gly Leu Ser Trp Val Phe Leu Val Ala Leu Leu Arg Gly
1               5                   10                  15

Val Gln Cys

<210> SEQ ID NO 56
<211> LENGTH: 19
<212> TYPE: PRT
<213> ORGANISM: Homo sapiens

<400> SEQUENCE: 56

Met Asp Thr Leu Cys Ser Thr Leu Leu Leu Thr Ile Pro Ser Trp
1               5                   10                  15

Val Leu Ser

<210> SEQ ID NO 57
<211> LENGTH: 19
<212> TYPE: PRT
<213> ORGANISM: Homo sapiens

<400> SEQUENCE: 57

Met Glu Ser Gly Leu Ser Trp Val Phe Leu Val Ala Leu Leu Arg Gly
1               5                   10                  15

Val Gln Cys

<210> SEQ ID NO 58
<211> LENGTH: 19
<212> TYPE: PRT
<213> ORGANISM: Homo sapiens
```

```
<400> SEQUENCE: 58

Met Glu Phe Gly Leu Ser Trp Val Phe Leu Val Gly Ile Leu Lys Gly
1               5                   10                  15

Val Gln Cys

<210> SEQ ID NO 59
<211> LENGTH: 19
<212> TYPE: PRT
<213> ORGANISM: Homo sapiens

<400> SEQUENCE: 59

Met Asp Trp Thr Trp Arg Phe Leu Phe Val Val Ala Ala Val Thr Gly
1               5                   10                  15

Val Gln Ser

<210> SEQ ID NO 60
<211> LENGTH: 26
<212> TYPE: PRT
<213> ORGANISM: Homo sapiens

<400> SEQUENCE: 60

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 61
<211> LENGTH: 19
<212> TYPE: PRT
<213> ORGANISM: Homo sapiens

<400> SEQUENCE: 61

Met Glu Leu Gly Leu Ser Trp Ile Phe Leu Leu Ala Ile Leu Lys Gly
1               5                   10                  15

Val Gln Cys

<210> SEQ ID NO 62
<211> LENGTH: 19
<212> TYPE: PRT
<213> ORGANISM: Homo sapiens

<400> SEQUENCE: 62

Met Lys His Leu Trp Phe Phe Leu Leu Leu Val Ala Pro Pro Arg Trp
1               5                   10                  15

Val Leu Ser

<210> SEQ ID NO 63
<211> LENGTH: 19
<212> TYPE: PRT
<213> ORGANISM: Homo sapiens

<400> SEQUENCE: 63

Met Glu Phe Gly Leu Ser Trp Val Phe Leu Val Ala Ile Leu Lys Gly
1               5                   10                  15

Val Gln Cys

<210> SEQ ID NO 64
<211> LENGTH: 19
<212> TYPE: PRT
<213> ORGANISM: Homo sapiens
```

<400> SEQUENCE: 64

Met Glu Leu Ser Leu Ser Trp Phe Phe Leu Leu Thr Ile Ile Gln Gly
1               5                   10                  15

Val Gln Cys

<210> SEQ ID NO 65
<211> LENGTH: 26
<212> TYPE: PRT
<213> ORGANISM: Homo sapiens

<400> SEQUENCE: 65

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 66
<211> LENGTH: 19
<212> TYPE: PRT
<213> ORGANISM: Homo sapiens

<400> SEQUENCE: 66

Met Lys His Leu Trp Phe Phe Phe Leu Leu Val Ala Ala Pro Arg Ser
1               5                   10                  15

Val Leu Ser

<210> SEQ ID NO 67
<211> LENGTH: 19
<212> TYPE: PRT
<213> ORGANISM: Homo sapiens

<400> SEQUENCE: 67

Met Glu Leu Gly Leu Ser Trp Val Phe Leu Val Ser Leu Leu Ala Gly
1               5                   10                  15

Val Gln Cys

<210> SEQ ID NO 68
<211> LENGTH: 19
<212> TYPE: PRT
<213> ORGANISM: Homo sapiens

<400> SEQUENCE: 68

Met Glu Phe Gly Leu Ser Trp Ile Phe Leu Val Val Ile Ile Lys Gly
1               5                   10                  15

Val Gln Cys

<210> SEQ ID NO 69
<211> LENGTH: 19
<212> TYPE: PRT
<213> ORGANISM: Homo sapiens

<400> SEQUENCE: 69

Met Asp Trp Thr Trp Ser Ile Leu Phe Leu Val Ala Ala Ala Thr Gly
1               5                   10                  15

Ala Gln Ser

<210> SEQ ID NO 70
<211> LENGTH: 19
<212> TYPE: PRT
<213> ORGANISM: Homo sapiens

```
<400> SEQUENCE: 70

Met Asp Trp Thr Trp Arg Leu Leu Phe Leu Val Ala Ala Val Thr Ser
1               5                   10                  15

Ala His Ser

<210> SEQ ID NO 71
<211> LENGTH: 19
<212> TYPE: PRT
<213> ORGANISM: Homo sapiens

<400> SEQUENCE: 71

Met Glu Phe Gly Leu Ser Trp Val Phe Leu Val Ala Leu Leu Arg Gly
1               5                   10                  15

Val Gln Cys

<210> SEQ ID NO 72
<211> LENGTH: 19
<212> TYPE: PRT
<213> ORGANISM: Homo sapiens

<400> SEQUENCE: 72

Met Gly Trp Thr Trp Ser Ile Leu Phe Leu Val Ala Ala Thr Thr Gly
1               5                   10                  15

Ala Pro Ser

<210> SEQ ID NO 73
<211> LENGTH: 19
<212> TYPE: PRT
<213> ORGANISM: Homo sapiens

<400> SEQUENCE: 73

Met Asp Trp Thr Trp Arg Val Phe Cys Leu Leu Ala Val Ala Pro Gly
1               5                   10                  15

Val Gln Ser

<210> SEQ ID NO 74
<211> LENGTH: 26
<212> TYPE: PRT
<213> ORGANISM: Homo sapiens

<400> SEQUENCE: 74

Met Asp Leu Met Cys Lys Lys Met Lys His Leu Trp Phe Phe Leu Leu
1               5                   10                  15

Leu Val Ala Ala Pro Arg Trp Val Leu Ser
                20                  25

<210> SEQ ID NO 75
<211> LENGTH: 19
<212> TYPE: PRT
<213> ORGANISM: Homo sapiens

<400> SEQUENCE: 75

Met Asp Trp Thr Trp Arg Ile Leu Phe Leu Ala Ala Ala Ala Thr Gly
1               5                   10                  15

Val Gln Ser

<210> SEQ ID NO 76
<211> LENGTH: 19
<212> TYPE: PRT
<213> ORGANISM: Homo sapiens
```

-continued

```
<400> SEQUENCE: 76

Met Lys His Leu Trp Phe Phe Leu Leu Leu Val Ala Ala Pro Arg Trp
1               5                   10                  15

Val Leu Ser

<210> SEQ ID NO 77
<211> LENGTH: 19
<212> TYPE: PRT
<213> ORGANISM: Homo sapiens

<400> SEQUENCE: 77

Met Glu Leu Gly Leu Ser Trp Val Phe Leu Val Ala Ile Leu Glu Gly
1               5                   10                  15

Val His Cys

<210> SEQ ID NO 78
<211> LENGTH: 26
<212> TYPE: PRT
<213> ORGANISM: Homo sapiens

<400> SEQUENCE: 78

Met Asp Leu Met Cys Lys Lys Met Lys His Leu Trp Phe Phe Leu Leu
1               5                   10                  15

Leu Val Ala Ala Pro Gly Trp Val Leu Ser
            20                  25

<210> SEQ ID NO 79
<211> LENGTH: 19
<212> TYPE: PRT
<213> ORGANISM: Homo sapiens

<400> SEQUENCE: 79

Met Glu Leu Gly Leu Cys Trp Val Phe Leu Val Ala Ile Leu Glu Gly
1               5                   10                  15

Val Pro Cys

<210> SEQ ID NO 80
<211> LENGTH: 19
<212> TYPE: PRT
<213> ORGANISM: Homo sapiens

<400> SEQUENCE: 80

Met Glu Leu Gly Leu Ser Trp Val Phe Leu Val Ala Ile Leu Glu Gly
1               5                   10                  15

Val Gln Cys

<210> SEQ ID NO 81
<211> LENGTH: 19
<212> TYPE: PRT
<213> ORGANISM: Homo sapiens

<400> SEQUENCE: 81

Met Lys His Leu Trp Phe Phe Leu Leu Leu Val Ala Ala Pro Arg Trp
1               5                   10                  15

Val Leu Ser

<210> SEQ ID NO 82
<211> LENGTH: 19
<212> TYPE: PRT
<213> ORGANISM: Homo sapiens
```

-continued

<400> SEQUENCE: 82

Met Asp Trp Thr Trp Arg Val Phe Cys Leu Leu Ala Val Ala Pro Gly
1               5                   10                  15

Ala Asp Ser

<210> SEQ ID NO 83
<211> LENGTH: 684
<212> TYPE: PRT
<213> ORGANISM: Homo sapiens

<400> SEQUENCE: 83

Met Glu Leu Ser Leu Ser Trp Phe Phe Leu Leu Thr Ile Ile Gln Gly
1               5                   10                  15

Val Gln Cys Met Asp Leu Leu His Lys Asn Met Lys His Leu Trp Phe
                20                  25                  30

Phe Leu Leu Leu Val Ala Ala Pro Arg Trp Val Leu Ser Asx Ala Cys
            35                  40                  45

His Ile Gly Ala Met Asp Leu Leu His Lys Asn Met Lys His Leu Trp
        50                  55                  60

Phe Phe Leu Leu Leu Val Ala Ala Pro Arg Trp Val Leu Ser Met Lys
65                  70                  75                  80

His Leu Trp Phe Phe Phe Leu Leu Val Ala Ala Pro Arg Ser Val Leu
                85                  90                  95

Ser Asx Ala Cys His Ile Gly Ala Met Lys His Leu Trp Phe Phe Phe
                100                 105                 110

Leu Leu Val Ala Ala Pro Arg Ser Val Leu Ser Met Glu Leu Gly Leu
            115                 120                 125

Ser Trp Val Phe Leu Val Ser Leu Leu Ala Gly Val Gln Cys Asx Ala
        130                 135                 140

Cys His Ile Gly Ala Met Glu Leu Gly Leu Ser Trp Val Phe Leu Val
145                 150                 155                 160

Ser Leu Leu Ala Gly Val Gln Cys Met Glu Phe Gly Leu Ser Trp Ile
                165                 170                 175

Phe Leu Val Val Ile Ile Lys Gly Val Gln Cys Asx Ala Cys His Ile
            180                 185                 190

Gly Ala Met Glu Phe Gly Leu Ser Trp Ile Phe Leu Val Val Ile Ile
        195                 200                 205

Lys Gly Val Gln Cys Met Asp Trp Thr Trp Ser Ile Leu Phe Leu Val
    210                 215                 220

Ala Ala Ala Thr Gly Ala Gln Ser Ala Ala His His Ile Gly Ala Met
225                 230                 235                 240

Asp Trp Thr Trp Ser Ile Leu Phe Leu Val Ala Ala Thr Gly Ala
                245                 250                 255

Gln Ser Met Asp Trp Thr Trp Arg Leu Leu Phe Leu Val Ala Ala Val
                260                 265                 270

Thr Ser Ala His Ser Ala Ala Leu His Ile Gly Ala Met Asp Trp Thr
            275                 280                 285

Trp Arg Leu Leu Phe Leu Val Ala Ala Val Thr Ser Ala His Ser Met
        290                 295                 300

Glu Phe Gly Leu Ser Trp Val Phe Leu Val Ala Leu Leu Arg Gly Val
305                 310                 315                 320

Gln Cys Cys Ala Glu His Ile Gly Ala Met Glu Phe Gly Leu Ser Trp
                325                 330                 335

Val Phe Leu Val Ala Leu Leu Arg Gly Val Gln Cys Met Gly Trp Thr

-continued

```
                340                 345                 350
    Trp Ser Ile Leu Phe Leu Val Ala Ala Thr Thr Gly Ala Pro Ser Cys
            355                 360                 365
    Ala Glu His Ile Gly Ala Met Gly Trp Thr Trp Ser Ile Leu Phe Leu
        370                 375                 380
    Val Ala Ala Thr Thr Gly Ala Pro Ser Met Asp Trp Thr Trp Arg Val
    385                 390                 395                 400
    Phe Cys Leu Leu Ala Val Ala Pro Gly Val Gln Ser Asx Ala Cys His
                    405                 410                 415
    Ile Gly Ala Met Asp Trp Thr Trp Arg Val Phe Cys Leu Leu Ala Val
                420                 425                 430
    Ala Pro Gly Val Gln Ser Met Asp Leu Met Cys Lys Lys Met Lys His
                435                 440                 445
    Leu Trp Phe Phe Leu Leu Leu Val Ala Ala Pro Arg Trp Val Leu Ser
            450                 455                 460
    Asx Ala Cys His Ile Gly Ala Met Asp Leu Met Cys Lys Lys Met Lys
    465                 470                 475                 480
    His Leu Trp Phe Phe Leu Leu Leu Val Ala Ala Pro Arg Trp Val Leu
                    485                 490                 495
    Ser Met Asp Trp Thr Trp Arg Ile Leu Phe Leu Ala Ala Ala Ala Thr
                500                 505                 510
    Gly Val Gln Ser Ala Ala His His Ile Gly Ala Met Asp Trp Thr Trp
                515                 520                 525
    Arg Ile Leu Phe Leu Ala Ala Ala Ala Thr Gly Val Gln Ser Met Lys
            530                 535                 540
    His Leu Trp Phe Phe Leu Leu Leu Val Ala Ala Pro Arg Trp Val Leu
    545                 550                 555                 560
    Ser Ala Ala His His Ile Gly Ala Met Lys His Leu Trp Phe Phe Leu
                    565                 570                 575
    Leu Leu Val Ala Ala Pro Arg Trp Val Leu Ser Met Glu Leu Gly Leu
                580                 585                 590
    Ser Trp Val Phe Leu Val Ala Ile Leu Glu Gly Val His Cys Asx Ala
                595                 600                 605
    Cys His Ile Gly Ala Met Glu Leu Gly Leu Ser Trp Val Phe Leu Val
        610                 615                 620
    Ala Ile Leu Glu Gly Val His Cys Met Asp Leu Met Cys Lys Lys Met
    625                 630                 635                 640
    Lys His Leu Trp Phe Phe Leu Leu Leu Val Ala Ala Pro Gly Trp Val
                    645                 650                 655
    Leu Ser Asx Ala Cys His Ile Gly Ala Met Asp Trp Thr Trp Ser Ile
                660                 665                 670
    Leu Phe Leu Val Ala Ala Thr Gly Val His Ser
                675                 680
```

<210> SEQ ID NO 84
<211> LENGTH: 19
<212> TYPE: PRT
<213> ORGANISM: Homo sapiens

<400> SEQUENCE: 84

```
Met Glu Leu Gly Leu Ser Trp Ile Phe Leu Leu Ala Ile Leu Lys Gly
1               5                   10                  15

Val Gln Cys
```

<210> SEQ ID NO 85
<211> LENGTH: 19
<212> TYPE: PRT
<213> ORGANISM: Homo sapiens

<400> SEQUENCE: 85

Met Glu Leu Gly Leu Ser Trp Ile Phe Leu Val Ala Ile Leu Lys Gly
1               5                   10                  15

Val Gln Cys

<210> SEQ ID NO 86
<211> LENGTH: 19
<212> TYPE: PRT
<213> ORGANISM: Homo sapiens

<400> SEQUENCE: 86

Met Asp Phe Gly Leu Ala Trp Val Phe Leu Val Ala Leu Leu Arg Gly
1               5                   10                  15

Val Gln Cys

<210> SEQ ID NO 87
<211> LENGTH: 19
<212> TYPE: PRT
<213> ORGANISM: Homo sapiens

<400> SEQUENCE: 87

Met Glu Leu Gly Leu Arg Trp Val Leu Leu Val Ala Ile Leu Glu Gly
1               5                   10                  15

Val His Cys

<210> SEQ ID NO 88
<211> LENGTH: 19
<212> TYPE: PRT
<213> ORGANISM: Homo sapiens

<400> SEQUENCE: 88

Met Glu Phe Gly Leu Ser Trp Val Phe Leu Val Ala Leu Leu Arg Gly
1               5                   10                  15

Val Gln Cys

<210> SEQ ID NO 89
<211> LENGTH: 26
<212> TYPE: PRT
<213> ORGANISM: Homo sapiens

<400> SEQUENCE: 89

Met Gly Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 90
<211> LENGTH: 19
<212> TYPE: PRT
<213> ORGANISM: Homo sapiens

<400> SEQUENCE: 90

Met Arg His Leu Trp Phe Phe Leu Leu Leu Val Ala Ala Pro Arg Trp
1               5                   10                  15

Val Leu Ser

```
<210> SEQ ID NO 91
<211> LENGTH: 26
<212> TYPE: PRT
<213> ORGANISM: Homo sapiens

<400> SEQUENCE: 91

Met Asp Leu Leu His Lys Asn Met Lys His Leu Trp Phe Phe Leu Leu
1               5                   10                  15

Leu Val Ala Ala Pro Arg Trp Gly Leu Ser
            20                  25

<210> SEQ ID NO 92
<211> LENGTH: 18
<212> TYPE: PRT
<213> ORGANISM: Homo sapiens

<400> SEQUENCE: 92

Met Asp Trp Thr Trp Ile Leu Phe Leu Val Ala Ala Thr Arg Val
1               5                   10                  15

His Ser

<210> SEQ ID NO 93
<211> LENGTH: 19
<212> TYPE: PRT
<213> ORGANISM: Homo sapiens

<400> SEQUENCE: 93

Met Asp Trp Thr Trp Arg Ile Leu Phe Leu Val Ala Ala Thr Gly
1               5                   10                  15

Ala His Ser

<210> SEQ ID NO 94
<211> LENGTH: 21
<212> TYPE: PRT
<213> ORGANISM: Homo sapiens

<400> SEQUENCE: 94

Met Glu Phe Gly Leu Ser Trp Val Phe Leu Val Ala Ile Ile Lys Gly
1               5                   10                  15

Val Gln Cys Gln Val
            20

<210> SEQ ID NO 95
<211> LENGTH: 26
<212> TYPE: PRT
<213> ORGANISM: Homo sapiens

<400> SEQUENCE: 95

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 96
<211> LENGTH: 26
<212> TYPE: PRT
<213> ORGANISM: Homo sapiens

<400> SEQUENCE: 96

Met Asp Leu Leu His Lys Asn Met Lys His Leu Trp Phe Phe Leu Leu
1               5                   10                  15

Leu Val Ala Ala Pro Arg Trp Val Leu Ser
```

```
                   20                  25

<210> SEQ ID NO 97
<211> LENGTH: 26
<212> TYPE: PRT
<213> ORGANISM: Homo sapiens

<400> SEQUENCE: 97

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 98
<211> LENGTH: 19
<212> TYPE: PRT
<213> ORGANISM: Homo sapiens

<400> SEQUENCE: 98

Met Glu Phe Gly Leu Ser Trp Leu Phe Leu Val Ala Ile Leu Lys Gly
1               5                   10                  15

Val Gln Cys

<210> SEQ ID NO 99
<211> LENGTH: 19
<212> TYPE: PRT
<213> ORGANISM: Homo sapiens

<400> SEQUENCE: 99

Met Asp Trp Thr Trp Arg Ile Leu Phe Leu Val Ala Ala Ala Thr Asp
1               5                   10                  15

Ala Tyr Ser

<210> SEQ ID NO 100
<211> LENGTH: 19
<212> TYPE: PRT
<213> ORGANISM: Homo sapiens

<400> SEQUENCE: 100

Met Glu Phe Gly Leu Ser Trp Val Phe Leu Val Ala Leu Leu Arg Gly
1               5                   10                  15

Val Gln Cys

<210> SEQ ID NO 101
<211> LENGTH: 19
<212> TYPE: PRT
<213> ORGANISM: Homo sapiens

<400> SEQUENCE: 101

Met Lys His Leu Trp Phe Phe Leu Leu Leu Val Ala Ala Pro Arg Trp
1               5                   10                  15

Val Leu Ser

<210> SEQ ID NO 102
<211> LENGTH: 19
<212> TYPE: PRT
<213> ORGANISM: Homo sapiens

<400> SEQUENCE: 102

Met Glu Leu Gly Leu Arg Trp Val Phe Leu Val Ala Ile Leu Glu Gly
1               5                   10                  15
```

Val Gln Cys

<210> SEQ ID NO 103
<211> LENGTH: 20
<212> TYPE: PRT
<213> ORGANISM: Homo sapiens

<400> SEQUENCE: 103

Met Ser Val Ser Phe Leu Ile Phe Leu Pro Val Leu Gly Leu Pro Trp
1               5                   10                  15

Gly Val Leu Ser
            20

<210> SEQ ID NO 104
<211> LENGTH: 19
<212> TYPE: PRT
<213> ORGANISM: Homo sapiens

<400> SEQUENCE: 104

Met Lys His Leu Trp Phe Phe Leu Leu Leu Val Ala Thr Pro Arg Trp
1               5                   10                  15

Val Leu Ser

<210> SEQ ID NO 105
<211> LENGTH: 19
<212> TYPE: PRT
<213> ORGANISM: Homo sapiens

<400> SEQUENCE: 105

Met Asp Trp Thr Trp Arg Phe Leu Phe Val Val Ala Ala Ala Thr Gly
1               5                   10                  15

Val Gln Ser

<210> SEQ ID NO 106
<211> LENGTH: 26
<212> TYPE: PRT
<213> ORGANISM: Homo sapiens

<400> SEQUENCE: 106

Met Asp Leu Leu Cys Lys Asn Met Lys His Leu Trp Phe Phe Leu Leu
1               5                   10                  15

Leu Val Ala Ala Pro Arg Trp Val Leu Ser
            20                  25

<210> SEQ ID NO 107
<211> LENGTH: 19
<212> TYPE: PRT
<213> ORGANISM: Homo sapiens

<400> SEQUENCE: 107

Met Glu Phe Gly Leu Ser Trp Val Phe Leu Val Ala Leu Phe Arg Gly
1               5                   10                  15

Val Gln Cys

<210> SEQ ID NO 108
<211> LENGTH: 19
<212> TYPE: PRT
<213> ORGANISM: Homo sapiens

<400> SEQUENCE: 108

Met Asp Trp Thr Trp Arg Ile Leu Phe Leu Val Ala Ala Ala Thr Gly
1               5                   10                  15

Ala His Ser

<210> SEQ ID NO 109
<211> LENGTH: 26
<212> TYPE: PRT
<213> ORGANISM: Homo sapiens

<400> SEQUENCE: 109

Met Glu Leu Met Cys Lys Lys Met Lys His Leu Trp Phe Phe Leu Leu
1               5                   10                  15

Leu Val Ala Ala Pro Arg Trp Val Leu Ser
            20                  25

<210> SEQ ID NO 110
<211> LENGTH: 19
<212> TYPE: PRT
<213> ORGANISM: Homo sapiens

<400> SEQUENCE: 110

Met Glu Leu Gly Leu Ser Trp Val Phe Leu Val Ala Ile Leu Glu Gly
1               5                   10                  15

Val Gln Cys

<210> SEQ ID NO 111
<211> LENGTH: 19
<212> TYPE: PRT
<213> ORGANISM: Homo sapiens

<400> SEQUENCE: 111

Met Glu Phe Gly Leu Ser Trp Val Phe Leu Val Ala Leu Leu Arg Gly
1               5                   10                  15

Val Gln Cys

<210> SEQ ID NO 112
<211> LENGTH: 19
<212> TYPE: PRT
<213> ORGANISM: Homo sapiens

<400> SEQUENCE: 112

Met Glu Leu Gly Leu Ser Trp Val Phe Leu Val Ala Ile Leu Glu Gly
1               5                   10                  15

Val Gln Cys

<210> SEQ ID NO 113
<211> LENGTH: 23
<212> TYPE: PRT
<213> ORGANISM: Homo sapiens

<400> SEQUENCE: 113

Met Cys Lys Thr Met Lys Gln Leu Trp Phe Phe Leu Leu Leu Val Ala
1               5                   10                  15

Ala Pro Arg Trp Val Leu Ser
            20

<210> SEQ ID NO 114
<211> LENGTH: 19
<212> TYPE: PRT
<213> ORGANISM: Homo sapiens

<400> SEQUENCE: 114

Met Glu Leu Gly Leu Asn Trp Val Leu Leu Val Ala Ile Leu Glu Gly

-continued

```
                1               5                  10                  15

Val Gln Cys

<210> SEQ ID NO 115
<211> LENGTH: 19
<212> TYPE: PRT
<213> ORGANISM: Homo sapiens

<400> SEQUENCE: 115

Met Lys His Leu Trp Phe Phe Leu Leu Leu Val Ala Ala Pro Arg Trp
1               5                   10                  15

Val Leu Ser

<210> SEQ ID NO 116
<211> LENGTH: 19
<212> TYPE: PRT
<213> ORGANISM: Homo sapiens

<400> SEQUENCE: 116

Met Glu Leu Gly Leu Arg Trp Val Phe Leu Val Ala Ile Leu Glu Gly
1               5                   10                  15

Val Gln Cys

<210> SEQ ID NO 117
<211> LENGTH: 19
<212> TYPE: PRT
<213> ORGANISM: Homo sapiens

<400> SEQUENCE: 117

Met Glu Phe Gly Leu Ser Trp Val Phe Leu Val Ala Ile Leu Lys Gly
1               5                   10                  15

Val Gln Cys

<210> SEQ ID NO 118
<211> LENGTH: 19
<212> TYPE: PRT
<213> ORGANISM: Homo sapiens

<400> SEQUENCE: 118

Met Glu Phe Gly Leu Ser Trp Val Leu Leu Val Val Phe Leu Gln Gly
1               5                   10                  15

Val Gln Cys

<210> SEQ ID NO 119
<211> LENGTH: 19
<212> TYPE: PRT
<213> ORGANISM: Homo sapiens

<400> SEQUENCE: 119

Met Asp Trp Thr Trp Arg Phe Leu Phe Val Val Ala Ala Ala Thr Gly
1               5                   10                  15

Val Gln Ser

<210> SEQ ID NO 120
<211> LENGTH: 19
<212> TYPE: PRT
<213> ORGANISM: Homo sapiens

<400> SEQUENCE: 120

Met Glu Phe Gly Leu Ser Trp Leu Phe Leu Val Ala Ile Leu Lys Gly
1               5                   10                  15
```

Val Gln Cys

<210> SEQ ID NO 121
<211> LENGTH: 19
<212> TYPE: PRT
<213> ORGANISM: Homo sapiens

<400> SEQUENCE: 121

Met Asp Cys Thr Trp Arg Ile Leu Leu Leu Val Ala Val Ala Thr Gly
1               5                   10                  15

Thr His Ala

<210> SEQ ID NO 122
<211> LENGTH: 19
<212> TYPE: PRT
<213> ORGANISM: Homo sapiens

<400> SEQUENCE: 122

Met Asp Thr Leu Cys Ser Thr Leu Leu Leu Thr Ile Pro Ser Trp
1               5                   10                  15

Val Leu Ser

<210> SEQ ID NO 123
<211> LENGTH: 19
<212> TYPE: PRT
<213> ORGANISM: Homo sapiens

<400> SEQUENCE: 123

Met Asp Leu Gly Leu Tyr Trp Val Phe Leu Val Ala Ile Leu Glu Gly
1               5                   10                  15

Val Glu Cys

<210> SEQ ID NO 124
<211> LENGTH: 19
<212> TYPE: PRT
<213> ORGANISM: Homo sapiens

<400> SEQUENCE: 124

Met Asp Trp Thr Trp Arg Ile Leu Phe Leu Val Ala Ala Ala Thr Ser
1               5                   10                  15

Ala His Ser

<210> SEQ ID NO 125
<211> LENGTH: 19
<212> TYPE: PRT
<213> ORGANISM: Homo sapiens

<400> SEQUENCE: 125

Met Glu Phe Gly Leu Ser Trp Val Phe Leu Val Ala Val Ile Lys Gly
1               5                   10                  15

Val Gln Cys

<210> SEQ ID NO 126
<211> LENGTH: 26
<212> TYPE: PRT
<213> ORGANISM: Homo sapiens

<400> SEQUENCE: 126

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 127
<211> LENGTH: 19
<212> TYPE: PRT
<213> ORGANISM: Homo sapiens

<400> SEQUENCE: 127

Met Glu Leu Gly Leu Cys Trp Val Phe Leu Val Ala Ile Leu Glu Gly
1               5                   10                  15

Val Gln Cys

<210> SEQ ID NO 128
<211> LENGTH: 19
<212> TYPE: PRT
<213> ORGANISM: Homo sapiens

<400> SEQUENCE: 128

Met Asp Trp Thr Trp Arg Ile Leu Phe Leu Val Thr Ala Ala Thr Gly
1               5                   10                  15

Ala His Ser

<210> SEQ ID NO 129
<211> LENGTH: 19
<212> TYPE: PRT
<213> ORGANISM: Homo sapiens

<400> SEQUENCE: 129

Met Asp Trp Thr Trp Ser Ile Leu Phe Leu Val Ala Ala Ala Thr Gly
1               5                   10                  15

Ala His Ser

<210> SEQ ID NO 130
<211> LENGTH: 19
<212> TYPE: PRT
<213> ORGANISM: Homo sapiens

<400> SEQUENCE: 130

Met Gly Ser Thr Ala Ile Leu Ala Leu Leu Leu Ala Val Leu Gln Gly
1               5                   10                  15

Val Cys Ala

<210> SEQ ID NO 131
<211> LENGTH: 19
<212> TYPE: PRT
<213> ORGANISM: Homo sapiens

<400> SEQUENCE: 131

Met Asp Trp Thr Trp Arg Ile Leu Phe Leu Val Ala Ala Ala Thr Ser
1               5                   10                  15

Ala His Ser

<210> SEQ ID NO 132
<211> LENGTH: 19
<212> TYPE: PRT
<213> ORGANISM: Homo sapiens

<400> SEQUENCE: 132

Met Glu Leu Gly Leu Ser Trp Val Phe Leu Val Ala Ile Leu Glu Gly
1               5                   10                  15

```
Val Gln Cys

<210> SEQ ID NO 133
<211> LENGTH: 19
<212> TYPE: PRT
<213> ORGANISM: Homo sapiens

<400> SEQUENCE: 133

Met Asp Arg Thr Trp Arg Leu Leu Phe Val Val Ala Ala Ala Thr Gly
1               5                   10                  15

Val Gln Ser

<210> SEQ ID NO 134
<211> LENGTH: 19
<212> TYPE: PRT
<213> ORGANISM: Homo sapiens

<400> SEQUENCE: 134

Met Asp Trp Thr Trp Arg Phe Leu Phe Val Val Ala Ala Ala Thr Gly
1               5                   10                  15

Val Gln Ser

<210> SEQ ID NO 135
<211> LENGTH: 19
<212> TYPE: PRT
<213> ORGANISM: Homo sapiens

<400> SEQUENCE: 135

Met Asp Trp Thr Trp Arg Phe Leu Ile Val Val Ala Ala Ala Thr Gly
1               5                   10                  15

Val Gln Ser

<210> SEQ ID NO 136
<211> LENGTH: 19
<212> TYPE: PRT
<213> ORGANISM: Homo sapiens

<400> SEQUENCE: 136

Met Asp Trp Thr Trp Arg Ile Leu Phe Leu Val Ala Ala Ala Thr Gly
1               5                   10                  15

Ala His Ser

<210> SEQ ID NO 137
<211> LENGTH: 19
<212> TYPE: PRT
<213> ORGANISM: Homo sapiens

<400> SEQUENCE: 137

Met Glu Leu Gly Leu Arg Trp Val Phe Leu Ile Ala Thr Leu Ala Gly
1               5                   10                  15

Ala Arg Cys

<210> SEQ ID NO 138
<211> LENGTH: 19
<212> TYPE: PRT
<213> ORGANISM: Homo sapiens

<400> SEQUENCE: 138

Met Glu Leu Gly Leu Arg Trp Val Phe Leu Ile Ala Thr Leu Ala Gly
1               5                   10                  15

Ala Arg Cys
```

<210> SEQ ID NO 139
<211> LENGTH: 19
<212> TYPE: PRT
<213> ORGANISM: Homo sapiens

<400> SEQUENCE: 139

Met Glu Phe Gly Leu Ser Trp Val Tyr Leu Val Ala Ile Leu Lys Gly
1               5                   10                  15

Val Gln Cys

<210> SEQ ID NO 140
<211> LENGTH: 19
<212> TYPE: PRT
<213> ORGANISM: Homo sapiens

<400> SEQUENCE: 140

Met Asp Trp Thr Trp Arg Val Phe Cys Leu Leu Ala Val Ile Ser Gly
1               5                   10                  15

Gly Gln Ser

<210> SEQ ID NO 141
<211> LENGTH: 19
<212> TYPE: PRT
<213> ORGANISM: Homo sapiens

<400> SEQUENCE: 141

Met Gly His Pro Trp Phe Phe Leu Leu Leu Val Thr Ala Pro Arg Trp
1               5                   10                  15

Val Leu Ser

<210> SEQ ID NO 142
<211> LENGTH: 19
<212> TYPE: PRT
<213> ORGANISM: Homo sapiens

<400> SEQUENCE: 142

Met Asp Trp Thr Trp Arg Phe Leu Phe Val Val Ala Ala Ala Ala Gly
1               5                   10                  15

Val Gln Ser

<210> SEQ ID NO 143
<211> LENGTH: 19
<212> TYPE: PRT
<213> ORGANISM: Homo sapiens

<400> SEQUENCE: 143

Met Asp Trp Thr Trp Arg Ile Leu Phe Leu Val Ala Ala Ala Thr Glu
1               5                   10                  15

Ala His Ser

<210> SEQ ID NO 144
<211> LENGTH: 19
<212> TYPE: PRT
<213> ORGANISM: Homo sapiens

<400> SEQUENCE: 144

Met Gly Trp Thr Trp Arg Phe Leu Phe Val Val Ala Ala Ala Ala Gly
1               5                   10                  15

Val Gln Ser

<210> SEQ ID NO 145
<211> LENGTH: 19
<212> TYPE: PRT
<213> ORGANISM: Homo sapiens

<400> SEQUENCE: 145

Met Asp Trp Thr Trp Arg Phe Leu Phe Val Val Ala Ala Ala Thr Gly
1               5                   10                  15

Val Gln Ser

<210> SEQ ID NO 146
<211> LENGTH: 19
<212> TYPE: PRT
<213> ORGANISM: Homo sapiens

<400> SEQUENCE: 146

Met Asp Trp Thr Trp Arg Phe Leu Leu Val Val Ala Ala Ala Thr Gly
1               5                   10                  15

Val Pro Ser

<210> SEQ ID NO 147
<211> LENGTH: 19
<212> TYPE: PRT
<213> ORGANISM: Homo sapiens

<400> SEQUENCE: 147

Met Asp Trp Thr Trp Arg Phe Leu Phe Val Val Ala Ala Ala Thr Gly
1               5                   10                  15

Val Gln Ser

<210> SEQ ID NO 148
<211> LENGTH: 19
<212> TYPE: PRT
<213> ORGANISM: Homo sapiens

<400> SEQUENCE: 148

Met Asp Trp Thr Trp Arg Phe Leu Phe Val Val Ala Ala Ala Thr Ser
1               5                   10                  15

Val Gln Ser

<210> SEQ ID NO 149
<211> LENGTH: 19
<212> TYPE: PRT
<213> ORGANISM: Homo sapiens

<400> SEQUENCE: 149

Met Asp Trp Thr Trp Arg Ile Leu Phe Leu Val Ala Ala Ala Thr Gly
1               5                   10                  15

Ala His Ser

<210> SEQ ID NO 150
<211> LENGTH: 19
<212> TYPE: PRT
<213> ORGANISM: Homo sapiens

<400> SEQUENCE: 150

Met Lys His Leu Trp Phe Phe Leu Leu Leu Val Ala Ala Pro Arg Trp
1               5                   10                  15

Val Leu Ser

<210> SEQ ID NO 151
<211> LENGTH: 19
<212> TYPE: PRT
<213> ORGANISM: Homo sapiens

<400> SEQUENCE: 151

Met Asp Cys Thr Trp Arg Ile Leu Leu Leu Val Ala Ala Ala Thr Gly
1               5                   10                  15

Thr His Ala

<210> SEQ ID NO 152
<211> LENGTH: 19
<212> TYPE: PRT
<213> ORGANISM: Homo sapiens

<400> SEQUENCE: 152

Met Asp Trp Thr Trp Arg Ile Leu Phe Leu Val Ala Ala Ala Thr Gly
1               5                   10                  15

Ala His Ser

<210> SEQ ID NO 153
<211> LENGTH: 19
<212> TYPE: PRT
<213> ORGANISM: Homo sapiens

<400> SEQUENCE: 153

Met Asp Trp Thr Trp Arg Phe Leu Phe Val Val Ala Ala Gly Thr Gly
1               5                   10                  15

Val Gln Ser

<210> SEQ ID NO 154
<211> LENGTH: 19
<212> TYPE: PRT
<213> ORGANISM: Homo sapiens

<400> SEQUENCE: 154

Met Glu Phe Gly Leu Ser Trp Leu Phe Leu Val Ala Ile Leu Lys Gly
1               5                   10                  15

Val Gln Cys

<210> SEQ ID NO 155
<211> LENGTH: 19
<212> TYPE: PRT
<213> ORGANISM: Homo sapiens

<400> SEQUENCE: 155

Met Asp Trp Thr Trp Arg Phe Leu Phe Val Val Ala Ala Ala Thr Gly
1               5                   10                  15

Val Gln Ser

<210> SEQ ID NO 156
<211> LENGTH: 27
<212> TYPE: PRT
<213> ORGANISM: Homo sapiens

<400> SEQUENCE: 156

Met Ala Lys Thr Asn Leu Phe Leu Phe Leu Ile Phe Ser Leu Leu Leu
1               5                   10                  15

Ser Leu Ser Ser Ala Ala Gln Pro Ala Met Ala
            20                  25

<210> SEQ ID NO 157
<211> LENGTH: 19
<212> TYPE: PRT
<213> ORGANISM: Homo sapiens

<400> SEQUENCE: 157

Met Asp Trp Thr Trp Arg Phe Leu Phe Val Val Ala Ala Val Thr Gly
1               5                   10                  15

Val Gln Ser

<210> SEQ ID NO 158
<211> LENGTH: 19
<212> TYPE: PRT
<213> ORGANISM: Homo sapiens

<400> SEQUENCE: 158

Met Glu Leu Gly Leu Ser Trp Val Phe Leu Val Val Ile Leu Glu Gly
1               5                   10                  15

Val Gln Cys

<210> SEQ ID NO 159
<211> LENGTH: 19
<212> TYPE: PRT
<213> ORGANISM: Homo sapiens

<400> SEQUENCE: 159

Met Glu Phe Gly Leu Ser Trp Ile Phe Leu Ala Thr Ile Leu Lys Gly
1               5                   10                  15

Val Gln Cys

<210> SEQ ID NO 160
<211> LENGTH: 19
<212> TYPE: PRT
<213> ORGANISM: Homo sapiens

<400> SEQUENCE: 160

Met Glu Phe Gly Leu Ser Trp Val Phe Leu Val Ala Ile Ile Lys Gly
1               5                   10                  15

Val Gln Cys

<210> SEQ ID NO 161
<211> LENGTH: 19
<212> TYPE: PRT
<213> ORGANISM: Homo sapiens

<400> SEQUENCE: 161

Met Asp Trp Thr Trp Arg Phe Leu Phe Val Val Ala Ala Ala Thr Gly
1               5                   10                  15

Val Gln Ser

<210> SEQ ID NO 162
<211> LENGTH: 19
<212> TYPE: PRT
<213> ORGANISM: Homo sapiens

<400> SEQUENCE: 162

Met Glu Phe Gly Leu Arg Trp Val Phe Leu Val Ala Ile Leu Lys Asp
1               5                   10                  15

Val Gln Cys

<210> SEQ ID NO 163

```
<211> LENGTH: 19
<212> TYPE: PRT
<213> ORGANISM: Homo sapiens

<400> SEQUENCE: 163

Met Glu Phe Gly Leu Ser Trp Val Phe Leu Val Ala Ile Leu Lys Gly
1               5                   10                  15

Val Gln Cys

<210> SEQ ID NO 164
<211> LENGTH: 19
<212> TYPE: PRT
<213> ORGANISM: Homo sapiens

<400> SEQUENCE: 164

Met Asp Trp Thr Trp Ser Ile Leu Phe Leu Val Thr Ala Ala Thr Gly
1               5                   10                  15

Ala His Ser

<210> SEQ ID NO 165
<211> LENGTH: 19
<212> TYPE: PRT
<213> ORGANISM: Homo sapiens

<400> SEQUENCE: 165

Met Glu Phe Gly Leu Ser Trp Val Phe Leu Val Ala Leu Leu Arg Gly
1               5                   10                  15

Val Gln Cys

<210> SEQ ID NO 166
<211> LENGTH: 19
<212> TYPE: PRT
<213> ORGANISM: Homo sapiens

<400> SEQUENCE: 166

Met Glu Phe Gly Leu Ser Cys Val Phe Leu Val Ala Ile Phe Lys Gly
1               5                   10                  15

Val His Cys

<210> SEQ ID NO 167
<211> LENGTH: 19
<212> TYPE: PRT
<213> ORGANISM: Homo sapiens

<400> SEQUENCE: 167

Met Glu Leu Gly Leu Ser Trp Ile Phe Leu Val Ala Leu Leu Arg Gly
1               5                   10                  15

Val Gln Cys

<210> SEQ ID NO 168
<211> LENGTH: 19
<212> TYPE: PRT
<213> ORGANISM: Homo sapiens

<400> SEQUENCE: 168

Met Asp Trp Thr Trp Ser Ile Leu Phe Leu Val Ala Gly Ala Ser Gly
1               5                   10                  15

Ala His Ser

<210> SEQ ID NO 169
<211> LENGTH: 19
```

```
<212> TYPE: PRT
<213> ORGANISM: Homo sapiens

<400> SEQUENCE: 169

Met Asp Trp Thr Trp Arg Val Leu Phe Val Val Ala Ala Ser Thr Gly
1               5                   10                  15

Val Gln Ser

<210> SEQ ID NO 170
<211> LENGTH: 19
<212> TYPE: PRT
<213> ORGANISM: Homo sapiens

<400> SEQUENCE: 170

Met Glu Leu Gly Leu Thr Trp Ile Phe Leu Leu Ala Ile Leu Lys Gly
1               5                   10                  15

Val Gln Cys

<210> SEQ ID NO 171
<211> LENGTH: 19
<212> TYPE: PRT
<213> ORGANISM: Homo sapiens

<400> SEQUENCE: 171

Met Glu Phe Gly Leu Ser Trp Leu Phe Leu Val Thr Ile Leu Lys Gly
1               5                   10                  15

Val Gln Cys

<210> SEQ ID NO 172
<211> LENGTH: 19
<212> TYPE: PRT
<213> ORGANISM: Homo sapiens

<400> SEQUENCE: 172

Met Asp Trp Thr Trp Ser Ile Leu Phe Leu Val Ala Ala Ala Thr Gly
1               5                   10                  15

Ala Arg Pro

<210> SEQ ID NO 173
<211> LENGTH: 19
<212> TYPE: PRT
<213> ORGANISM: Homo sapiens

<400> SEQUENCE: 173

Met Asp Trp Thr Trp Arg Val Phe Cys Leu Leu Ala Val Ala Pro Gly
1               5                   10                  15

Ala His Ser

<210> SEQ ID NO 174
<211> LENGTH: 19
<212> TYPE: PRT
<213> ORGANISM: Homo sapiens

<400> SEQUENCE: 174

Met Glu Phe Gly Leu Ser Trp Leu Leu Leu Val Ala Ile Leu Lys Gly
1               5                   10                  15

Val Gln Cys

<210> SEQ ID NO 175
<211> LENGTH: 19
<212> TYPE: PRT
```

<213> ORGANISM: Homo sapiens

<400> SEQUENCE: 175

Met Lys His Leu Trp Phe Phe Leu Leu Leu Val Ala Ala Pro Arg Trp
1               5                   10                  15

Val Leu Ser

<210> SEQ ID NO 176
<211> LENGTH: 19
<212> TYPE: PRT
<213> ORGANISM: Homo sapiens

<400> SEQUENCE: 176

Met Gly Ser Thr Ala Ile Leu Ala Leu Leu Ala Val Leu Gln Gly
1               5                   10                  15

Val Cys Ala

<210> SEQ ID NO 177
<211> LENGTH: 19
<212> TYPE: PRT
<213> ORGANISM: Homo sapiens

<400> SEQUENCE: 177

Met Glu Phe Gly Leu Ser Trp Val Phe Leu Val Ala Ile Leu Lys Gly
1               5                   10                  15

Val Gln Cys

<210> SEQ ID NO 178
<211> LENGTH: 19
<212> TYPE: PRT
<213> ORGANISM: Homo sapiens

<400> SEQUENCE: 178

Met Glu Phe Gly Leu Ser Trp Val Phe Leu Val Ala Ile Leu Lys Gly
1               5                   10                  15

Val Gln Cys

<210> SEQ ID NO 179
<211> LENGTH: 26
<212> TYPE: PRT
<213> ORGANISM: Homo sapiens

<400> SEQUENCE: 179

Met Asp Leu Lys Cys Lys Lys Met Lys Arg Leu Trp Leu Phe Leu Leu
1               5                   10                  15

Leu Val Ala Ala Pro Arg Trp Val Leu Ser
                20                  25

<210> SEQ ID NO 180
<211> LENGTH: 19
<212> TYPE: PRT
<213> ORGANISM: Homo sapiens

<400> SEQUENCE: 180

Met Lys His Leu Trp Phe Phe Leu Leu Leu Val Ala Ala Pro Arg Trp
1               5                   10                  15

Val Leu Ser

<210> SEQ ID NO 181
<211> LENGTH: 19
<212> TYPE: PRT

<213> ORGANISM: Homo sapiens

<400> SEQUENCE: 181

Met Glu Leu Gly Leu Ser Trp Ile Phe Leu Leu Ala Ile Leu Lys Gly
1               5                   10                  15

Val Gln Cys

<210> SEQ ID NO 182
<211> LENGTH: 19
<212> TYPE: PRT
<213> ORGANISM: Homo sapiens

<400> SEQUENCE: 182

Met Glu Phe Gly Leu Ser Trp Ile Phe Leu Val Val Ile Leu Lys Gly
1               5                   10                  15

Val Gln Cys

<210> SEQ ID NO 183
<211> LENGTH: 19
<212> TYPE: PRT
<213> ORGANISM: Homo sapiens

<400> SEQUENCE: 183

Met Glu Phe Gly Leu Ser Cys Leu Phe Leu Val Ala Ile Leu Lys Gly
1               5                   10                  15

Val Arg Cys

<210> SEQ ID NO 184
<211> LENGTH: 19
<212> TYPE: PRT
<213> ORGANISM: Homo sapiens

<400> SEQUENCE: 184

Met Glu Phe Gly Leu Ser Trp Val Phe Leu Val Ala Ile Leu Lys Gly
1               5                   10                  15

Val Gln Cys

<210> SEQ ID NO 185
<211> LENGTH: 19
<212> TYPE: PRT
<213> ORGANISM: Homo sapiens

<400> SEQUENCE: 185

Met Asp Trp Thr Trp Arg Val Phe Cys Leu Leu Ala Val Ala Pro Gly
1               5                   10                  15

Ala Asn Ser

<210> SEQ ID NO 186
<211> LENGTH: 19
<212> TYPE: PRT
<213> ORGANISM: Homo sapiens

<400> SEQUENCE: 186

Met Glu Phe Trp Leu Ser Trp Val Phe Leu Val Ala Ile Leu Lys Gly
1               5                   10                  15

Val Gln Cys

<210> SEQ ID NO 187
<211> LENGTH: 19
<212> TYPE: PRT
<213> ORGANISM: Homo sapiens -continued

<400> SEQUENCE: 187

Met Gly Ser Thr Ala Ile Leu Ala Leu Leu Ala Val Leu Gln Gly
1               5                   10                  15

Val Cys Ala

<210> SEQ ID NO 188
<211> LENGTH: 19
<212> TYPE: PRT
<213> ORGANISM: Homo sapiens

<400> SEQUENCE: 188

Met Glu Leu Gly Leu Arg Trp Val Phe Leu Val Ala Leu Leu Glu Gly
1               5                   10                  15

Val His Cys

<210> SEQ ID NO 189
<211> LENGTH: 19
<212> TYPE: PRT
<213> ORGANISM: Homo sapiens

<400> SEQUENCE: 189

Met Lys Phe Gly Leu Ser Trp Ile Phe Leu Pro Ala Ile Leu Lys Gly
1               5                   10                  15

Val Gln Cys

<210> SEQ ID NO 190
<211> LENGTH: 19
<212> TYPE: PRT
<213> ORGANISM: Homo sapiens

<400> SEQUENCE: 190

Met Glu Phe Gly Leu Ser Trp Ile Phe Leu Ala Ala Ile Leu Lys Gly
1               5                   10                  15

Val Gln Cys

<210> SEQ ID NO 191
<211> LENGTH: 19
<212> TYPE: PRT
<213> ORGANISM: Homo sapiens

<400> SEQUENCE: 191

Met Asp Trp Thr Trp Thr Ile Leu Phe Leu Val Ala Gly Ala Thr Gly
1               5                   10                  15

Val Lys Ser

<210> SEQ ID NO 192
<211> LENGTH: 19
<212> TYPE: PRT
<213> ORGANISM: Homo sapiens

<400> SEQUENCE: 192

Met Glu Phe Gly Leu Ser Trp Ile Phe Leu Ala Ala Ile Leu Lys Gly
1               5                   10                  15

Val Gln Gly

<210> SEQ ID NO 193
<211> LENGTH: 19
<212> TYPE: PRT
<213> ORGANISM: Homo sapiens -continued

```
<400> SEQUENCE: 193

Met Glu Phe Gly Leu Ser Trp Val Phe Leu Val Ala Ile Leu Lys Gly
1               5                   10                  15

Val Gln Cys

<210> SEQ ID NO 194
<211> LENGTH: 19
<212> TYPE: PRT
<213> ORGANISM: Homo sapiens

<400> SEQUENCE: 194

Met Glu Phe Gly Leu Ser Trp Val Phe Leu Val Ala Ile Leu Lys Gly
1               5                   10                  15

Val Gln Cys

<210> SEQ ID NO 195
<211> LENGTH: 19
<212> TYPE: PRT
<213> ORGANISM: Homo sapiens

<400> SEQUENCE: 195

Met Lys His Leu Trp Phe Phe Leu Leu Leu Val Ala Ala Pro Arg Trp
1               5                   10                  15

Val Leu Ser

<210> SEQ ID NO 196
<211> LENGTH: 26
<212> TYPE: PRT
<213> ORGANISM: Homo sapiens

<400> SEQUENCE: 196

Met Asp Leu Leu Cys Lys Lys Met Lys His Leu Trp Phe Phe Leu Leu
1               5                   10                  15

Leu Val Ala Ala Pro Arg Trp Val Leu Ser
            20                  25

<210> SEQ ID NO 197
<211> LENGTH: 19
<212> TYPE: PRT
<213> ORGANISM: Homo sapiens

<400> SEQUENCE: 197

Met Glu Phe Gly Leu Ser Trp Val Phe Leu Val Ala Leu Leu Arg Gly
1               5                   10                  15

Val Gln Cys

<210> SEQ ID NO 198
<211> LENGTH: 19
<212> TYPE: PRT
<213> ORGANISM: Homo sapiens

<400> SEQUENCE: 198

Met Asp Trp Thr Trp Arg Phe Leu Phe Val Val Ala Ala Ala Thr Gly
1               5                   10                  15

Val Gln Ser

<210> SEQ ID NO 199
<211> LENGTH: 19
<212> TYPE: PRT
<213> ORGANISM: Homo sapiens
```

```
<400> SEQUENCE: 199

Met Lys His Leu Trp Phe Phe Leu Leu Val Ala Ala Pro Arg Trp
1               5                   10                  15

Val Leu Ser

<210> SEQ ID NO 200
<211> LENGTH: 19
<212> TYPE: PRT
<213> ORGANISM: Homo sapiens

<400> SEQUENCE: 200

Met Glu Leu Gly Leu Ser Trp Val Phe Leu Val Ala Ile Leu Glu Gly
1               5                   10                  15

Val Gln Cys

<210> SEQ ID NO 201
<211> LENGTH: 19
<212> TYPE: PRT
<213> ORGANISM: Homo sapiens

<400> SEQUENCE: 201

Met Asp Trp Thr Trp Thr Phe Leu Phe Val Val Ala Ala Ala Thr Gly
1               5                   10                  15

Val Gln Ser

<210> SEQ ID NO 202
<211> LENGTH: 26
<212> TYPE: PRT
<213> ORGANISM: Homo sapiens

<400> SEQUENCE: 202

Met Asp Leu Leu Cys Lys Asn Met Lys His Leu Trp Phe Phe Leu Leu
1               5                   10                  15

Leu Val Ala Ala Pro Arg Trp Val Leu Ser
            20                  25

<210> SEQ ID NO 203
<211> LENGTH: 19
<212> TYPE: PRT
<213> ORGANISM: Homo sapiens

<400> SEQUENCE: 203

Met Asp Thr Leu Cys Ser Thr Leu Leu Leu Thr Ile Pro Ser Trp
1               5                   10                  15

Val Leu Ser

<210> SEQ ID NO 204
<211> LENGTH: 19
<212> TYPE: PRT
<213> ORGANISM: Homo sapiens

<400> SEQUENCE: 204

Met Glu Phe Gly Leu Asn Trp Val Leu Leu Val Ala Leu Leu Arg Gly
1               5                   10                  15

Val Gln Cys

<210> SEQ ID NO 205
<211> LENGTH: 19
<212> TYPE: PRT
<213> ORGANISM: Homo sapiens
```

-continued

<400> SEQUENCE: 205

Met Asp Trp Thr Trp Arg Phe Leu Phe Val Val Ala Ala Ser Thr Gly
1               5                   10                  15

Val Gln Ser

<210> SEQ ID NO 206
<211> LENGTH: 19
<212> TYPE: PRT
<213> ORGANISM: Homo sapiens

<400> SEQUENCE: 206

Met Glu Phe Gly Leu Ser Trp Val Phe Leu Val Ala Leu Leu Arg Gly
1               5                   10                  15

Val Glu Cys

<210> SEQ ID NO 207
<211> LENGTH: 19
<212> TYPE: PRT
<213> ORGANISM: Homo sapiens

<400> SEQUENCE: 207

Met Asp Trp Thr Trp Arg Phe Leu Phe Val Val Ala Ala Ala Thr Gly
1               5                   10                  15

Val Gln Ser

<210> SEQ ID NO 208
<211> LENGTH: 19
<212> TYPE: PRT
<213> ORGANISM: Homo sapiens

<400> SEQUENCE: 208

Met Glu Phe Gly Leu Ser Trp Val Phe Leu Val Ala Leu Leu Arg Gly
1               5                   10                  15

Val Gln Cys

<210> SEQ ID NO 209
<211> LENGTH: 19
<212> TYPE: PRT
<213> ORGANISM: Homo sapiens

<400> SEQUENCE: 209

Met Asp Trp Thr Trp Arg Phe Leu Phe Val Val Ala Ala Ala Thr Gly
1               5                   10                  15

Val Gln Ser

<210> SEQ ID NO 210
<211> LENGTH: 19
<212> TYPE: PRT
<213> ORGANISM: Homo sapiens

<400> SEQUENCE: 210

Met Asp Trp Thr Trp Arg Phe Leu Phe Val Val Ala Ala Ala Thr Gly
1               5                   10                  15

Val Gln Ser

<210> SEQ ID NO 211
<211> LENGTH: 19
<212> TYPE: PRT
<213> ORGANISM: Homo sapiens

<400> SEQUENCE: 211

Met Asp Leu Gly Leu Ser Trp Leu Phe Leu Val Ala Leu Leu Lys Gly
1               5                   10                  15

Val Gln Cys

<210> SEQ ID NO 212
<211> LENGTH: 19
<212> TYPE: PRT
<213> ORGANISM: Homo sapiens

<400> SEQUENCE: 212

Met Asp Leu Gly Leu Ser Trp Ile Phe Leu Leu Thr Ile Leu Lys Gly
1               5                   10                  15

Val Gln Cys

<210> SEQ ID NO 213
<211> LENGTH: 26
<212> TYPE: PRT
<213> ORGANISM: Homo sapiens

<400> SEQUENCE: 213

Met Asp Val Met Cys Lys Lys Met Lys His Leu Trp Phe Phe Leu Leu
1               5                   10                  15

Leu Val Ala Ala Pro Arg Trp Val Leu Ala
            20                  25

<210> SEQ ID NO 214
<211> LENGTH: 19
<212> TYPE: PRT
<213> ORGANISM: Homo sapiens

<400> SEQUENCE: 214

Met Glu Phe Gly Leu Thr Trp Val Phe Leu Val Ala Val Ile Lys Gly
1               5                   10                  15

Val His Cys

<210> SEQ ID NO 215
<211> LENGTH: 22
<212> TYPE: PRT
<213> ORGANISM: Homo sapiens

<400> SEQUENCE: 215

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 216
<211> LENGTH: 22
<212> TYPE: PRT
<213> ORGANISM: Homo sapiens

<400> SEQUENCE: 216

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 217
<211> LENGTH: 22
<212> TYPE: PRT
<213> ORGANISM: Homo sapiens

```
<400> SEQUENCE: 217

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 218
<211> LENGTH: 22
<212> TYPE: PRT
<213> ORGANISM: Homo sapiens

<400> SEQUENCE: 218

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 219
<211> LENGTH: 22
<212> TYPE: PRT
<213> ORGANISM: Homo sapiens

<400> SEQUENCE: 219

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 220
<211> LENGTH: 22
<212> TYPE: PRT
<213> ORGANISM: Homo sapiens

<400> SEQUENCE: 220

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 221
<211> LENGTH: 22
<212> TYPE: PRT
<213> ORGANISM: Homo sapiens

<400> SEQUENCE: 221

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 222
<211> LENGTH: 22
<212> TYPE: PRT
<213> ORGANISM: Homo sapiens

<400> SEQUENCE: 222

Met Lys Tyr Leu Leu Pro Thr Ala Ala Ala Gly Leu Leu Leu Ala
1               5                   10                  15

Ala Gln Pro Ala Met Ala
            20
```

```
<210> SEQ ID NO 223
<211> LENGTH: 22
<212> TYPE: PRT
<213> ORGANISM: Homo sapiens

<400> SEQUENCE: 223

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 224
<211> LENGTH: 22
<212> TYPE: PRT
<213> ORGANISM: Homo sapiens

<400> SEQUENCE: 224

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 225
<211> LENGTH: 22
<212> TYPE: PRT
<213> ORGANISM: Homo sapiens

<400> SEQUENCE: 225

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 226
<211> LENGTH: 22
<212> TYPE: PRT
<213> ORGANISM: Homo sapiens

<400> SEQUENCE: 226

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 227
<211> LENGTH: 22
<212> TYPE: PRT
<213> ORGANISM: Homo sapiens

<400> SEQUENCE: 227

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 228
<211> LENGTH: 22
<212> TYPE: PRT
<213> ORGANISM: Homo sapiens

<400> SEQUENCE: 228

Met Lys Tyr Leu Leu Pro Thr Ala Ala Ala Gly Leu Leu Leu Leu Ala
```

```
1               5                   10                  15
Ala Gln Pro Ala Met Ala
            20

<210> SEQ ID NO 229
<211> LENGTH: 22
<212> TYPE: PRT
<213> ORGANISM: Homo sapiens

<400> SEQUENCE: 229

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 230
<211> LENGTH: 22
<212> TYPE: PRT
<213> ORGANISM: Homo sapiens

<400> SEQUENCE: 230

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 231
<211> LENGTH: 22
<212> TYPE: PRT
<213> ORGANISM: Homo sapiens

<400> SEQUENCE: 231

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 232
<211> LENGTH: 22
<212> TYPE: PRT
<213> ORGANISM: Homo sapiens

<400> SEQUENCE: 232

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 233
<211> LENGTH: 22
<212> TYPE: PRT
<213> ORGANISM: Homo sapiens

<400> SEQUENCE: 233

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 234
<211> LENGTH: 22
<212> TYPE: PRT
```

<213> ORGANISM: Homo sapiens

<400> SEQUENCE: 234

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 235
<211> LENGTH: 22
<212> TYPE: PRT
<213> ORGANISM: Homo sapiens

<400> SEQUENCE: 235

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 236
<211> LENGTH: 22
<212> TYPE: PRT
<213> ORGANISM: Homo sapiens

<400> SEQUENCE: 236

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 237
<211> LENGTH: 22
<212> TYPE: PRT
<213> ORGANISM: Homo sapiens

<400> SEQUENCE: 237

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 238
<211> LENGTH: 22
<212> TYPE: PRT
<213> ORGANISM: Homo sapiens

<400> SEQUENCE: 238

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 239
<211> LENGTH: 22
<212> TYPE: PRT
<213> ORGANISM: Homo sapiens

<400> SEQUENCE: 239

Met Lys Tyr Leu Leu Pro Thr Ala Ala Ala Gly Leu Leu Leu Leu Ala
1               5                   10                  15

Ala Gln Pro Ala Met Ala
            20

```
<210> SEQ ID NO 240
<211> LENGTH: 22
<212> TYPE: PRT
<213> ORGANISM: Homo sapiens

<400> SEQUENCE: 240

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 241
<211> LENGTH: 22
<212> TYPE: PRT
<213> ORGANISM: Homo sapiens

<400> SEQUENCE: 241

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 242
<211> LENGTH: 22
<212> TYPE: PRT
<213> ORGANISM: Homo sapiens

<400> SEQUENCE: 242

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 243
<211> LENGTH: 22
<212> TYPE: PRT
<213> ORGANISM: Homo sapiens

<400> SEQUENCE: 243

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 244
<211> LENGTH: 22
<212> TYPE: PRT
<213> ORGANISM: Homo sapiens

<400> SEQUENCE: 244

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 245
<211> LENGTH: 22
<212> TYPE: PRT
<213> ORGANISM: Homo sapiens

<400> SEQUENCE: 245
```

-continued

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 246
<211> LENGTH: 22
<212> TYPE: PRT
<213> ORGANISM: Homo sapiens

<400> SEQUENCE: 246

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 247
<211> LENGTH: 22
<212> TYPE: PRT
<213> ORGANISM: Homo sapiens

<400> SEQUENCE: 247

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 248
<211> LENGTH: 22
<212> TYPE: PRT
<213> ORGANISM: Homo sapiens

<400> SEQUENCE: 248

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 249
<211> LENGTH: 22
<212> TYPE: PRT
<213> ORGANISM: Homo sapiens

<400> SEQUENCE: 249

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 250
<211> LENGTH: 22
<212> TYPE: PRT
<213> ORGANISM: Homo sapiens

<400> SEQUENCE: 250

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 251
<211> LENGTH: 22

```
<212> TYPE: PRT
<213> ORGANISM: Homo sapiens

<400> SEQUENCE: 251

Met Lys Tyr Leu Leu Pro Thr Ala Ala Gly Leu Leu Leu Ala
1               5                   10                  15

Ala Gln Pro Ala Met Ala
            20

<210> SEQ ID NO 252
<211> LENGTH: 22
<212> TYPE: PRT
<213> ORGANISM: Homo sapiens

<400> SEQUENCE: 252

Met Lys Tyr Leu Leu Pro Thr Ala Ala Gly Leu Leu Leu Ala
1               5                   10                  15

Ala Gln Pro Ala Met Ala
            20

<210> SEQ ID NO 253
<211> LENGTH: 22
<212> TYPE: PRT
<213> ORGANISM: Homo sapiens

<400> SEQUENCE: 253

Met Lys Tyr Leu Leu Pro Thr Ala Ala Gly Leu Leu Leu His Ala
1               5                   10                  15

Ala Gln Pro Ala Met Ala
            20

<210> SEQ ID NO 254
<211> LENGTH: 22
<212> TYPE: PRT
<213> ORGANISM: Homo sapiens

<400> SEQUENCE: 254

Met Lys Tyr Leu Leu Pro Thr Ala Ala Gly Leu Leu Leu Ala
1               5                   10                  15

Ala Gln Pro Ala Met Ala
            20

<210> SEQ ID NO 255
<211> LENGTH: 20
<212> TYPE: PRT
<213> ORGANISM: Homo sapiens

<400> SEQUENCE: 255

Met Glu Ala Pro Ala Gln Leu Leu Phe Leu Leu Leu Leu Trp Leu Pro
1               5                   10                  15

Asp Ser Thr Gly
            20

<210> SEQ ID NO 256
<211> LENGTH: 20
<212> TYPE: PRT
<213> ORGANISM: Homo sapiens

<400> SEQUENCE: 256

Met Glu Ala Pro Ala Gln Leu Leu Phe Leu Leu Leu Leu Trp Leu Pro
1               5                   10                  15

Asp Thr Thr Gly
```

```
                    20

<210> SEQ ID NO 257
<211> LENGTH: 20
<212> TYPE: PRT
<213> ORGANISM: Homo sapiens

<400> SEQUENCE: 257

Met Glu Thr Pro Ala Gln Leu Leu Phe Leu Leu Leu Leu Trp Leu Pro
1               5                   10                  15

Gly Thr Thr Gly
            20

<210> SEQ ID NO 258
<211> LENGTH: 20
<212> TYPE: PRT
<213> ORGANISM: Homo sapiens

<400> SEQUENCE: 258

Met Glu Thr Pro Ala Gln Leu Leu Phe Leu Leu Leu Leu Trp Leu Pro
1               5                   10                  15

Asp Ile Thr Gly
            20

<210> SEQ ID NO 259
<211> LENGTH: 20
<212> TYPE: PRT
<213> ORGANISM: Homo sapiens

<400> SEQUENCE: 259

Met Glu Ala Pro Ala Gln Leu Leu Phe Leu Leu Leu Leu Trp Leu Pro
1               5                   10                  15

Asp Thr Thr Gly
            20

<210> SEQ ID NO 260
<211> LENGTH: 20
<212> TYPE: PRT
<213> ORGANISM: Homo sapiens

<400> SEQUENCE: 260

Met Arg Leu Pro Ala Gln Leu Leu Gly Leu Leu Met Leu Trp Val Ser
1               5                   10                  15

Gly Ser Ser Gly
            20

<210> SEQ ID NO 261
<211> LENGTH: 20
<212> TYPE: PRT
<213> ORGANISM: Homo sapiens

<400> SEQUENCE: 261

Met Arg Leu Pro Ala Gln Leu Leu Gly Leu Leu Met Leu Trp Val Ser
1               5                   10                  15

Gly Ser Ser Gly
            20

<210> SEQ ID NO 262
<211> LENGTH: 20
<212> TYPE: PRT
<213> ORGANISM: Homo sapiens

<400> SEQUENCE: 262
```

-continued

Met Arg Leu Pro Ala Gln Leu Leu Gly Leu Leu Met Leu Trp Val Ser
1               5                   10                  15

Gly Ser Ser Gly
            20

<210> SEQ ID NO 263
<211> LENGTH: 22
<212> TYPE: PRT
<213> ORGANISM: Homo sapiens

<400> SEQUENCE: 263

Met Asp Met Arg Val Leu Ala Gln Leu Leu Gly Leu Leu Leu Leu Cys
1               5                   10                  15

Phe Pro Gly Ala Arg Cys
            20

<210> SEQ ID NO 264
<211> LENGTH: 22
<212> TYPE: PRT
<213> ORGANISM: Homo sapiens

<400> SEQUENCE: 264

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 265
<211> LENGTH: 22
<212> TYPE: PRT
<213> ORGANISM: Homo sapiens

<400> SEQUENCE: 265

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 266
<211> LENGTH: 22
<212> TYPE: PRT
<213> ORGANISM: Homo sapiens

<400> SEQUENCE: 266

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 267
<211> LENGTH: 22
<212> TYPE: PRT
<213> ORGANISM: Homo sapiens

<400> SEQUENCE: 267

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 268

-continued

```
<211> LENGTH: 22
<212> TYPE: PRT
<213> ORGANISM: Homo sapiens

<400> SEQUENCE: 268

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 269
<211> LENGTH: 22
<212> TYPE: PRT
<213> ORGANISM: Homo sapiens

<400> SEQUENCE: 269

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 270
<211> LENGTH: 22
<212> TYPE: PRT
<213> ORGANISM: Homo sapiens

<400> SEQUENCE: 270

Met Asp Met Arg Val Pro Ala Gln Leu Leu Gly Leu Leu Leu Leu Trp
1               5                   10                  15

Leu Pro Asp Thr Arg Cys
            20

<210> SEQ ID NO 271
<211> LENGTH: 22
<212> TYPE: PRT
<213> ORGANISM: Homo sapiens

<400> SEQUENCE: 271

Met Lys Lys Thr Ala Ile Ala Ile Ala Val Ala Leu Ala Gly Phe Ala
1               5                   10                  15

Thr Val Ala Gln Ala Ala
            20

<210> SEQ ID NO 272
<211> LENGTH: 20
<212> TYPE: PRT
<213> ORGANISM: Homo sapiens

<400> SEQUENCE: 272

Met Val Leu Gln Thr Gln Val Phe Ile Ser Leu Leu Leu Trp Ile Ser
1               5                   10                  15

Gly Ser Tyr Gly
            20

<210> SEQ ID NO 273
<211> LENGTH: 22
<212> TYPE: PRT
<213> ORGANISM: Homo sapiens

<400> SEQUENCE: 273

Met Glu Thr Pro Ala Gln Leu Leu Phe Leu Leu Leu Leu Trp Leu Pro
1               5                   10                  15
```

-continued

Val Ser Asp Thr Thr Gly
            20

<210> SEQ ID NO 274
<211> LENGTH: 21
<212> TYPE: PRT
<213> ORGANISM: Homo sapiens

<400> SEQUENCE: 274

Met Lys Gln Ser Thr Ile Ala Leu Ala Leu Leu Pro Leu Leu Phe Thr
1               5                   10                  15

Pro Val Thr Lys Ala
            20

<210> SEQ ID NO 275
<211> LENGTH: 23
<212> TYPE: PRT
<213> ORGANISM: Homo sapiens

<400> SEQUENCE: 275

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 276
<211> LENGTH: 22
<212> TYPE: PRT
<213> ORGANISM: Homo sapiens

<400> SEQUENCE: 276

Met Lys Lys Thr Ala Ile Ala Ile Ala Val Ala Leu Ala Gly Phe Ala
1               5                   10                  15

Thr Val Ala Gln Ala Ala
            20

<210> SEQ ID NO 277
<211> LENGTH: 8
<212> TYPE: PRT
<213> ORGANISM: Homo sapiens
<220> FEATURE:
<221> NAME/KEY: Xaa6
<222> LOCATION: (1)..(1)
<223> OTHER INFORMATION: Xaa6 is any one of Trp, Phe or Ile
<220> FEATURE:
<221> NAME/KEY: Xaa7
<222> LOCATION: (2)..(2)
<223> OTHER INFORMATION: Xaa7 is any one of Val, Ile or Leu
<220> FEATURE:
<221> NAME/KEY: Xaa8
<222> LOCATION: (3)..(3)
<223> OTHER INFORMATION: Xaa8 is Phe or Leu
<220> FEATURE:
<221> NAME/KEY: Xaa9
<222> LOCATION: (4)..(4)
<223> OTHER INFORMATION: Xaa9 is Leu or Val
<220> FEATURE:
<221> NAME/KEY: Xaa10
<222> LOCATION: (5)..(5)
<223> OTHER INFORMATION: Xaa10 is Val or Leu
<220> FEATURE:
<221> NAME/KEY: Xaa11
<222> LOCATION: (6)..(6)
<223> OTHER INFORMATION: Xaa11 is Ala
<220> FEATURE:
<221> NAME/KEY: Xaa12
<222> LOCATION: (7)..(7)
<223> OTHER INFORMATION: Xaa12 is any one of Leu, Ile or Ala
<220> FEATURE:

```
<221> NAME/KEY: Xaa13
<222> LOCATION: (8)..(8)
<223> OTHER INFORMATION: Xaa13 is any one of Phe, Leu, Pro or Ala

<400> SEQUENCE: 277

Xaa Xaa Xaa Xaa Xaa Xaa Xaa Xaa
1               5

<210> SEQ ID NO 278
<211> LENGTH: 6
<212> TYPE: PRT
<213> ORGANISM: Homo sapiens
<220> FEATURE:
<221> NAME/KEY: Xaa1
<222> LOCATION: (2)..(2)
<223> OTHER INFORMATION: Xaa1 is any one of Asp, Asn or Lys
<220> FEATURE:
<221> NAME/KEY: Xaa2
<222> LOCATION: (3)..(3)
<223> OTHER INFORMATION: Xaa2 is any one of Phe, Leu, His or Trp
<220> FEATURE:
<221> NAME/KEY: Xaa3
<222> LOCATION: (4)..(4)
<223> OTHER INFORMATION: Xaa3 is any one of Gly, Leu or Thr;
<220> FEATURE:
<221> NAME/KEY: Xaa4
<222> LOCATION: (5)..(5)
<223> OTHER INFORMATION: Xaa4 is Leu or Trp;
<220> FEATURE:
<221> NAME/KEY: Xaa5
<222> LOCATION: (6)..(6)
<223> OTHER INFORMATION: Xaa5 is any one of Ser, Arg or Phe

<400> SEQUENCE: 278

Met Xaa Xaa Xaa Xaa Xaa
1               5

<210> SEQ ID NO 279
<211> LENGTH: 6
<212> TYPE: PRT
<213> ORGANISM: Homo sapiens
<220> FEATURE:
<221> NAME/KEY: Xaa14
<222> LOCATION: (1)..(1)
<223> OTHER INFORMATION: Xaa14 is any one of Arg, Lys, Asp or Thr;
<220> FEATURE:
<221> NAME/KEY: Xaa15
<222> LOCATION: (2)..(2)
<223> OTHER INFORMATION: Xaa15 is Gly or Trp;
<220> FEATURE:
<221> NAME/KEY: Xaa16
<222> LOCATION: (3)..(3)
<223> OTHER INFORMATION: Xaa16 is Val or Ala;
<220> FEATURE:
<221> NAME/KEY: Xaa17
<222> LOCATION: (4)..(4)
<223> OTHER INFORMATION: Xaa17 is any one of Glu, Leu, or His
<220> FEATURE:
<221> NAME/KEY: Xaa18
<222> LOCATION: (5)..(5)
<223> OTHER INFORMATION: Xaa18 is Cys or Ser
<220> FEATURE:
<221> NAME/KEY: misc_feature
<222> LOCATION: (6)..(6)
<223> OTHER INFORMATION: Xaa can be any naturally occurring amino acid

<400> SEQUENCE: 279

Xaa Xaa Xaa Xaa Xaa Xaa
1               5

<210> SEQ ID NO 280
<211> LENGTH: 9
<212> TYPE: PRT
```

```
<213> ORGANISM: Homo sapiens
<220> FEATURE:
<221> NAME/KEY: misc_feature
<222> LOCATION: (1)..(9)
<223> OTHER INFORMATION: Xaa can be any naturally occurring amino acid

<400> SEQUENCE: 280

Xaa Xaa Xaa Xaa Xaa Xaa Xaa Xaa Xaa
1               5

<210> SEQ ID NO 281
<211> LENGTH: 6
<212> TYPE: PRT
<213> ORGANISM: Homo sapiens
<220> FEATURE:
<221> NAME/KEY: misc_feature
<222> LOCATION: (2)..(6)
<223> OTHER INFORMATION: Xaa can be any naturally occurring amino acid

<400> SEQUENCE: 281

Met Xaa Xaa Xaa Xaa Xaa
1               5

<210> SEQ ID NO 282
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Xaa can be any naturally occurring amino acid

<400> SEQUENCE: 282

Xaa Xaa Xaa Xaa Xaa Xaa Xaa
1               5

<210> SEQ ID NO 283
<211> LENGTH: 57
<212> TYPE: DNA
<213> ORGANISM: Homo sapiens

<400> SEQUENCE: 283
atggagttgg gactgagctg gattttcctt ttggctattt taaaaggtgt ccagtgt         57

<210> SEQ ID NO 284
<211> LENGTH: 57
<212> TYPE: DNA
<213> ORGANISM: Homo sapiens

<400> SEQUENCE: 284
atggaactgg ggctccgctg ggttttcctt gttgctattt tagaaggtgt ccagtgt         57

<210> SEQ ID NO 285
<211> LENGTH: 57
<212> TYPE: DNA
<213> ORGANISM: Homo sapiens

<400> SEQUENCE: 285
atgaaacacc tgtggttctt cctcctgctg gtggcagctc ccagatgggt cctgtcc         57

<210> SEQ ID NO 286
<211> LENGTH: 57
<212> TYPE: DNA
<213> ORGANISM: Homo sapiens

<400> SEQUENCE: 286
```

```
atggactgga cctggaggat cctcttcttg gtggcagcag caacaggtgc ccactcg      57
```

<210> SEQ ID NO 287
<211> LENGTH: 57
<212> TYPE: DNA
<213> ORGANISM: Homo sapiens

<400> SEQUENCE: 287

```
atggactgga cctggaggtt cctctttgtg gtggcagcag ctacaggtgt ccagtcc      57
```

<210> SEQ ID NO 288
<211> LENGTH: 57
<212> TYPE: DNA
<213> ORGANISM: Homo sapiens

<400> SEQUENCE: 288

```
atggagtttg ggctgagctg gcttttcctt gtggcgattc taaaaggtgt ccagtgt      57
```

<210> SEQ ID NO 289
<211> LENGTH: 57
<212> TYPE: DNA
<213> ORGANISM: Homo sapiens

<400> SEQUENCE: 289

```
atggagtttg ggctgagctg ggttttcctc gttgctcttt ttagaggtgt ccagtgt      57
```

<210> SEQ ID NO 290
<211> LENGTH: 78
<212> TYPE: DNA
<213> ORGANISM: Homo sapiens

<400> SEQUENCE: 290

```
atggacctcc tgcacaagaa catgaaacac ctgtggttct cctcctcct ggtggcagct    60 cccagatggg tgctgtcc                                                  78
```

<210> SEQ ID NO 291
<211> LENGTH: 66
<212> TYPE: DNA
<213> ORGANISM: Homo sapiens

<400> SEQUENCE: 291

```
atggacatga ggtccctgc tcagctcctg gggctcctgc tgctctggct ctcaggtgcc    60
agatgt                                                              66
```

<210> SEQ ID NO 292
<211> LENGTH: 66
<212> TYPE: DNA
<213> ORGANISM: Homo sapiens

<400> SEQUENCE: 292

```
atgaaatacc tattgcctac ggcagccgct ggattgttat tactcgcggc ccagccggcc    60
atggcc                                                              66
```

<210> SEQ ID NO 293
<211> LENGTH: 6
<212> TYPE: PRT
<213> ORGANISM: Homo sapiens

<400> SEQUENCE: 293

```
Met Glu Leu Gly Leu Ser
1               5
```

```
<210> SEQ ID NO 294
<211> LENGTH: 6
<212> TYPE: PRT
<213> ORGANISM: Homo sapiens

<400> SEQUENCE: 294

Met Glu Leu Gly Leu Arg
1               5

<210> SEQ ID NO 295
<211> LENGTH: 6
<212> TYPE: PRT
<213> ORGANISM: Homo sapiens

<400> SEQUENCE: 295

Met Lys His Leu Trp Phe
1               5

<210> SEQ ID NO 296
<211> LENGTH: 6
<212> TYPE: PRT
<213> ORGANISM: Homo sapiens

<400> SEQUENCE: 296

Met Asp Trp Thr Trp Arg
1               5

<210> SEQ ID NO 297
<211> LENGTH: 6
<212> TYPE: PRT
<213> ORGANISM: Homo sapiens

<400> SEQUENCE: 297

Met Glu Phe Gly Leu Ser
1               5

<210> SEQ ID NO 298
<211> LENGTH: 5
<212> TYPE: PRT
<213> ORGANISM: Homo sapiens

<400> SEQUENCE: 298

Lys Gly Val Gln Cys
1               5

<210> SEQ ID NO 299
<211> LENGTH: 5
<212> TYPE: PRT
<213> ORGANISM: Homo sapiens

<400> SEQUENCE: 299

Glu Gly Val Gln Cys
1               5

<210> SEQ ID NO 300
<211> LENGTH: 5
<212> TYPE: PRT
<213> ORGANISM: Homo sapiens

<400> SEQUENCE: 300

Arg Trp Val Leu Ser
1               5

<210> SEQ ID NO 301
```

```
<211> LENGTH: 5
<212> TYPE: PRT
<213> ORGANISM: Homo sapiens

<400> SEQUENCE: 301

Thr Gly Ala His Ser
1               5

<210> SEQ ID NO 302
<211> LENGTH: 5
<212> TYPE: PRT
<213> ORGANISM: Homo sapiens

<400> SEQUENCE: 302

Thr Gly Val Gln Ser
1               5

<210> SEQ ID NO 303
<211> LENGTH: 5
<212> TYPE: PRT
<213> ORGANISM: Homo sapiens

<400> SEQUENCE: 303

Arg Gly Val Gln Cys
1               5

<210> SEQ ID NO 304
<211> LENGTH: 8
<212> TYPE: PRT
<213> ORGANISM: Homo sapiens

<400> SEQUENCE: 304

Trp Ile Phe Leu Leu Ala Ile Leu
1               5

<210> SEQ ID NO 305
<211> LENGTH: 8
<212> TYPE: PRT
<213> ORGANISM: Homo sapiens

<400> SEQUENCE: 305

Trp Val Phe Leu Val Ala Ile Leu
1               5

<210> SEQ ID NO 306
<211> LENGTH: 8
<212> TYPE: PRT
<213> ORGANISM: Homo sapiens

<400> SEQUENCE: 306

Phe Leu Leu Leu Val Ala Ala Pro
1               5

<210> SEQ ID NO 307
<211> LENGTH: 8
<212> TYPE: PRT
<213> ORGANISM: Homo sapiens

<400> SEQUENCE: 307

Ile Leu Phe Leu Val Ala Ala Ala
1               5

<210> SEQ ID NO 308
<211> LENGTH: 8
<212> TYPE: PRT
```

```
<213> ORGANISM: Homo sapiens

<400> SEQUENCE: 308

Phe Leu Phe Val Val Ala Ala Ala
1               5

<210> SEQ ID NO 309
<211> LENGTH: 8
<212> TYPE: PRT
<213> ORGANISM: Homo sapiens

<400> SEQUENCE: 309

Trp Leu Phe Leu Val Ala Ile Leu
1               5

<210> SEQ ID NO 310
<211> LENGTH: 8
<212> TYPE: PRT
<213> ORGANISM: Homo sapiens

<400> SEQUENCE: 310

Trp Val Phe Leu Val Ala Leu Phe
1               5

<210> SEQ ID NO 311
<211> LENGTH: 6
<212> TYPE: PRT
<213> ORGANISM: Homo sapiens

<400> SEQUENCE: 311

Met Asp Met Arg Val Pro
1               5

<210> SEQ ID NO 312
<211> LENGTH: 6
<212> TYPE: PRT
<213> ORGANISM: Homo sapiens

<400> SEQUENCE: 312

Met Lys Tyr Leu Leu Pro
1               5

<210> SEQ ID NO 313
<211> LENGTH: 5
<212> TYPE: PRT
<213> ORGANISM: Homo sapiens

<400> SEQUENCE: 313

Ser Gly Ala Arg Cys
1               5

<210> SEQ ID NO 314
<211> LENGTH: 5
<212> TYPE: PRT
<213> ORGANISM: Homo sapiens

<400> SEQUENCE: 314

Gln Pro Ala Met Ala
1               5

<210> SEQ ID NO 315
<211> LENGTH: 11
<212> TYPE: PRT
<213> ORGANISM: Homo sapiens
```

```
<400> SEQUENCE: 315

Ala Gln Leu Leu Gly Leu Leu Leu Leu Trp Leu
1               5                   10

<210> SEQ ID NO 316
<211> LENGTH: 11
<212> TYPE: PRT
<213> ORGANISM: Homo sapiens

<400> SEQUENCE: 316

Thr Ala Ala Ala Gly Leu Leu Leu Leu Ala Ala
1               5                   10

<210> SEQ ID NO 317
<211> LENGTH: 22
<212> TYPE: PRT
<213> ORGANISM: Homo sapiens

<400> SEQUENCE: 317

Met Asp Phe Gln Val Gln Ile Ile Ser Phe Leu Leu Ile Ser Ala Ser
1               5                   10                  15

Val Ile Met Ser Arg Gly
            20

<210> SEQ ID NO 318
<211> LENGTH: 19
<212> TYPE: PRT
<213> ORGANISM: Homo sapiens

<400> SEQUENCE: 318

Met Gly Trp Ser Leu Ile Leu Leu Phe Leu Val Ala Val Ala Thr Arg
1               5                   10                  15

Val Leu Ser

<210> SEQ ID NO 319
<211> LENGTH: 19
<212> TYPE: PRT
<213> ORGANISM: Homo sapiens
<220> FEATURE:
<221> NAME/KEY: MISC_FEATURE
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Trp or Leu
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Xaa is Ser or Cys

<400> SEQUENCE: 319

Met Xaa Xaa Xaa Xaa Xaa Xaa Leu Phe Leu Val Ala Ala Xaa Xaa Gly
1               5                   10                  15

Val Gln Xaa

<210> SEQ ID NO 320
<211> LENGTH: 20
```

```
<212> TYPE: PRT
<213> ORGANISM: Homo sapiens

<400> SEQUENCE: 320

Arg Cys Asp Ile Gln Met Thr Gln Ser Pro Ser Ser Leu Ser Ala Ser
1               5                   10                  15

Val Gly Asp Arg
            20

<210> SEQ ID NO 321
<211> LENGTH: 21
<212> TYPE: PRT
<213> ORGANISM: Homo sapiens

<400> SEQUENCE: 321

Gln Cys Glu Val Gln Leu Val Glu Ser Gly Gly Gly Leu Val Gln Pro
1               5                   10                  15

Gly Gly Ser Leu Arg
            20

<210> SEQ ID NO 322
<211> LENGTH: 20
<212> TYPE: PRT
<213> ORGANISM: Homo sapiens

<400> SEQUENCE: 322

Arg Cys Asp Ile Gln Met Thr Gln Ser Pro Ser Ser Leu Ser Ala Ser
1               5                   10                  15

Val Gly Asp Arg
            20

<210> SEQ ID NO 323
<211> LENGTH: 21
<212> TYPE: PRT
<213> ORGANISM: Homo sapiens

<400> SEQUENCE: 323

Gln Ser Glu Val Gln Leu Val Glu Ser Gly Gly Gly Leu Val Gln Pro
1               5                   10                  15

Gly Gly Ser Leu Arg
            20

<210> SEQ ID NO 324
<211> LENGTH: 20
<212> TYPE: PRT
<213> ORGANISM: Homo sapiens

<400> SEQUENCE: 324

Arg Cys Asp Ile Gln Met Thr Gln Ser Pro Ser Ser Leu Ser Ala Ser
1               5                   10                  15

Val Gly Asp Arg
            20

<210> SEQ ID NO 325
<211> LENGTH: 18
<212> TYPE: PRT
<213> ORGANISM: Homo sapiens

<400> SEQUENCE: 325

Gln Cys Glu Val Gln Leu Val Glu Ser Gly Gly Gly Leu Val Gln Pro
1               5                   10                  15

Gly Arg
```

<210> SEQ ID NO 326
<211> LENGTH: 20
<212> TYPE: PRT
<213> ORGANISM: Homo sapiens

<400> SEQUENCE: 326

Arg Cys Gln Ile Val Leu Ser Gln Ser Pro Ala Ile Leu Ser Ala Ser
1               5                   10                  15

Pro Gly Glu Lys
            20

<210> SEQ ID NO 327
<211> LENGTH: 21
<212> TYPE: PRT
<213> ORGANISM: Homo sapiens

<400> SEQUENCE: 327

Gln Cys Gln Val Gln Leu Gln Gln Pro Gly Ala Glu Leu Val Lys Pro
1               5                   10                  15

Gly Ala Ser Val Lys
            20

<210> SEQ ID NO 328
<211> LENGTH: 20
<212> TYPE: PRT
<213> ORGANISM: Homo sapiens

<400> SEQUENCE: 328

Met Ala Gln Ile Val Leu Ser Gln Ser Pro Ala Ile Leu Ser Ala Ser
1               5                   10                  15

Pro Gly Glu Lys
            20

<210> SEQ ID NO 329
<211> LENGTH: 21
<212> TYPE: PRT
<213> ORGANISM: Homo sapiens

<400> SEQUENCE: 329

Leu Ser Gln Val Gln Leu Gln Gln Pro Gly Ala Glu Leu Val Lys Pro
1               5                   10                  15

Gly Ala Ser Val Lys
            20

<210> SEQ ID NO 330
<211> LENGTH: 20
<212> TYPE: PRT
<213> ORGANISM: Homo sapiens

<400> SEQUENCE: 330

Arg Cys Asp Ile Leu Leu Thr Gln Ser Pro Ala Ile Leu Ser Val Ser
1               5                   10                  15

Pro Gly Glu Arg
            20

<210> SEQ ID NO 331
<211> LENGTH: 21
<212> TYPE: PRT

<400> SEQUENCE: 331

```
Gln Cys Glu Val Lys Leu Glu Glu Ser Gly Gly Gly Leu Val Gln Pro
1               5                   10                  15

Gly Gly Ser Met Lys
            20
```

OPTIMISED HEAVY CHAIN AND LIGHT CHAIN SIGNAL PEPTIDES FOR THE PRODUCTION OF RECOMBINANT ANTIBODY THERAPEUTICS

CROSS-REFERENCE TO RELATED APPLICATIONS

This application is a U.S. national stage application filed under 35 U.S.C. § 371 from International Application Serial No. PCT/SG2013/000360, which was filed Aug. 21, 2013, and published as WO 2014/058389 on Apr. 17, 2014, and which claims the benefit of priority of SG provisional application No. 201207629-5, filed Oct. 12, 2012, which applications and publication are incorporated by reference as if reproduced herein and made a part hereof in their entirety, and the benefit of priority of each of which is claimed herein.

FIELD OF THE INVENTION

The invention relates to the field of biotechnology and molecular biology. The invention relates to an antibody of interest comprising an optimised selection of signal peptides and their use for enhanced antibody secretion from cells. In particular, embodiments of the present invention relate to methods of determining signal peptide for enhancing secretion of an antibody as well as other related antibodies, compositions and methods.

BACKGROUND OF THE INVENTION

Recombinant protein expression represents a large portion of the production of proteins used in molecular biology, agronomy, veterinary science or medicine. For example, recombinant therapeutic antibodies represent a large percentage of biopharmaceuticals (i.e. medical drugs produced using biotechnology) produced.

Protein signal sequences, also called topogenic signals or signal peptides, play a central role in the targeting and translocation of nearly all secreted proteins and many integral membrane proteins in both prokaryotes and eukaryotes. The signal peptides from various proteins generally consist of three structurally, and possibly functionally distinct, regions: (1) an amino terminal (N-terminal) positively charged N-region (or N-domain), (2) a central hydrophobic H-region (or H-domain), and (3) a neutral but polar carboxy terminal (C-region or C-domain).

The determination of protein signal sequences is important to improve excretion and secretion of antibodies produced using an expression system such as bacteria, plants, and animals to produce effective drugs (especially therapeutic proteins). By adding a specific tag to an antibody of interest, it is possible to improve the antibody excretion or secretion in the extracellular environment. In this manner, the antibody is easier to harvest and is less likely to be degraded or to induce toxicity of the expression system by accumulating in the intracellular environment of the expression system. Thus, an antibody may be expressed as a fusion protein comprising a preferred N-terminal sequence fused to a mature sequence of the heavy chain or the light chain of an antibody.

To effectively use this technique, the signal peptides must be identified. However, the amino acid sequence of most recombinant therapeutic antibodies disclosed in publicly available databases does not include the sequences of the signal peptides. Furthermore, the signal peptide information required for production in mammalian cell culture is also absent in the case of monoclonal antibodies isolated through methods such as phage display.

Rituxan is the only antibody for which heavy and light chain signal peptide sequence information is available in public database. However, the availability of the information does not entail that the original signal peptide is optimized for the secretion of the antibody in the desired host cell selected for production.

Another issue associated with production of recombinant antibodies comprising a signal peptide is the cleavage heterogeneity. Cleavage heterogeneity may arise from nonspecific cleavage of a signal peptide by a signal peptidase. As cleavage of the signal peptide occurs within the variable region in the N-terminus of both the heavy and light chains, non-specific cleavage may affect antigen recognition.

Recombinant IgG production may also be affected by glycan heterogeneity that is present at the N-glycosylation site of the $C_H2$ constant domain of the heavy chains. One recent study explored an LC/MS with a column-switching system to rapidly evaluate glycan heterogeneity.

Thus, there is a need to provide further signal peptides to create recombinant antibodies that are efficiently secreted and produced in expression systems.

SUMMARY OF THE INVENTION

Described below are antibodies of interest with a light chain and heavy chain fused to signal peptides to enhance secretion of the antibody during production and methods of determining a signal peptide for enhancing secretion of an antibody of interest.

Thus, in a first aspect, there is provided an antibody of interest comprising a heavy chain signal peptide, wherein the heavy chain signal peptide comprises a N-domain, a H-domain and a C-domain, wherein the heavy chain signal peptide is bound to the antibody via the C-terminal end of the C-domain; wherein the H-domain comprises an amino acid sequence of formula (I):

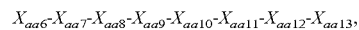

wherein $X_{aa6}$ is any one of Trp, Phe or Ile; $X_{aa7}$ is any one of Val, Ile or Leu; $X_{aa8}$ is Phe or Leu; $X_{aa9}$ is Leu or Val; $X_{aa10}$ is Val or Leu; $X_{aa11}$ is Ala; $X_{aa12}$ is any one of Leu, Ile or Ala; $X_{aa13}$ is any one of Phe, Leu, Pro or Ala; and wherein the amino acid sequence of formula (I) has optionally one or two mutations; provided that an antibody showing the lowest secretion is excluded, wherein the lowest secretion is determined by a) fusing polynucleotides encoding the heavy chain of the antibody of interest to a polynucleotide encoding the heavy chain signal peptide as defined herein, to obtain different combinations of heavy chain signal peptides and antibody of interest; b) creating at least one expression vector comprising the polynucleotides defined under a); and c) quantifying secretion of the antibody of interest encoded by the vector referred to under b) after transfection into an expression system to determine the antibody with the lowest secretion.

In a second aspect, there is provided an antibody of interest comprising a light chain signal peptide, wherein the light chain signal peptide comprises an amino acid sequence of formula (IV):

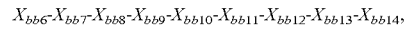

wherein $X_{bb6}$ is Ala or Thr; $X_{bb7}$ is Gln or Ala; $X_{bb8}$ is Leu or Ala; $X_{bb9}$ is Leu or Ala; $X_{bb10}$ is Gly; $X_{bb11}$ to $X_{bb14}$ is Leu; or wherein the amino acid sequence of the formula (IV) has one or two mutations; provided that an antibody showing the lowest secretion is excluded, wherein the lowest secretion is determined by a) fusing polynucleotides encoding the light chain of the antibody of interest to a polynucleotide encoding the light chain signal peptide as defined herein to obtain different combinations of light chain signal peptides and antibody of interest; b) creating at least one expression vector comprising the polynucleotides defined under a); and c) quantifying secretion of the antibody of interest encoded by the vector referred to under b) after transfection into an expression system to determine the antibody with the lowest secretion.

In a third aspect, there is provided a polynucleotide encoding the antibody as described herein.

In a fourth aspect, there is provided a vector comprising the polynucleotide as defined above.

In a fifth aspect there is provided a host cell comprising the nucleotide as described hereinbefore and/or the vector as described hereinbefore.

In a sixth aspect, there is provided a hybridoma cell line capable of producing the antibody as described above.

In a seventh aspect, there is provided an amino acid sequence comprising the amino acid sequence for trastuzumab (Herceptin, CAS number 180288-69-1); a heavy chain signal peptide of SEQ ID NO: 1 fused to the heavy chain amino acid sequence of trastuzumab; and a light chain signal peptide of SEQ ID NO: 2 fused to the light chain amino acid sequence of trastuzumab.

In an eight aspect, there is provided an amino acid sequence comprising the amino acid sequence for bevacizumab (Avastin, CAS number 216974-75-3); a heavy chain signal peptide of SEQ ID NO: 3 fused to the heavy chain amino acid sequence of bevacizumab; and a light chain signal peptide of SEQ ID NO: 5 fused to the light chain amino acid sequence of bevacizumab.

In a ninth aspect, there is provided an amino acid sequence comprising the amino acid sequence for infliximab (Remicade, CAS number 170277-31-3); a heavy chain signal peptide of SEQ ID NO: 3 fused to the heavy chain amino acid sequence of infliximab; and a light chain signal peptide of SEQ ID NO: 4 fused to the light chain amino acid sequence of infliximab.

In a tenth aspect, there is provided an amino acid sequence comprising the amino acid sequence for rituximab (Rituxan, CAS number 174722-31-7); a heavy chain signal peptide of SEQ ID NO: 3 fused to the heavy chain amino acid sequence of rituximab; and a light chain signal peptide of SEQ ID NO: 4 fused to the light chain amino acid sequence of rituximab.

In an eleventh aspect, there is provided an amino acid sequence comprising the amino acid sequence for adalimumab (Humira, CAS number 331731-18-1); a heavy chain signal peptide of SEQ ID NO: 3 fused to the heavy chain amino acid sequence of adalimumab; and a light chain signal peptide of SEQ ID NO: 5 fused to the light chain amino acid sequence of adalimumab.

In a twelfth aspect, there is provided a nucleotide encoding an antibody as described above.

In a thirteenth aspect, there is provided a polynucleotide sequence encoding the amino acid sequence as described herein.

In a fourteenth aspect, there is provided a vector comprising a polynucleotide sequence as described herein.

BRIEF DESCRIPTION OF THE DRAWINGS

The invention will be better understood with reference to the detailed description when considered in conjunction with the non-limiting examples and the accompanying drawings, in which:

FIG. 1 C to F is an enlargement of the dendogram obtained in FIG. 1 A showing the amino acid sequence of the signal peptides present in each of the created clusters H1 to H8, representative of the Ig heavy chain signal peptides. The selected amino acid sequence of SEQ ID: 1, 3, and 5 to 10 is highlighted for each one of the clusters H1 to H8. FIG. 1 G is an enlargement of the dendogram shown in FIG. 1 B showing the specific amino acid sequences of each of the 57 human kappa chains that were used to create the database. The specific amino acid sequence of the two clusters, L1 and L2, having the amino acid sequence of SEQ ID NO: 2 and 4, are highlighted.

FIGS. 3 A and C: Ig ELISA results were plotted showing the monoclonal antibody titer (in ng/ml) with eight different heavy chain signal peptides and two different light chain signal peptides. FIG. 3A shows results when heavy chains were paired with light chain signal peptide 1 (L1), while FIG. 3C shows results when heavy chains were paired with light chain signal peptide 2 (L2). FIGS. 3 B and D: The efficiency of the heavy chain signal peptides in each antibody is shown relative to heavy chain signal peptide 1 (H1), which is set to 1. FIG. 3B shows results when heavy chains were paired with light chain signal peptide 1 (L1), while FIG. 3D shows results when heavy chains were paired with light chain signal peptide 2 (L2). Mean fluorescence intensity of GFP was used to normalize variations due to difference in transfection efficiency. Herceptin is efficiently secreted with several different signal peptides. The combination that had the highest secretion when normalized as indicated herein is H5/L1, whereas H7 exhibited the best titre for Herceptin when paired with L2. The values were obtained following normalization with the GFP values as shown in FIGS. 3A and C to account for transfection efficiency variations among the different experiments.

FIGS. 4A and C: Ig ELISA results. FIGS. 4B and D: relative productivity normalized to H1. The best signal peptides combination for Avastin is H7/L1.

FIGS. 5 B and D: relative productivity normalized to H1. The heavy chain signal peptide that gave the highest secretion and expression rate when fused to the heavy chain of Remicade is H7 either when used in combination when L1 or L2 light chain signal peptide fused to the light chain of remicade.

FIGS. 6 A and B, light chain with signal peptide 1 was used. FIGS. 6 C and D light chain with signal peptide 2 was used. The best signal peptide combinations for Rituxan are the heavy chain signal peptide H7 and either L1 or L2.

FIGS. 7A and C: Ig ELISA results. Bottom panel: relative productivity normalized to H1. A and B, light chain with signal peptide 1 was used. FIGS. 7C and D, light chain with signal peptide 2 was used. Best signal peptides combination for Humira is H7/L1.

For Herceptin, the best pair of signal peptides was H5/L1. For Avastin and Humira, the best pair was H7/L1 while for Remicade and Rituxan the best pair was H7/L2. Mean fluorescence intensity of GFP was used to normalize the transfection efficiency.

Figure 9:
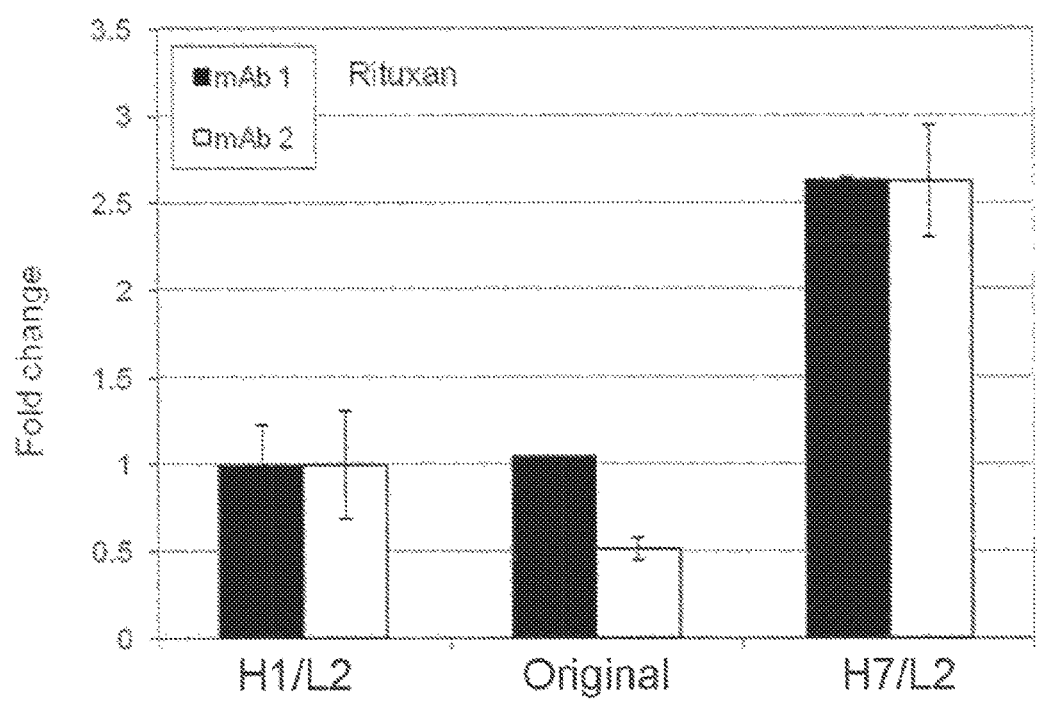

FIG. 9 is a bar graph representative of the efficiency of the optimized signal peptides in the secretion of Rituxan. FIG. 9 is a comparison between the original (that is the signal peptide present in public database) and the optimized signal peptide pairs for Rituxan, relative to the control pair H1/L2, which is set to 1. The relative efficiency of the optimized signal peptides for Rituxan (H7/L2) are more than twofold that of the original signal peptides.

Figures 2, 10:
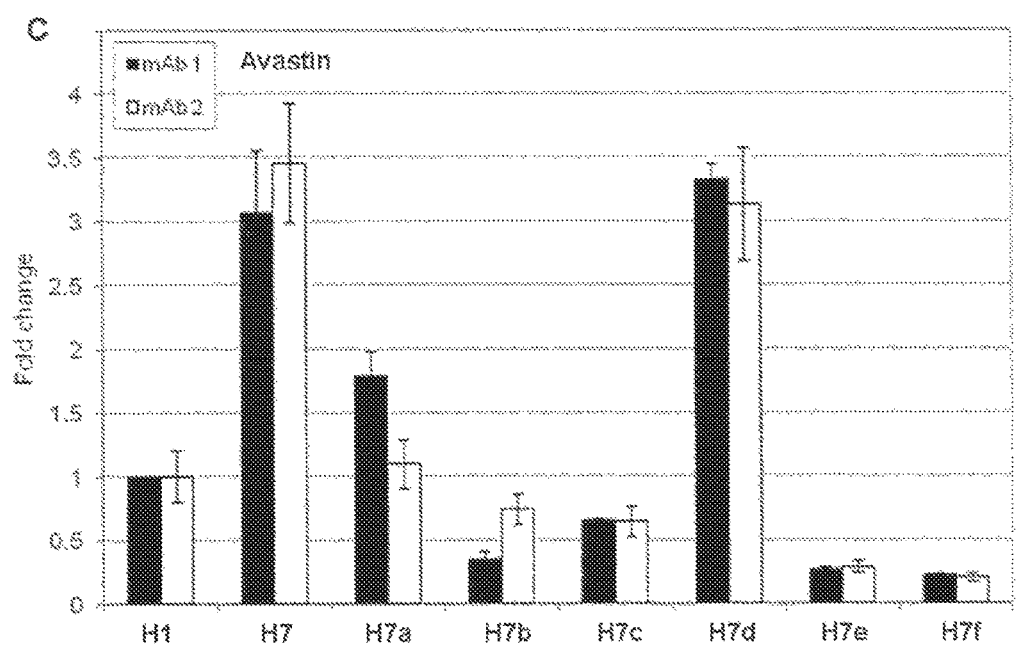

FIG. 10 represents a sequence alignment depicting the consensus sequence between the heavy chain signal peptides selected from the clusters H1 to H8, as described herein, (FIG. 10A) and the amino acid substitution of H7 signal peptide of the Avastin heavy chain (FIG. 10B). The N-domain, H-domain and C-domain are indicated below the consensus sequence and the number of amino acid within each domain is given above. Amino acid substitution mutations were performed on the H7 signal peptide to monitor the impact of such mutation on the secretion of Avastin heavy chain. For Avastin heavy chain, H7 is the signal peptide that provides the highest secretion efficiency. (A): A sequence comparison of all heavy chain signal peptide with H7 reveals several highly conserved amino acid residues: M*WLFLVAA*GVQS. (B): Six hybrid constructs (H7a to H7f) were generated, each with amino acid substitution(s) within the conserved sites to study their impact on Avastin secretion. (C): FIG. 10C is a histogram plot demonstrating the impact of amino acid substitutions in the H7 signal peptide fused to the heavy chain of Avastin on the secretion of the recombinant heavy chain. Only C to S mutation (H7d) did not significantly affect the expression level of Avastin. All other mutations resulted in decreased secretion of Avastin. H1 was included in the experiment as a control to normalize the results.

Figure 11:
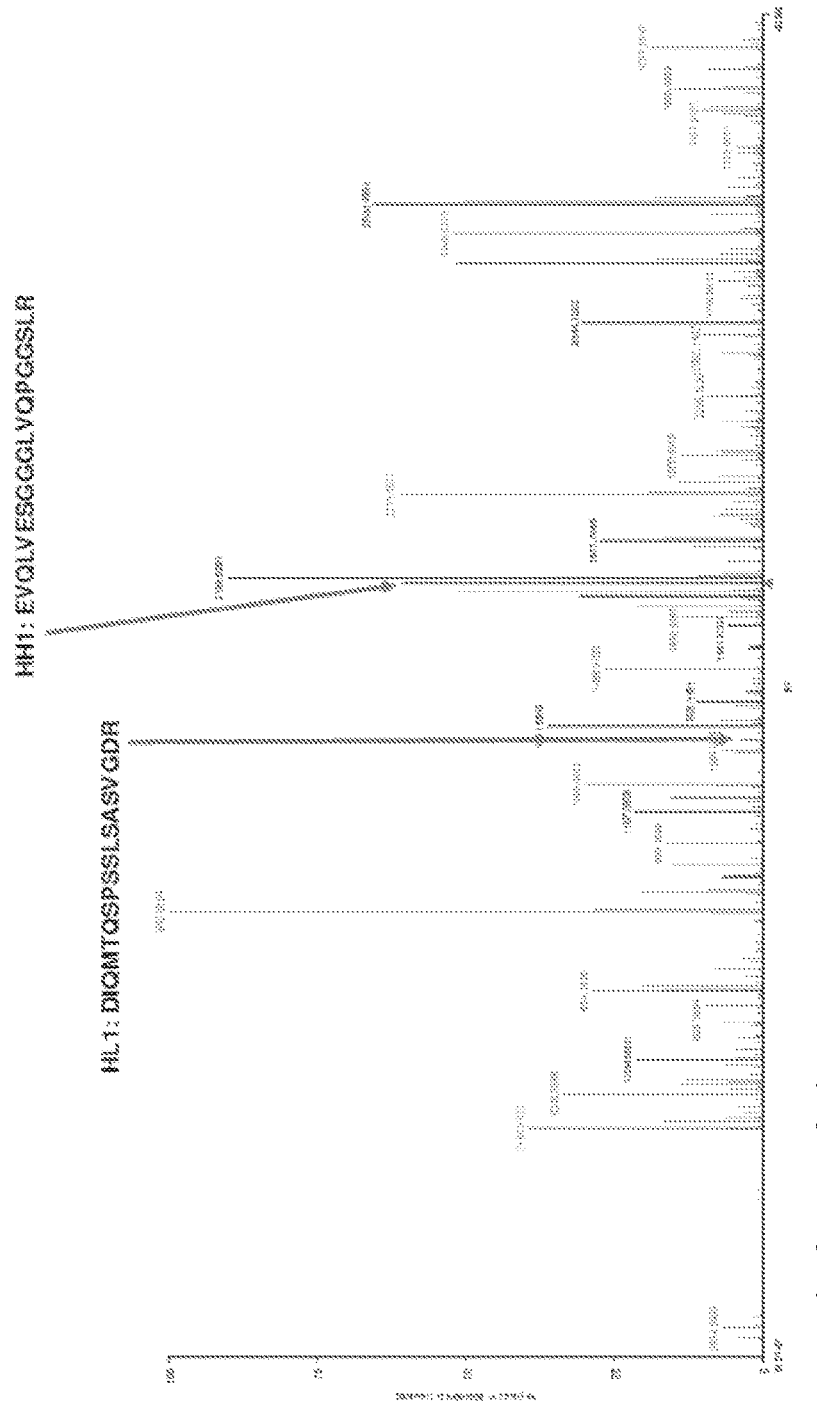

FIG. 11 depicts a mass spectrum representing the relative abundance versus the mass-to-charge ratio plot of Herceptin produced using recombinant signal peptide-heavy and light chain Herceptin antibodies. $MS^2$ fragment ions were generated from Herceptin using the LTQ Orbitrap Velos mass spectrometer. The peaks corresponding to the heavy chain and light chain N-terminal fragments, are indicated by the arrows. The amino acid sequences of the fragments are in bold type.

Figure 12:
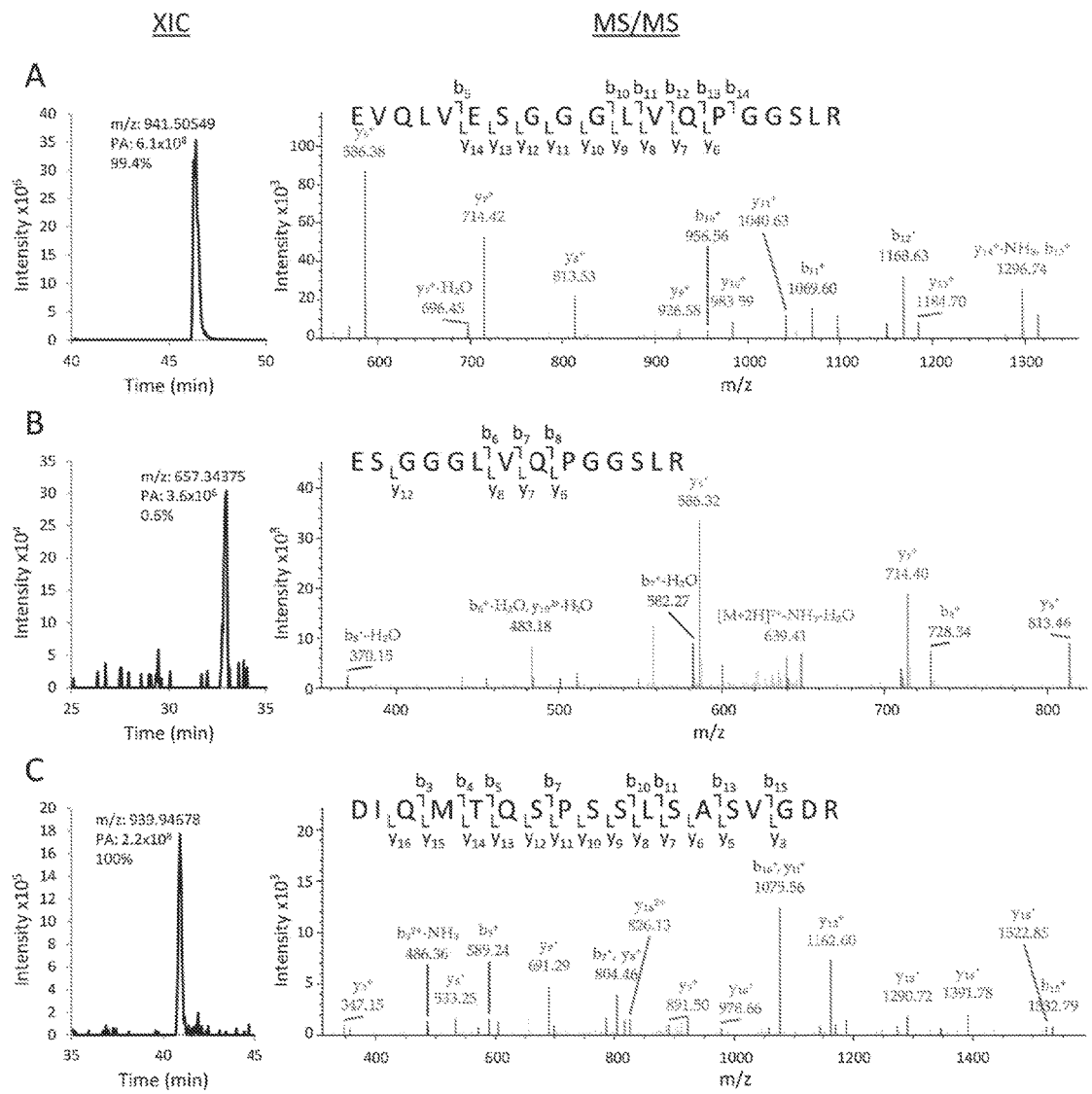

FIG. 12 represents a mass spectrum of recombinant Avastin. $MS^2$ fragment ions were generated from Avastin using the LTQ Orbitrap Velos mass spectrometer. The peaks corresponding to the heavy chain and light chain N-terminal fragments, are indicated by the arrows. The amino acid sequences of the fragments are in bold type. Extracted ion chromatogram (XIC) peaks and MS/MS fragmentation spectra matching to b- and y-ions series of (A) heavy chain N-terminal peptide, (B) erroneously processed heavy chain N-terminal peptide resulting from an alternative cleavage site 5 residues downstream of expected cleavage site, and (C) light chain N-terminal peptide. Mass/charge ratio (m/z) of each N-terminal peptide, peak area (PA) and its percentage representation relative to total N-terminal peptides detected for corresponding heavy or light chain polypeptides are shown in the XIC spectra.

Figure 13:
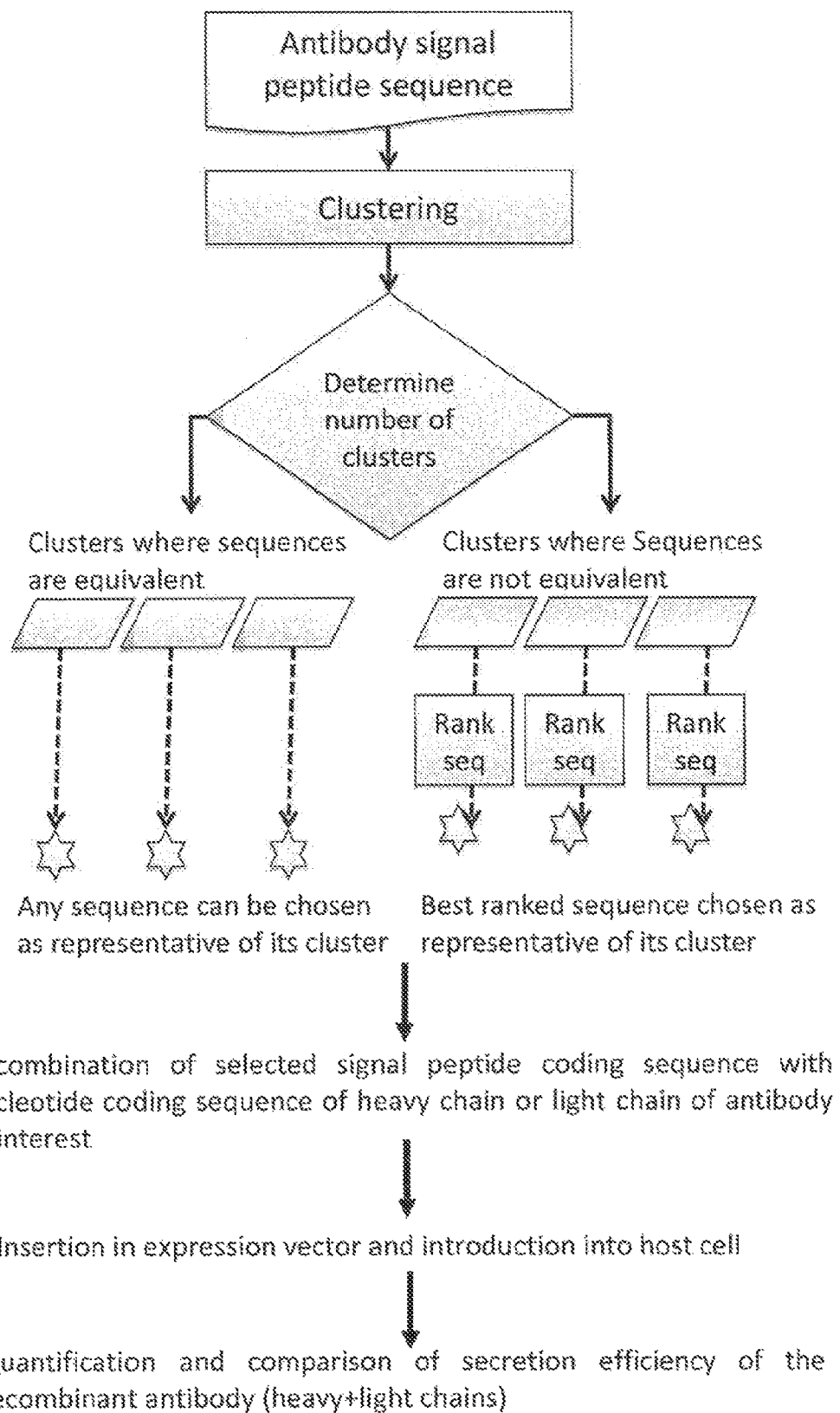

FIG. 13 is a representative diagram summarizing the method of determining the optimal signal peptide for enhancing antibody secretion.

DETAILED DESCRIPTION OF THE PRESENT INVENTION

Before the present methods, antibodies, nucleotides, amino acid sequences and uses thereof are described, it is to be understood that this invention is not limited to particular methods, antibodies, nucleotides, amino acid sequences, uses and experimental conditions described, as such methods, antibodies, nucleotides, amino acid sequences, uses and conditions may vary. It is also to be understood that the terminology used herein is for purposes of describing particular embodiments only, and is not intended to be limiting, since the scope of the present invention will be limited only by the appended claims.

Unless otherwise defined, all technical and scientific terms used herein have the same meaning as commonly understood by one of ordinary skill in the art, to which this invention belongs. Any methods and materials similar or equivalent to those described herein can be used in the practice or testing of the invention, as it will be understood that modifications and variations are encompassed within the spirit and scope of the instant disclosure.

The mechanism by which secreted proteins are translocated into the lumen of endoplasmic reticulum (ER, in eukaryotes) or through the plasma membrane (in prokaryotes) is universally conserved. In eukaryotes, this process occurs in the cytosol and involves recognition of the signal peptide in the nascent polypeptide chain by the signal recognition particle (SRP) as it emerges from the ribosome (ribosome-nascent chain, or RNC), causing elongation arrest. This SRP-RNC complex then binds to the membrane-anchored SRP-receptor (SR) in the ER, where GTP-dependent mechanism delivers the RNC to a membrane-bound Sec61 translocon which allows translocation of the growing polypeptide chain into the lumen of the ER. After crossing the translocon, the signal peptide is cleaved off by a signal peptidase.

Almost all secreted proteins have a signal peptide sequence, generally consisting of 20 to 30 amino acid residues beginning within 10 residues of the N-terminus, with a 10- to 15-residue long hydrophobic core. A hydrophilic stretch precedes this sequence, while a more polar stretch follows it up to the cleavage site. Signal sequence preferentially though weakly, binds in an α-helical confirmation to the hydrophobic groove in SRP in a 4-4 'ridges-into-grooves' packing, with the ribosome reinforcing this complex formation. The hydrophobic residues form a binding site that is critical for its interaction with the SRP, the translocon and the signal peptidase. Therefore, the exact sequence of the signal peptide may affect the efficiency of a protein to cross the ER membrane. Individual signal peptide sequences show little discernable primary sequence similarities and sequence variations can be considerable. As a result, it is challenging to anticipate, with any assurance, which amino acid sequence can serve as a signal peptide to achieve enhanced expression and secretion of recombinant antibodies in either prokaryotes or eukaryotes.

Recombinant therapeutic antibodies represent a large percentage of biopharmaceuticals produced. Advances in the manufacturing of such antibodies have been documented and are well-known in the art. The heavy chain of human IgG usually has a 19-amino acid signal peptide while the human kappa light chain contains a 22-amino acid signal peptide.

As described above, the expression of recombinant antibodies using expression systems requires the identification of optimized signal peptides to enhance efficacy of secretion of the heavy and light chain of the antibody.

Accordingly, it is an object of the present invention to identify and determine secretory signal peptides that enhance secretion and/or excretion of the heavy and light chain of antibodies when fused to their respective sequences. The present inventors have successfully designed a method to determine such optimized signal peptides in a protein expression system, while maintaining the activity and specificity of the antibody by providing homogenous cleavage at the proper cleavage site.

Therefore, the present invention provides a method of determining a signal peptide for enhancing secretion of an antibody of interest. The method may comprise the step of creating a database using publicly available amino acid sequence information of signal peptides associated with the heavy chain and the light chain of antibodies.

As defined herein the term "signal peptides" (SPs; also referred to as leader peptide, targeting signal, signal sequence, transit peptide or localization signal) are sequence motifs targeting proteins for translocation across the endoplasmic reticulum membrane. SPs are found at the amino terminus of nascent proteins, and function by prompting the transport mechanism within the cell to bring the proteins to their specific destination within the cell, or outside the cell if the proteins are to be secreted. If secreted in the extracellular environment, it may be specified that the SPs are secretory signal peptides. Thus, antibodies, which are naturally secreted like many other proteins, require a secretory signal peptide to function as sorting signals. In one example, the signal peptide as described herein may comprise 10, 11, 12, 13, 14, 15, 16, 17, 18, 19, 20, 21, 22, 23, 24, 24, 25, 26, 27, 28, 29, 30, 31, 32, 33, 34, 35, 36, 37, 38, 39, or 40 amino acids. In a further example, the sequence of the signal peptide as disclosed herein has about 10 to about 40 amino acids. In yet another example, the sequence of the signal peptide, as disclosed herein, has about 15 to about 35 amino acids. In another example, the sequence of the signal peptide as disclosed herein has about 18 to about 25 amino acids.

As described herein, the term "antibody" is used in the broadest sense and specifically covers monoclonal antibodies (including full length monoclonal antibodies), polyclonal antibodies, monospecific antibodies, multispecific antibodies (e.g., bispecific antibodies), and antibody fragments as long as they still exhibit the desired biological activity. The term "monoclonal antibody" refers to an antibody composition having a homogenous (essentially identical) antibody population. The term is not limited regarding the species (e.g., human, murine, mouse, or cat) or the source of the antibody, nor is it limited by the manner in which it is made. For example, the term includes monoclonal antibodies produced by a methodology other than hybridoma which results in monoclonal antibodies no matter how it is subcategorized, e.g., hybrid, altered, chimeric, or humanized. Further, the term includes variants that naturally arise during the production of monoclonal antibodies. The term includes whole immunoglobulins. The term "humanized antibody", as used herein, refers to an engineered antibody that typically comprises the variable region of a non-human (e.g., murine) antibody, i.e. a chimeric antibody, or at least the complementarity determining regions (CDRs) thereof, and the remaining immunoglobulin portions derived from a human antibody. Procedures for the production of chimeric antibodies and further engineered monoclonal antibodies include those described in the art. Such humanized antibodies may be prepared by known techniques and offer the advantage of reduced immunogenicity when the antibodies are administered to humans.

Antibodies of the present invention can include at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$).

For example the signal peptides of antibodies may be the signal peptides of the heavy chains of antibodies and the light chain of antibodies. The isotype of the antibody may comprise, but is not limited, to IgG, IgM, IgD, IgA and IgE. Thus, the heavy chain may comprise, but is not limited to, gamma, mu, delta, alpha and epsilon heavy chains, whereas the light chain may be a kappa or a lambda light chain. The antibody may be a mammalian antibody. The antibody may comprise, but is not limited to a human, a murine (rat and mice), an avian, a porcine, an equine, a bovine and a primate antibody.

Once the database had been created, the present inventors clustered the amino acid sequence based on similarity of the sequences. By "clustering" it is meant the task of grouping a set of sequences in such a way that sequences in the same group (called cluster) are more similar (in some sense or another) to each other than to those in other groups (clusters). To achieve clustering a number of algorithm are available depending on the task to be achieved. In one embodiment, examples of clustering may comprise, but are not limited, to hierarchical clustering, centroid-based clustering, distribution-based clustering, density-based clustering and seed-based clustering. In a further example, the hierarchical clustering used in the disclosure may comprise an agglomerative clustering or a divisive clustering. Clustering methods specifically directed at primary sequence analysis are well known in the art and are commercially or publicly available.

For example, the present inventors tested a clustering algorithm referred to as Neighbor Joining with uncorrected ("p"), wherein the distance between pairwise sequence alignments is treated as the percentage number of residue positions at which the sequences differ. This Neighbor Joining method is a type of agglomerative hierarchical clustering method, which is a bottom-up clustering method for creating phonetic trees.

By clustering the signal peptide sequence present in the database, the inventors were able to create two groups of clusters. One group of clusters is related to the amino acid sequence information of signal peptides of the heavy chain of antibodies; the other group is related to the amino acid sequence information of signal peptides of the light chain of antibodies.

The number of clusters that is created will depend, for example, on the number of signal sequences present in the database, the experimental facilities (that is factors like the number of sequences that may be tested by the skilled artisan, the budget, and time allocated to testing), the similarity between the amino acid sequences of the signal peptides in the database and the number of identical sequences in the database. In case most amino acid sequences are identical then the number of clusters will be reduced. Conversely, the less similarity between the sequences in a database, the higher the number of clusters that will be created.

Where the number of clusters created is at least three clusters, clusters may comprise at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 22%, at least about 25%, at least about 30%, at least about 40%, at least about 50% or at least about 60% of the total number of signal peptides sequences present in the database created based on publicly available information.

For example, based on a database comprising amino acid sequence information for 173 Ig heavy chain human signal peptides, the inventors created eight clusters, numbered H1 to H8 comprising between 16 and 30 signal peptide sequences, whereas based on a database comprising the signal peptide sequences from 62 human kappa chains, two clusters were created. These two clusters are represented for example, in FIG. 1 of the drawings.

Figures 1, 1A:
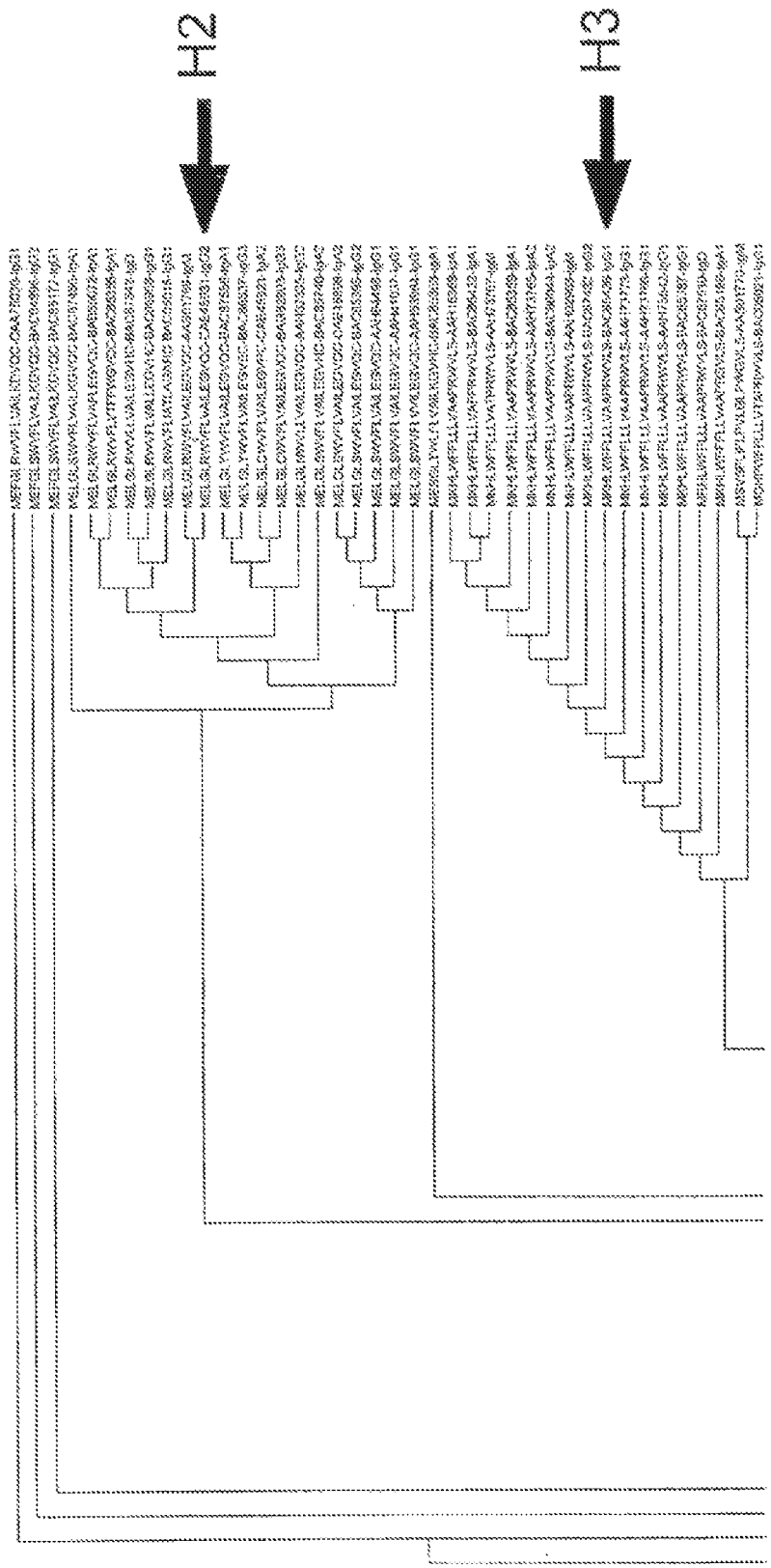
FIG. 1 is a hierarchical clustering dendogram of signal peptides using agglomerative nesting to search for sequence similarity in (A) heavy chain signal peptides from a database of 173 human Ig heavy chains and (B) kappa (κ) light chain signal peptides from a database of 62 human kappa chains.
Figures 1, 1A, 2, 3:
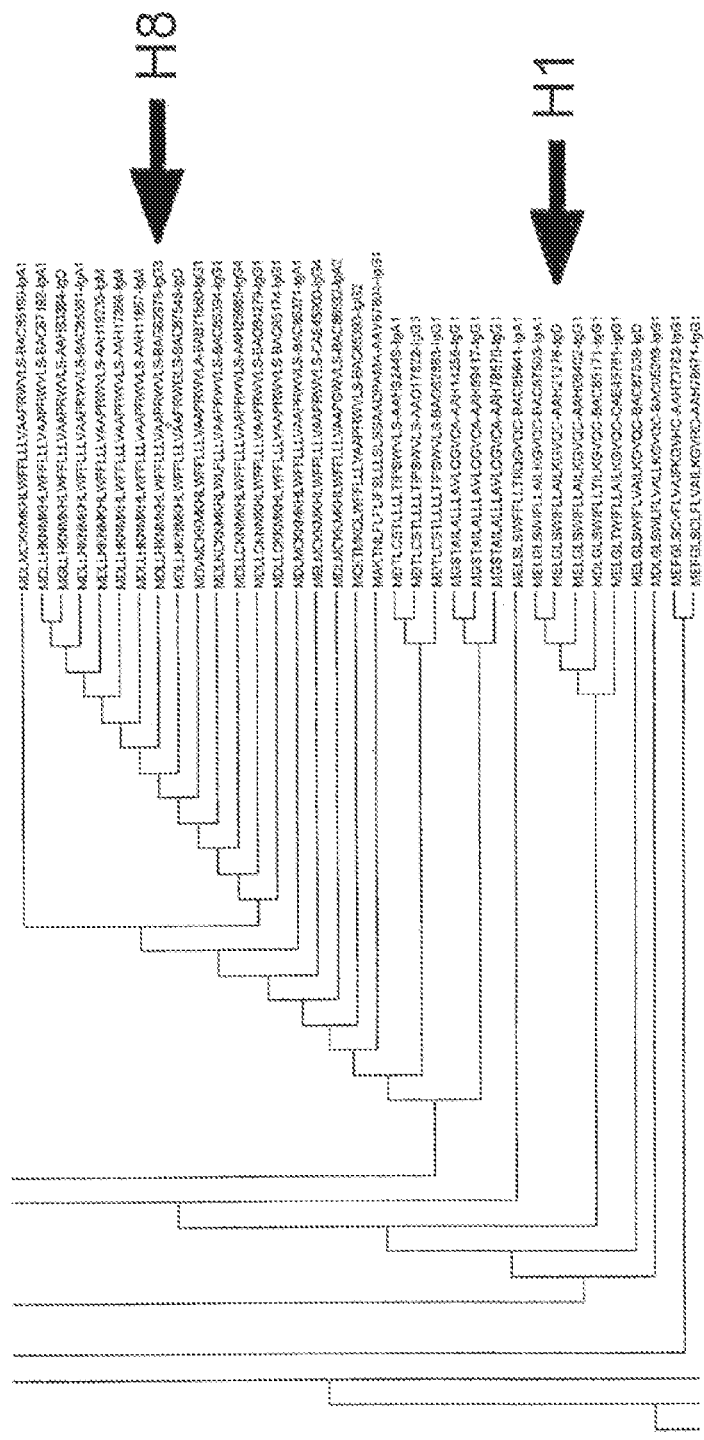
FIG. 2 is a table (Table 1) providing the amino acid sequences and DNA sequences of the heavy and light chain signal peptides that were selected for testing of the antibodies' improved production and secretion. The amino acid sequences correspond to the amino acid sequence already highlighted in FIG. 1 C to G.
FIG. 3 is a series of histogram plots showing the amount of Herceptin heavy chain produced when fused with one of the eight heavy chain signal peptides selected from H1 to H8, as described above, and when co-expressed with the Herceptin kappa light chain fused either to L1 or L2 signal peptide described above.
Figures 1, 1A, 2, 3, 4:
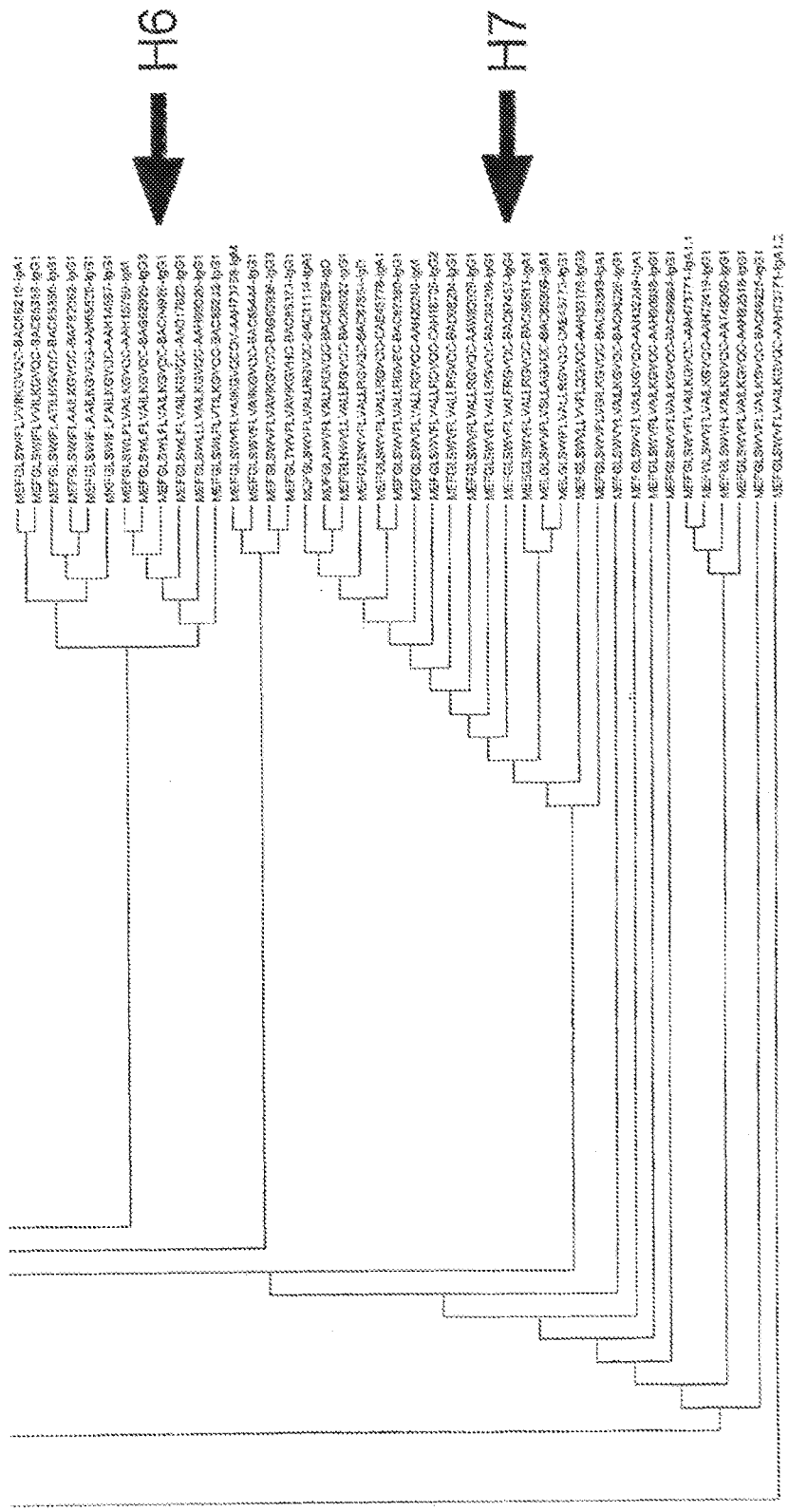
FIG. 4 is a series of histogram plots obtained as in FIG. 3. Avastin heavy and light chain where used instead of Herceptin.
Figure 1B:
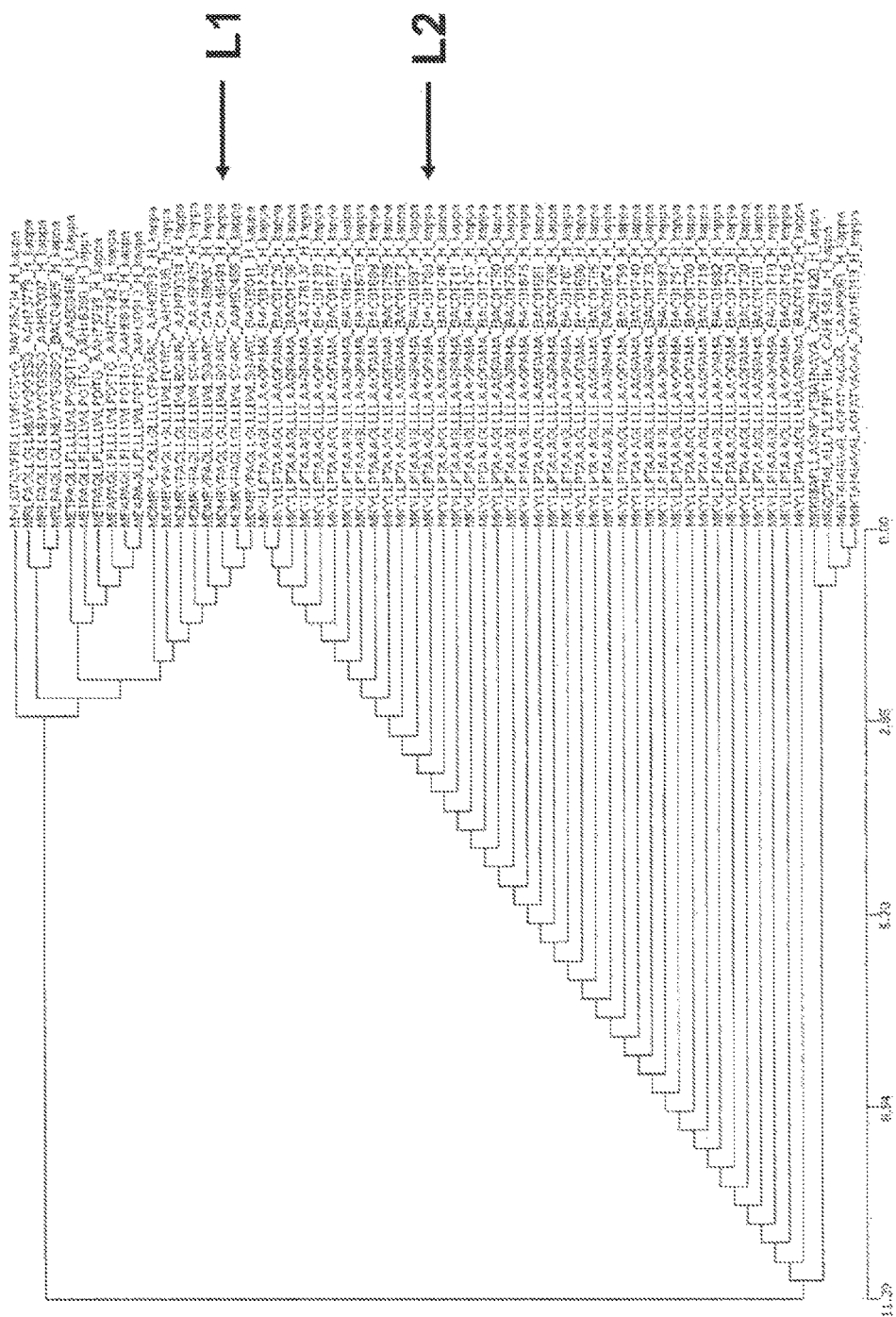
Figure 1C:
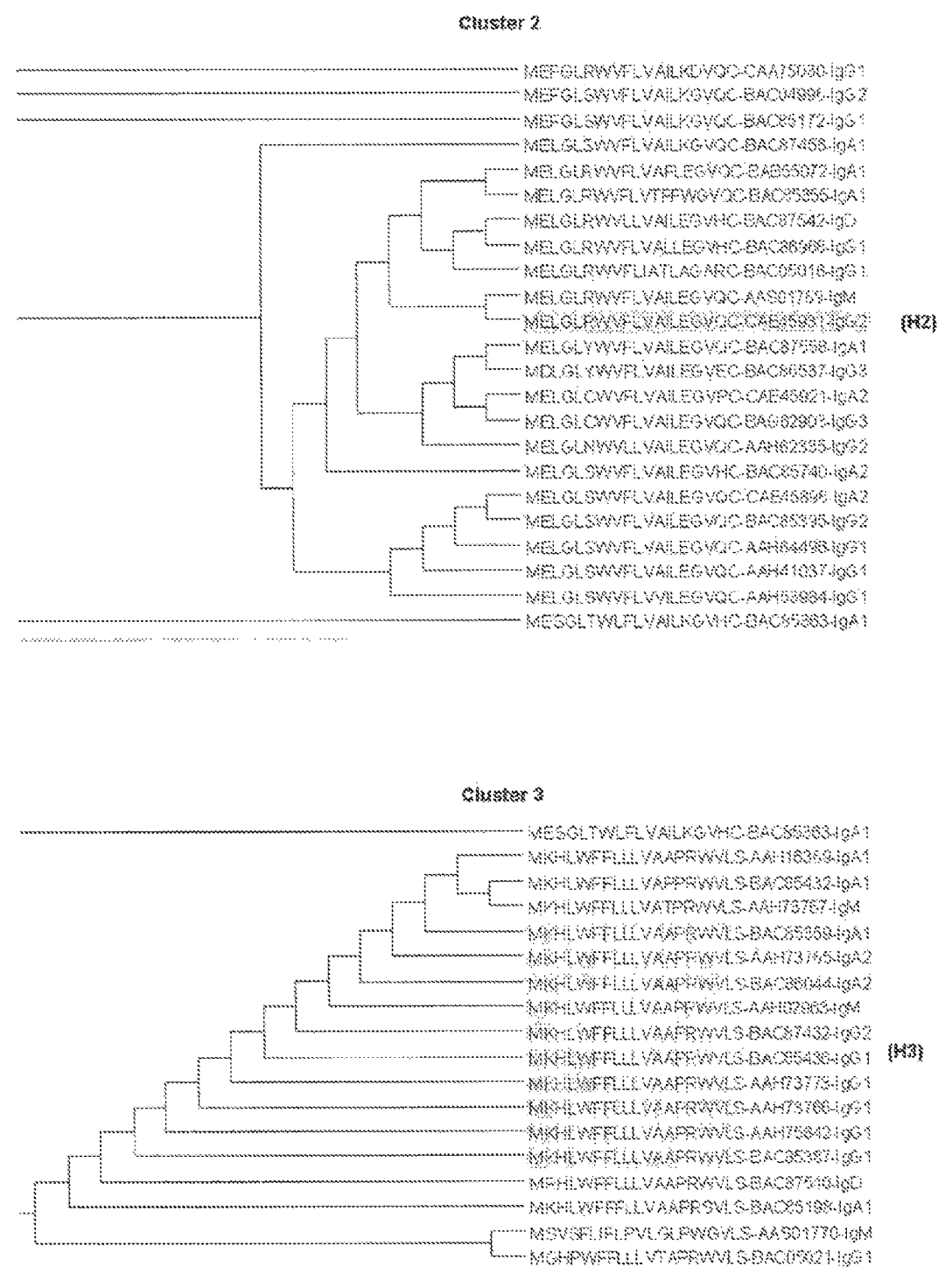

In a non-limiting example in FIG. 1A representing the phylogenetic tree of heavy chain signal peptides from 173 human Ig heavy chain and 1C to 1F representing the amino acid sequences of the signal peptides within each clusters, clusters H1 and H6 for example (FIGS. 1E and 1F) comprise 16 signal peptides sequences. In other words, they comprise 9.25% of the total number of signal peptide in the database (or $$n = \frac{x(Hi)}{x(Ht)} \times 100,$$

wherein n is the number of peptide in a given cluster (given as a percentage) and wherein x(Hi) is the total number of signal peptides in a given cluster and x(Ht) is the total number of signal peptides in the database). In the non-limiting example above taking clusters H1 or H6 as an illustration, x(Hi) is 16 and x(Ht) is 173, thus $$n = \frac{16}{173} \times 100 = 9.25\%.$$

Figure 1D:
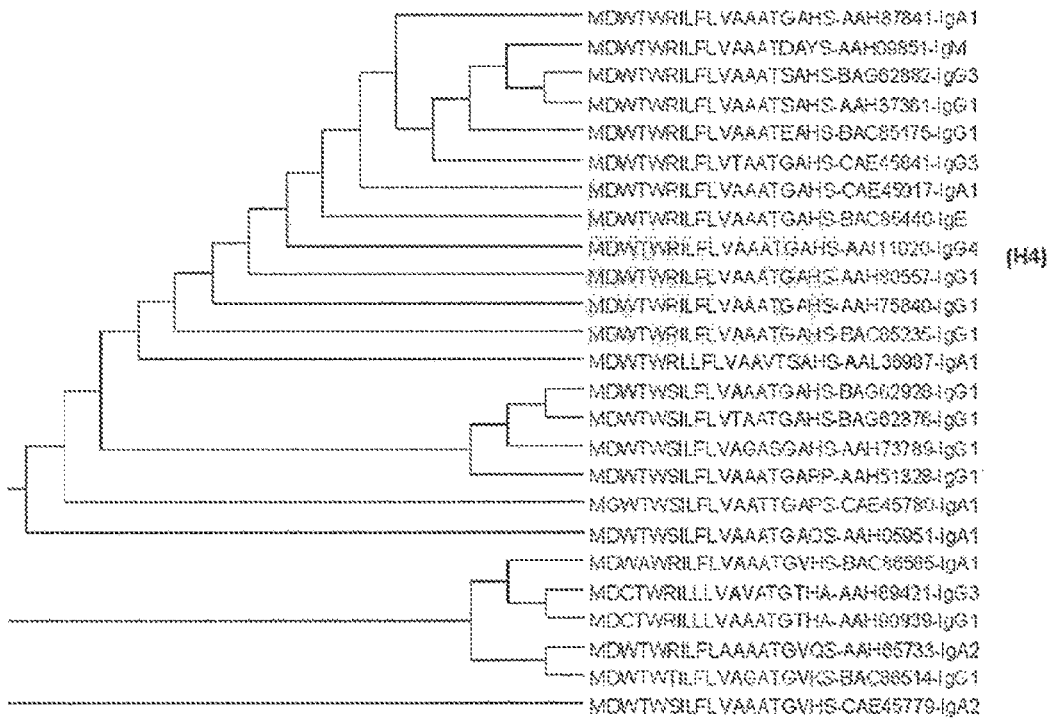
Figure 1D:
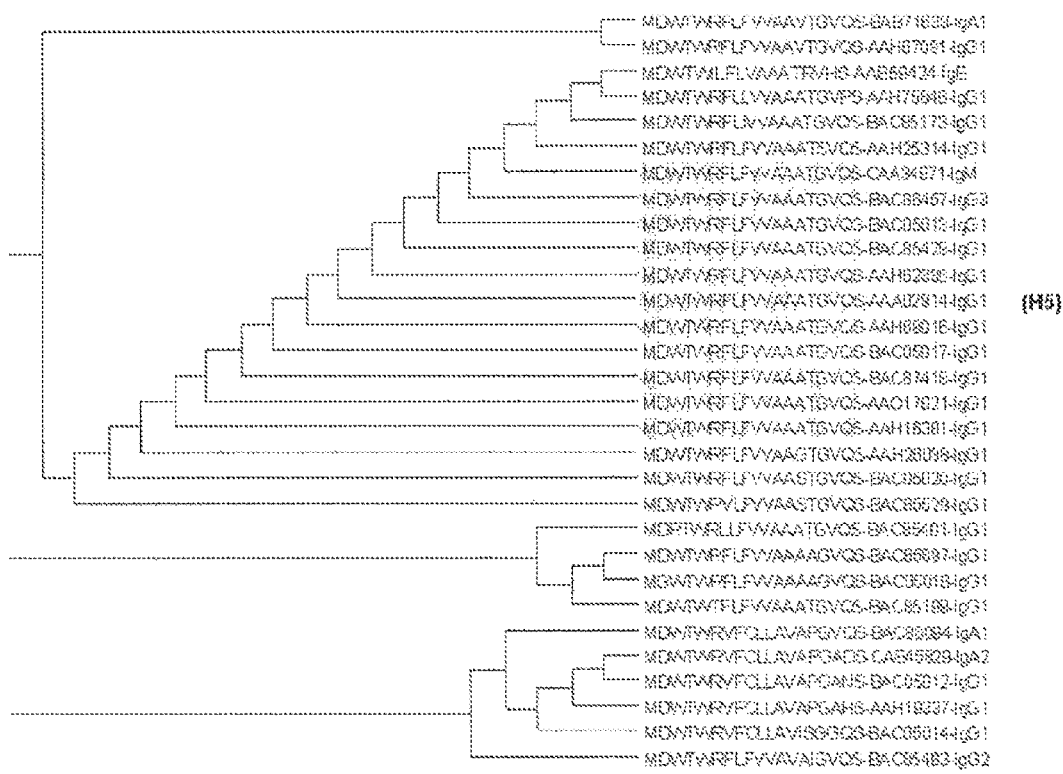
Figure 1E:
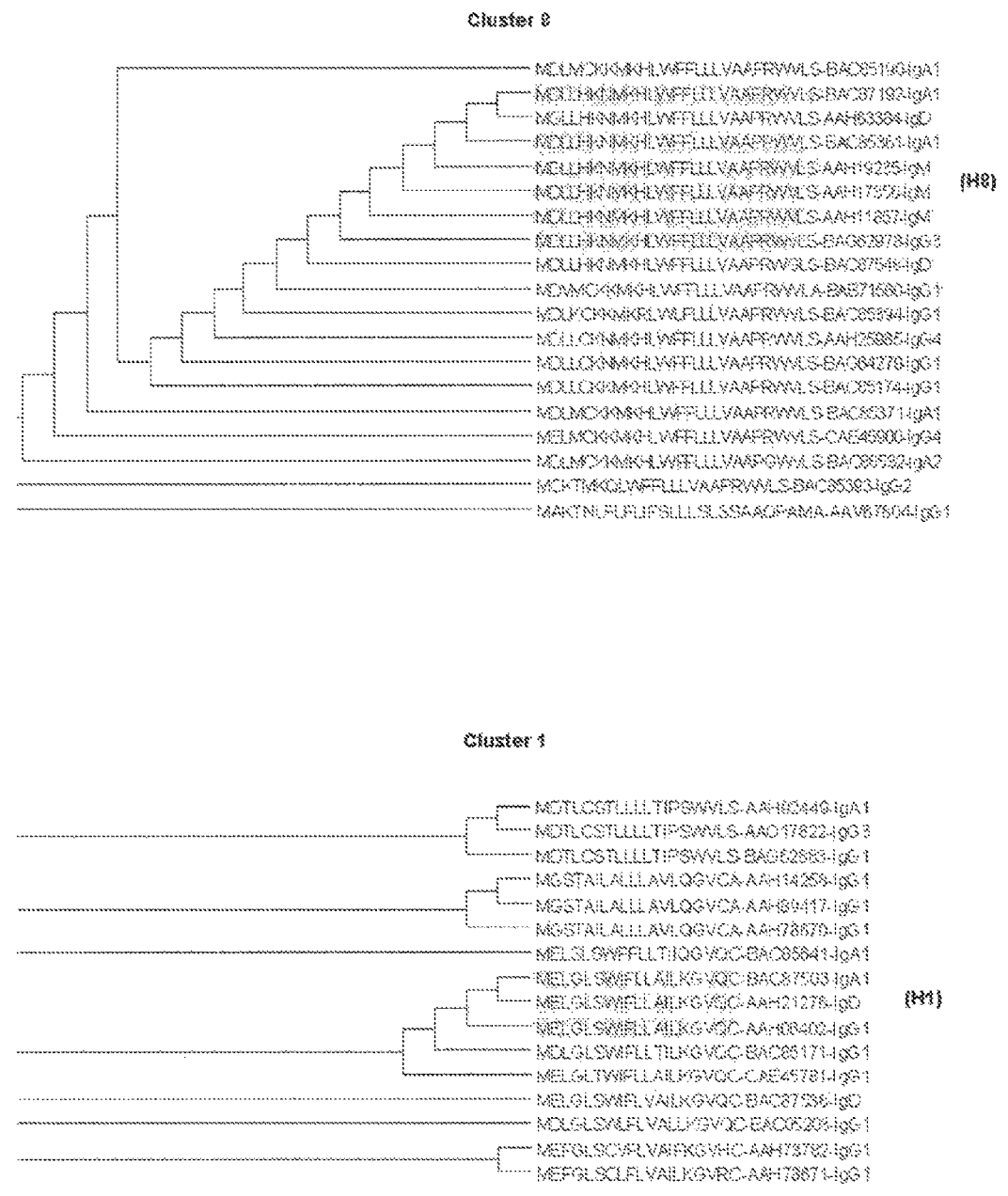
Figure 1F:
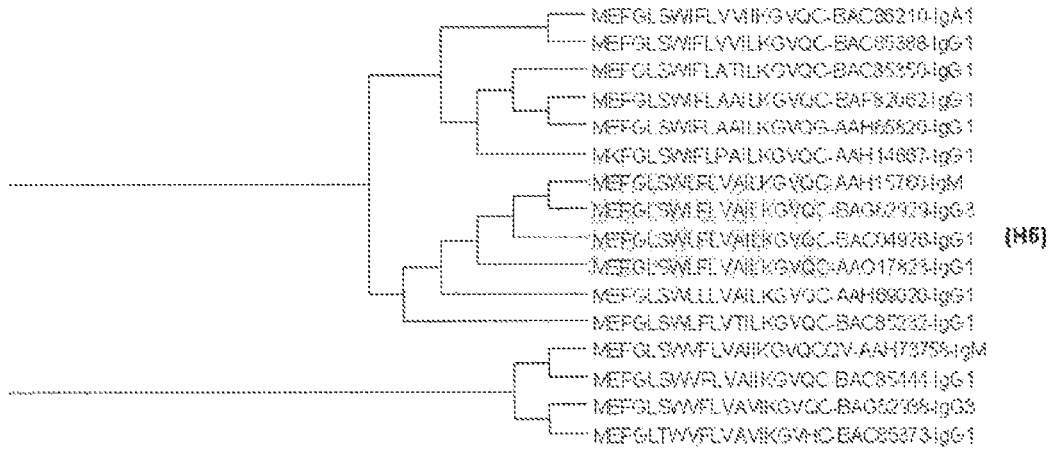
Figure 1F:
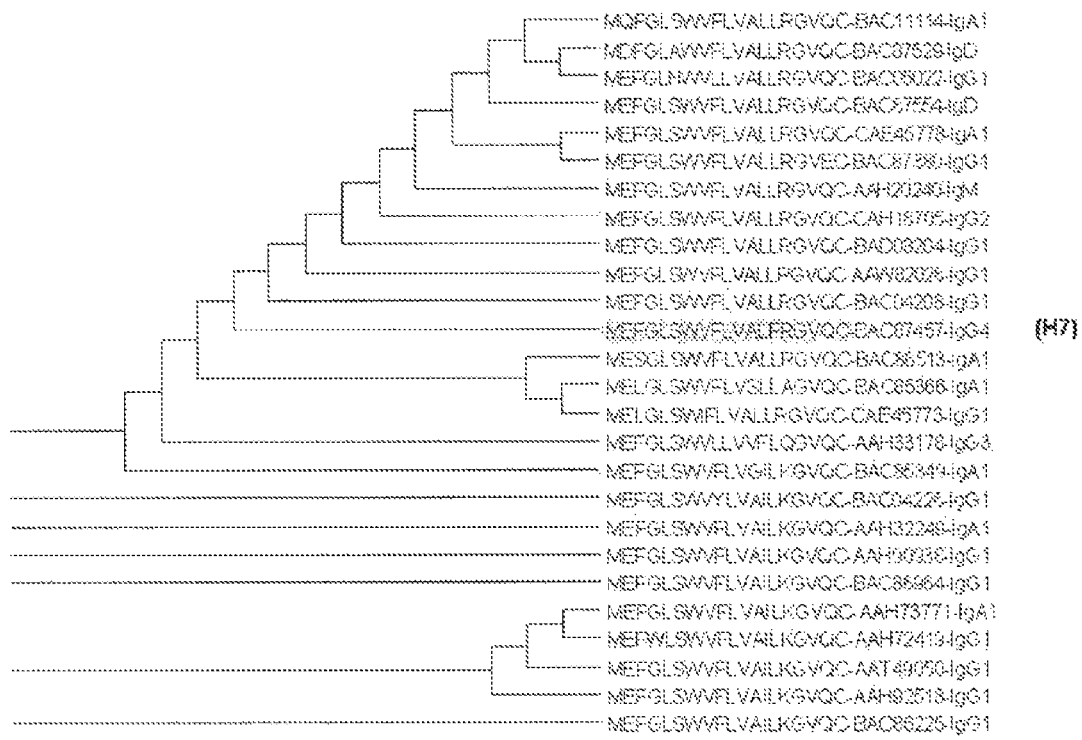
Figure 1G:
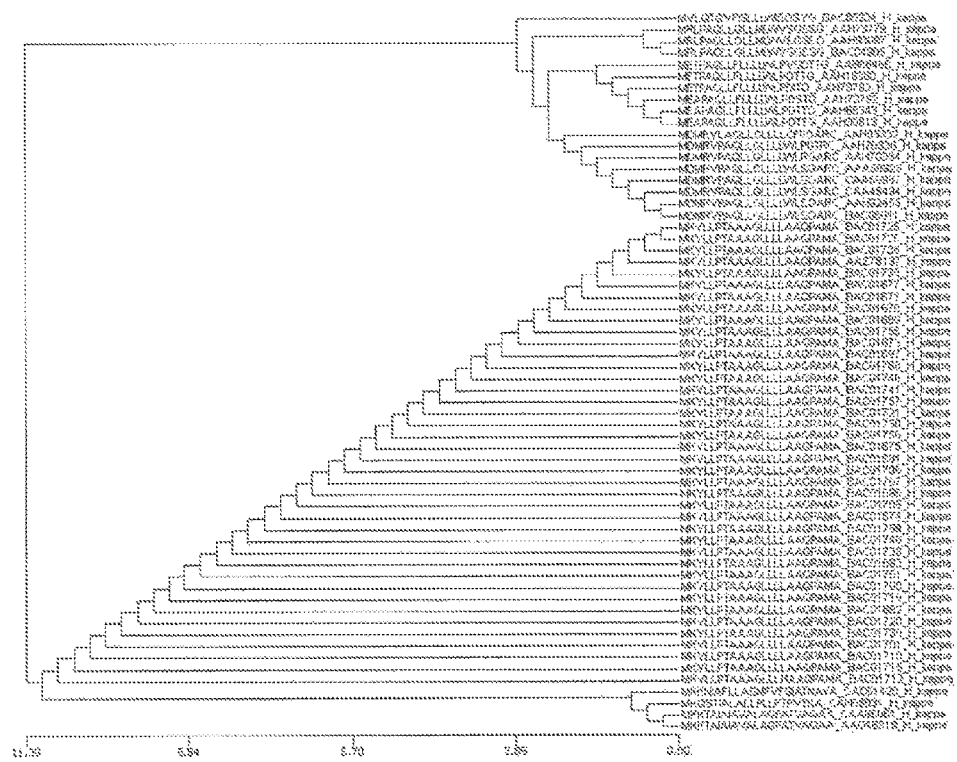
Figure 3:
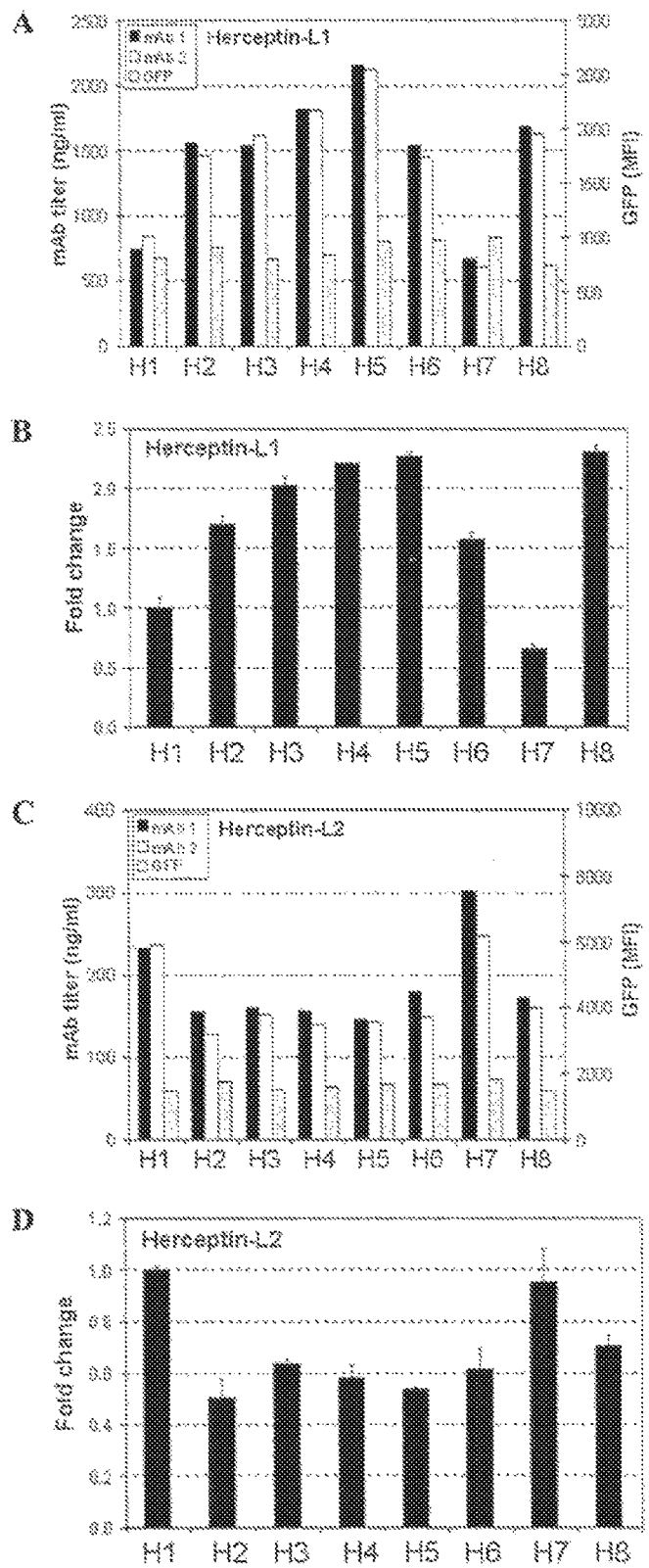
Figure 4:
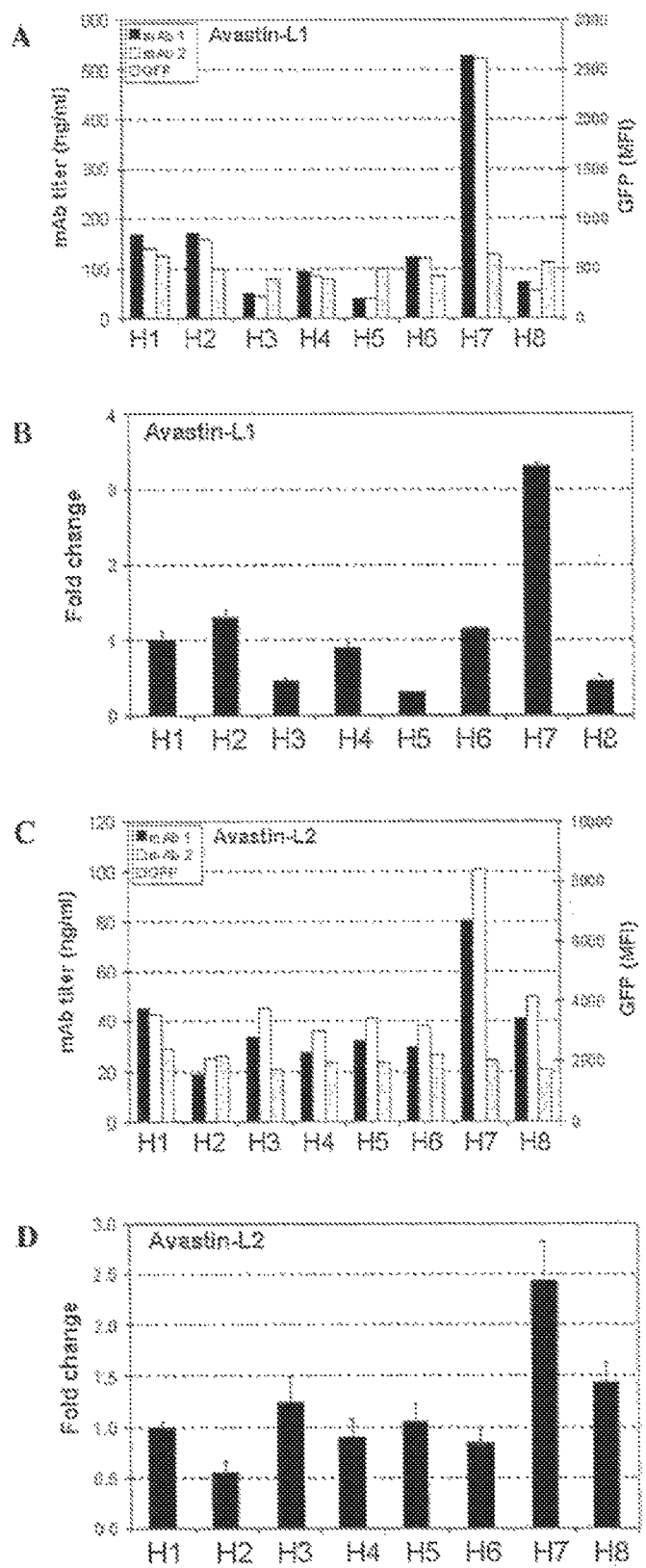
Figure 5:
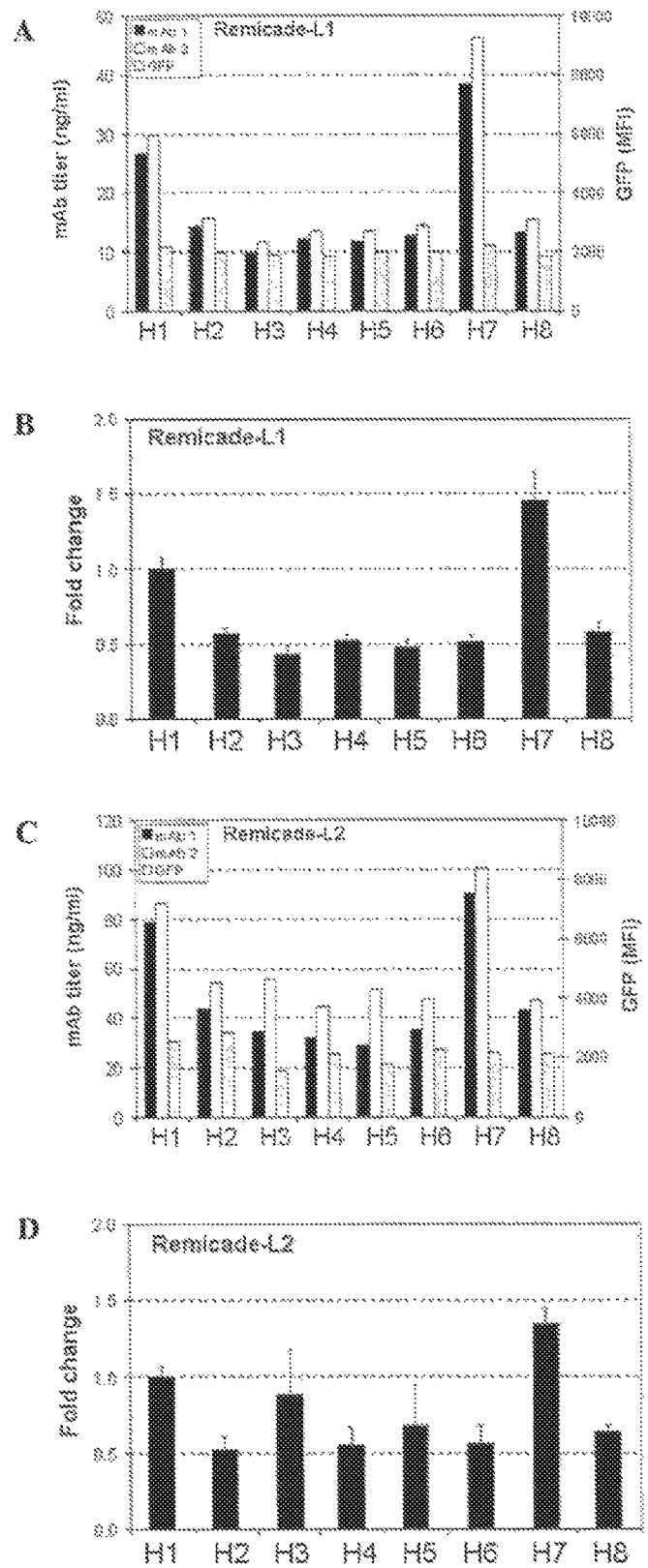
FIG. 5 is a series of histogram plots showing the amount of Remicade heavy chain produced when different signal peptides were used as in FIGS. 3 and 4 above. Light chain with signal peptide 1 was used in FIGS. 5 A and B; and light chain with signal peptide 2 was used in FIGS. 5 C and D; A and C: Ig ELISA results.

Using the above equation, clusters H2 (23 signal peptides) and H3 (18 signal peptides) in FIG. 1 C have about 13.29% and 10.40% of the total number of signal peptides, whereas clusters 4 (25 signal peptides) and H5 (30 signal peptides) in FIG. 1D, H8 (19 signal peptides; FIG. 1E), and H7 (26 signal peptides; FIG. 1E) have 14.45%, 17.34%, 10.98% and 15.03%, respectively of the total number of signal peptides present in the exemplary database of 173 heavy chain signal peptides.

The light chain signal peptides database created from the available sequence information of 62 human kappa light chain only generated two clusters. The two clusters were created due partly to the high degree of similarity/identity of the sequences of the light chain signal peptides in the database. Using the non-limiting example above, L1 contains 18 light-chain signal peptides (or 29.03% of the total number of signal peptides in the database) and L2 contains the remaining 44 light chain signal peptides (or 70.97% of the total number of signal peptides). However, it should be noted that 40 of the light chain signal peptides in cluster L2 have the same amino acid sequence (i.e. 100% sequence identity).

The resulting clusters may contain amino acid sequences of signal peptides that are the same (identical) or different. By "identical", it is meant that the amino acid sequence is 100% conserved (i.e. all the amino acid within the sequences are identical). By different, it is meant that the primary amino acid sequence of the signal peptides within a cluster differ by at least one amino acid. The difference may be related to the length of the amino acid sequence (added or deleted amino acid), the identity of the amino acid (point mutation) or the structure of the sequence.

If the amino acid sequence is different, the amino acid difference may be at least one, at least two, at least three, at least four, at least five, at least six, at least seven, at least eight, at least nine, at least ten, at least eleven, at least twelve, at least thirteen, at least fourteen or at least fifteen amino acids. If the sequences are different, then a consensus sequence may be determined using any multiple alignment computer program available, based on the sequences present in the cluster.

Thus, in one example, there is provided a method of determining a signal peptide for enhancing secretion of an antibody of interest, wherein the method may comprise (a) creating a database consisting of amino acid sequences of a plurality of signal peptides from the heavy chain and the light chain of a plurality of antibodies; (b) clustering the sequences based on sequence similarity, wherein the number of clusters is determined based on the total number of the plurality of signal peptides such that any one of the clusters comprises at least about 5% of the plurality of signal peptides present in the database; (c) selecting at least one amino acid sequence within each clusters of heavy chain signal peptide; and light chain signal peptide, wherein if the amino acid sequences of the signal peptides within the clusters are: (1) identical, then any amino acid sequence may be selected within the cluster; and (2) different, then the at least one amino acid sequence may be selected based on: (i)

the sequence appearing most often in the cluster; and/or (ii) the sequence having the highest similarity to a consensus sequence of the cluster, wherein the consensus sequence is created based on comparison of the amino acid signal peptide sequence within the cluster; (d) fusing polynucleotides encoding the heavy chain of the antibody to a polynucleotide encoding the heavy chain signal peptide selected as defined hereinbefore; and the light chain of the antibody to a polynucleotide encoding the light chain signal peptide selected as defined hereinbefore; wherein selection of different signal peptide amino acid sequences for the antibody results in a library of antibodies fused to different signal sequences selected hereinbefore; (e) creating at least one vector comprising the polynucleotides defined above; and (f) quantifying and comparing the secretion of the antibody after transfection of the at least one vector above into an expression system to determine the combination of heavy and light chain signal peptides, which enhance expression and secretion of the antibody of interest the most.

In one limiting example, by applying the method of the invention described herein, step (a) when applied to available human immunoglobulin amino acid sequence information generated a database of 173 immunoglobulin heavy chain signal peptides and 62 kappa light chain signal peptides amino acid sequences. As more information becomes available, more databases may be created. As explained using the non-limiting example herein, when the clustering of step (b) is applied to the database of 173 heavy chain signal peptides, eight clusters were created, named by H1 to H8, as shown in FIG. 1C to 1F.

The method may further comprise the step of selecting at least one amino acid sequence within at least one cluster of heavy chain signal peptides and light chain signal peptides. For example, the selection may be based on the identity of amino acid sequence within one cluster as indicated above. If all the sequences within at least one cluster are identical as defined above, then any sequence can be selected.

If the sequences within one cluster are different, then at least one signal peptide is selected as being representative of the cluster. For example, if the signal peptide is represented more than once within the cluster and if the signal peptide is represented more often than any other signal peptide within the same cluster, then the signal peptide is selected as being the most representative of the cluster. In case every one of the signal peptides within a cluster has a different amino acid sequence then the most representative signal peptide can be the signal peptide having the highest degree of primary sequence similarity to the consensus sequence of said cluster.

In a non-limiting example, cluster H3 (shown in FIG. 1C) that was created using the signal peptide sequences from 173 Ig human heavy chains described above, contains the signal peptide sequences of 18 Ig human heavy chains. Of the 18 signal peptide sequences, 10 are identical (that is have the same sequence MKHLWFFLLLVAAPRWVLS (H3, SEQ ID NO: 7)) and thus, the signal peptide sequence of SEQ ID NO: 7 was selected as being representative of cluster H3. In a further example, applying the selection step (c) of the method described above to the 23 signal peptide sequences of cluster H2 (see e.g. FIG. 1C), since no sequence appears more often than any other, the sequence selected is MELGLRWVFLVAILEGVQC (H2, SEQ ID NO: 6), which shares the highest similarity with the consensus sequence deducted from the list of 23 signal peptide sequences of cluster H2 as stated in further step 2 (ii) of the method as described herein. Applying the same method to other exemplary clusters H1, H4 to H8, the following approach is taken.

For clusters H4, H5 (see e.g. FIG. 1D), H8, H1 (see e.g. FIG. 1E), and H6 (see FIG. 1F), the signal peptide sequence is selected according to the step (c).(2).(i), that is according to the fact that these sequence appear most often in the aforementioned clusters. Thus, the following amino acid sequences were selected from clusters H4, H5, H8, H1 and H6, respectively: MDWTWRILFLVAAATGAHS (H4, SEQ ID NO: 8), MDWTWRFLFVVAAATGVQS (H5, SEQ ID NO: 1), MDLLHKNMKHLWFFLLLVAAPRWVLS (H8, SEQ ID NO: 10), MELGLSWIFLLAILKGVQC (H1, SEQ ID NO: 5), and MEFGLSWLFLVAILKGVQC (H6, SEQ ID NO: 9). For exemplary cluster H7 (see FIG. 1F), the signal peptide having the amino acid sequence MEFGLSWVFLVALFRGVQC (H7, SEQ ID NO:3) is selected based on the highest similarity to the consensus sequence deducted from the alignment of all 26 sequences within the cluster.

The signal peptide was further optimised by comparing the sequences of the signal peptide within a cluster. For example, the N-domain, H-domain and C-domain described herein were found to encompass the first to the sixth amino acid, the seventh to the fourteenth amino acid and the fifteenth to the nineteenth amino acid of the Ig human heavy chain signal peptide sequence, respectively.

The method of determining the signal peptide for enhancing secretion may further comprise the step of fusing at least one polynucleotide (also referred as oligonucleotide or nucleotide) encoding a signal peptide sequence to at least one polynucleotide encoding the light chain of the antibody of interest and/or the heavy chain of the antibody of interest, wherein the signal peptide has been selected as indicated above and wherein at least one signal peptide is selected from the clusters created from the database created from the signal peptides of light chains and at least one signal peptide is selected from the clusters created from the signal peptides of heavy chains. The number of signal peptides selected may depend on the number of clusters created and the number of peptides selected from each cluster. For example, the number of heavy chain signal peptides selected may comprise 2, 3, 4, 5, 6, 7, 8, 9, 10, 11, 12, 13, 14, 15, 20, 25 or 30 different signal peptides. The number of light chain signal peptides selected may comprise 2, 3, 4, 5, 6, 7, 8, 9, 10, 11, 12, 13, 14, 15, 20, 25, 30 or 35 different signal peptides.

Examples of selected signal peptides are given in the experimental section below and a list of exemplary publicly available antibodies signal peptides is given in FIG. 1. For example, the antibody of interest may be modified by a heavy chain signal peptide. In one example, there is provided the antibody as disclosed herein, wherein the N-domain comprises an amino acid sequence of formula (II): M-$X_{aa1}$-$X_{aa2}$-$X_{aa3}$-$X_{aa4}$-$X_{aa5}$ (SEQ ID NO: 278), wherein $X_{aa1}$ is any one of Asp, Asn or Lys; $X_{aa2}$ is any one of Phe, Leu, His or Trp; $X_{aa3}$ is any one of Gly, Leu or Thr; $X_{aa4}$ is Leu or Trp; $X_{aa5}$ is any one of Ser, Arg or Phe; wherein the amino acid sequence of formula (II) has optionally one or two mutations.

In another example, there is provided the antibody, as described herein, wherein the C-domain comprises an amino acid sequence of the formula (III), $X_{aa14}$-$X_{aa15}$-$X_{aa16}$-$X_{aa17}$-$X_{aa18}$ (SEQ ID NO: 279), wherein $X_{aa14}$ is any one of Arg, Lys, Asp or Thr; $X_{aa15}$ is Gly or Trp; $X_{aa16}$ is Val or Ala; $X_{aa17}$ is any one of Glu, Leu, or His; $X_{aa18}$ is Cys or Ser; wherein the amino acid sequence of formula (III) has optionally one or two mutations.

In an additional example, there is provided the antibody, as disclosed herein, further excluding antibodies whose secretion is no more than 1.5 fold higher when compared to the secretion of the antibody with the lowest secretion. In yet another example, there is provided the antibody, as described herein, further excluding antibodies whose secretion is no more than 2 fold higher when compared to the secretion of the antibody with the lowest secretion.

In one example, there is provide the antibody as disclosed herein, wherein the amino acid sequence of the N-domain of the heavy chain signal peptide is selected from the group consisting of MELGLS (SEQ ID NO: 293), MELGLR (SEQ ID NO: 294), MKHLWF (SEQ ID NO: 295), MDWTWR (SEQ ID NO: 296) and MEFGLS (SEQ ID NO: 297). In another example, there is provided the antibody, as described herein, wherein the amino acid sequence of the C-domain of the heavy chain signal peptide is selected from the group consisting of KGVQC (SEQ ID NO: 298), EGVQC (SEQ ID NO: 299), RWVLS (SEQ ID NO: 300), TGAHS (SEQ ID NO: 301), TGVQS (SEQ ID NO: 302) and RGVQC (SEQ ID NO: 303). In yet another example, there is provided the antibody, as described herein, wherein the amino acid sequence of the H-domain of the heavy chain signal peptide is selected from the group consisting of WIFLLAIL (SEQ ID NO: 304), WVFLVAIL (SEQ ID NO: 305), FLLLVAAP (SEQ ID NO: 306), ILFLVAAA (SEQ ID NO: 307), FLFVVAAA (SEQ ID NO: 308), WLFLVAIL (SEQ ID NO: 309) and WVFLVALF (SEQ ID NO: 310).

Accordingly in one example, there is provided the antibody of interest, as disclosed herein, comprising a heavy chain signal peptide, wherein the amino acid sequence of the heavy chain signal peptide comprises but is not limited to MELGLSWIFLLAILKGVQC (H1, SEQ ID NO: 5), MELGLRWVFLVAILEGVQC (H2, SEQ ID NO: 6), MKHLWFFLLLVAAPRWVLS (H3, SEQ ID NO: 7), MDWTWRILFLVAAATGAHS (H4, SEQ ID NO: 8), MDWTWRFLFVVAAATGVQS (H5, SEQ ID NO: 1), MEFGLSWLFLVAILKGVQC (H6, SEQ ID NO: 9), MEFGLSWVFLVALFRGVQC (H7, SEQ ID NO:3), MDLLHKNMKHLWFFLLLVAAPRWVLS (H8, SEQ ID NO: 10).

In a further example, there is provided an antibody, as disclosed herein, wherein the heavy chain of the antibody of interest is fused to a signal peptide comprising, but not limited to, MDWTWRFLFVVAAATGVQS (H5, SEQ ID NO: 1), and MEFGLSWVFLVALFRGVQC (H7, SEQ ID NO:3).

In one example, there is provided an antibody of interest comprising a light chain signal peptide, wherein the light chain signal peptide comprises an amino acid sequence of formula (IV): $X_{bb6}$-$X_{bb7}$-$X_{bb8}$-$X_{bb9}$-$X_{bb10}$-$X_{bb11}$-$X_{bb12}$-$X_{bb13}$-$X_{bb14}$ (SEQ ID NO: 280), wherein $X_{bb6}$ is Ala or Thr; $X_{bb7}$ is Gln or Ala; $X_{bb8}$ is Leu or Ala; $X_{bb9}$ is Leu or Ala; $X_{bb10}$ is Gly; $X_{bb11}$ to $X_{bb14}$ is Leu; or wherein the amino acid sequence of the formula (IV) has one or two mutations; provided that an antibody showing the lowest secretion is excluded, wherein the lowest secretion is determined by a) fusing polynucleotides encoding the light chain of the antibody of interest to a polynucleotide encoding the light chain signal peptide as defined herein to obtain different combinations of light chain signal peptides and antibody of interest; b) creating at least one expression vector comprising the polynucleotides defined under a); and c) quantifying secretion of the antibody of interest encoded by the vector referred to under b) after transfection into an expression system to determine the antibody with the lowest secretion.

In one embodiment, there is provided the antibody as disclosed herein, wherein the light signal peptide is selected from signal peptides of mammalian kappa light chains. In a further example, there is provided the antibody, as defined herein, wherein the antibody comprises an amino acid sequence of the formula (V): M-$X_{bb1}$-$X_{bb2}$-$X_{bb3}$-$X_{bb4}$-$X_{bb5}$ (SEQ ID NO: 281), wherein $X_{bb1}$ is Asp or Lys; $X_{bb2}$ is Met or Tyr; $X_{bb3}$ is Arg or Leu; $X_{bb4}$ is Val or Leu; $X_{bb5}$ is Pro; and wherein the amino acid sequence of formula (V) has optionally one or two mutations.

In yet another example, there is provided the antibody, as defined herein, wherein the antibody further comprises an amino acid sequence of the formula (VI): $X_{bb15}$-$X_{bb16}$-$X_{bb17}$-$X_{bb18}$-$X_{bb19}$-$X_{bb20}$-$X_{bb21}$ (SEQ ID NO: 282), wherein $X_{bb15}$ is Ala or Trp; $X_{bb16}$ is Ala or Leu; $X_{bb17}$ is Ser or Glu; $X_{bb18}$ is Gly or Pro; $X_{bb19}$ is Ala; $X_{bb20}$ is Arg or Met; $X_{bb21}$ is Ala or Cys; and wherein the amino acid sequence of formula (VI) has optionally one or two mutations.

In one example, there is provided the antibody, as defined herein, wherein the amino acid sequence of the light chain signal peptide may comprise MDMRVP (SEQ ID NO: 311) or MKYLLP (SEQ ID NO: 312). In another example, provided is the antibody, as defined herein, wherein the amino acid sequence of the light chain signal peptide may further comprise SGARC (SEQ ID NO: 313) or QPAMA (SEQ ID NO: 314). In a further example, there is provided the antibody, as defined herein, wherein the amino acid sequence of the light chain signal peptide may also comprise AQLLGLLLLWL (SEQ ID NO: 315) or TAAAGLLLLAA (SEQ ID NO: 316).

Accordingly, in another example, there is provided an antibody of interest comprising a light chain signal peptide, wherein the light chain of the antibody of interest is fused to a signal peptide comprising but not limited to MDMRVPAQLLGLLLLWLSGARC (L1, SEQ ID NO: 2) and MKYLLPTAAAGLLLLAAQPAMA (L2, SEQ ID NO: 4).

Since the antibody of interest may comprise a heavy chain and a light, the present invention also provides for combination of heavy chain and light chain signal peptides to be fused to the antibody of interest in order to improve expression and secretion of said antibody. Accordingly in one example, there is provided the antibody, as disclosed herein, wherein the antibody of interest comprises combinations of one heavy and one light chain signal peptide as defined above for the heavy chain and for the light chain.

In one example, provided herein is an antibody of interest comprising a combination of a heavy chain signal peptide and a light chain signal peptide, wherein the heavy chain signal peptide comprises a N-domain, a H-domain and a C-domain, wherein the heavy chain signal peptide is bound to the heavy chain of the antibody via the C-terminal end of the C-domain and the light chain signal peptide is bound to the light chain of the antibody via the C-terminal end of the C-domain; wherein the H-domain of the heavy chain signal peptide comprises an amino acid sequence of formula (I): $X_{aa6}$-$X_{aa7}$-$X_{aa8}$-$X_{aa9}$-$X_{aa10}$-$X_{aa11}$-$X_{aa12}$-$X_{aa13}$, wherein $X_{aa6}$ is any one of Trp, Phe or Ile; $X_{aa7}$ is any one of Val, Ile or Leu; $X_{aa8}$ is Phe or Leu; $X_{aa9}$ is Leu or Val; $X_{aa10}$ is Val or Leu; $X_{aa11}$ is Ala; $X_{aa12}$ is any one of Leu, Ile or Ala; $X_{aa13}$ is any one of Phe, Leu, Pro or Ala; and wherein the light chain comprises an amino acid sequence of formula (IV): $X_{bb6}$-$X_{bb7}$-$X_{bb8}$-$X_{bb9}$-$X_{bb10}$-$X_{bb11}$-$X_{bb12}$-$X_{bb13}$-$X_{bb14}$, wherein $X_{bb6}$ is Ala or Thr; $X_{bb7}$ is Gln or Ala; $X_{bb8}$ is Leu or Ala; $X_{bb9}$ is Leu or Ala; $X_{bb10}$ is Gly; $X_{bb11}$ to $X_{bb14}$ is Leu; and wherein the amino acid sequence of formula (I) or the formula (IV) has independently one or two mutations; provided that an antibody showing the lowest secretion is excluded, wherein the lowest secretion is determined by a) fusing polynucleotides encoding the heavy chain of the antibody of interest to a polynucleotide encoding the heavy chain signal peptide, as defined herein, and fusing polynucleotides encoding the light chain of the antibody of interest to a polynucleotide encoding the light chain signal peptide, as defined herein, to obtain different combinations of heavy chain signal peptides and antibodies of interest and combinations of light chain signal peptides and antibodies of interest; b) creating at least one expression vector comprising the polynucleotides defined under a); and c) quantifying secretion of the antibody of interest encoded by the vector referred to under b) after transfection into an expression system to determine the antibody with the lowest secretion.

The exclusion of the antibody with the lowest secretion ensures that the selected signal peptide sequence to be fused to the antibody of interest is optimised. In other words, the secretion and expression of the antibody of interest when fused to the selected signal peptide, is improved in comparison to the antibody fused to the signal peptide with the lowest secretion. Methods to create the polynucleotide and measure secretion will be explained in more details below and in the examples.

A threshold may be set to measure antibodies that may be excluded due to their low secretion and may be determined experimentally and empirically. Methods to measure secretion are given in the experimental section below. For example, FIG. 3A is a histogram plot that represents the results provided by an enzyme-linked immunosorbent assay (ELISA) to measure the titer of a mAb produced by the method as described herein. More specifically, in FIG. 3A, an antibody was created by fusing the heavy chain of Herceptin, an antibody of interest, to an Ig heavy chain human signal peptide selected by using the method as described herein. The heavy chain signal peptide was selected from one each of the eight clusters H1 to H8, described herein. Thus, in this example, eight different antibodies corresponding to a fusion of the heavy chain of the Herceptin antibody having the SEQ ID NO: 11 and a heavy chain signal peptide having a sequence of SEQ ID NO: 1, 3, 5, 6, 7, 8, 9 or 10 were created. The antibody was created by fusing the polynucleotide sequence of the heavy chain of Herceptin of SEQ ID NO: 21 in frame with the polynucleotide sequence of the heavy chain signal peptide of any one of SEQ ID NO: 283 to 290 as described herein, inserted in a vector and transfected in CHO cells, together with a same or different vector, comprising the polynucleotide sequence of the light chain of Herceptin having the SEQ ID NO: 26 (encoding for the light chain of Herceptin having the amino acid sequence of SEQ ID NO: 16) fused in frame with the polynucleotide sequence of the light chain signal peptide of SEQ ID NO: 291 (encoding for the light chain signal peptide having the amino acid sequence of SEQ ID NO: 2) in the presence of a vector encoding for the green fluorescent protein (GFP) or any protein or molecule known in the art allowing measurement of transfection efficiency in individual cells or a population of cells. The secreted antibody comprising the heavy chain and the light chain is then titered by ELISA a method well known by a person skilled in the art. The transfection efficiency is measured in the host cells by measuring, for example, the mean fluorescent intensity of the GFP. Accordingly, a raw titer is obtained for all combinations of antibodies comprising the heavy chain of Herceptin fused to the heavy chain signal peptide, as described above, and the light chain of Herceptin fused to the light chain signal peptide, as described above.

In a next step, the values obtained above are first normalized using the mean fluorescence intensity given by the GFP to account for variation in transfection efficiency among the different vectors described above. The secretion efficiency of the heavy chain of Herceptin of SEQ ID NO: 11-heavy chain signal peptide combinations and Herceptin light chain of SEQ ID NO: 16-light chain signal peptide L1 of SEQ ID NO: 2 is then compared to, for example, the combination formed by the heavy chain of Herceptin and the H1 signal peptide of SEQ ID NO: 5 and the light chain of Herceptin SEQ ID NO: 16-light chain signal peptide L1 of SEQ ID NO: 2. Accordingly, as shown for example in FIG. 3B, the Herceptin antibody combination of a heavy chain signal peptide H1 fused to the heavy chain of Herceptin and a light chain signal peptide fused to light chain of Herceptin as described above is given an arbitrary fold change of 1.0.

Thus, the antibody serves as a reference for normalization and comparison of the secretion of the different antibodies combination. For example, in the present invention forty combinations of heavy chain-heavy chain signal peptides were created corresponding to eight different signal peptides fused to five different antibodies and ten combinations of light chain-light chain signal peptides were created corresponding to two different signal peptides fused to five different antibodies. As a result, when expressing the vectors encoding for the aforementioned heavy chain and light chain combinations, a total of eighty antibodies combinations was created.

Using H1 as a reference, any combination that has a fold-change higher than 1.0 has a higher secretion than H1 as described above, any combination that has a fold-change lower than 1.0 has a lower secretion than H1 as described above. Using FIG. 3B as an example, when combinations of Herceptin heavy chain-heavy signal peptide are co-transfected in the presence of Herceptin light chain-light chain signal peptide L1, H2/L1, H3/L1, H4/L1, H5/L1, H6/L1 and H8/L1 have a higher secretion than the H1/L1 combination. Conversely, the H7/L1 combination has a lower secretion than H1/L1. The H5/L1 has a secretion approximately 2.2-fold higher than H1/L1.

Based on the above analysis, the antibodies with the lowest secretion may be excluded. For example, when secretion is measured and compared between the library of antibodies that are created as described above, the antibodies whose secretion is no more than at least about 1.2-fold, or at least about 1.3-fold, or at least about 1.4-fold, or at least about 1.5-fold, or at least about 1.6-fold, or at least about 1.7-fold, or at least about 1.8-fold, or at least about 1.9-fold, or at least about 2.0-fold, or at least about 2.5-fold, or at least about 3.0-fold, or at least about 3.5-fold, or at least about 4.0-fold, or at least about 5.0-fold when compared to the secretion of the antibody with the lowest secretion are excluded.

As an example, in FIGS. 4A and B as well as the experimental section below, the antibody with the lowest normalized secretion is the H7/L1 combination. The H1/L1 combination secretion is about 1.7-fold (i.e. fold change of H1/L1÷fold change of H7/L1 or 1÷0.6) higher than the H7/L1 combination. Thus, by setting the exclusion threshold at 2.0-fold higher than the antibody with the lowest secretion (H7/L1 in this example), the H1/L1 combination would be excluded when Herceptin is the antibody of interest. If the 2.5-fold is selected, then the H6/L1 combination would be further excluded. The combinations with the highest fold-change (i.e. H5/L1 and H8/L1) produce approximately 3.75-fold more antibodies than the H7/L1 combination, when expressed in CHO cells.

By excluded, it is meant that the particular combination of the antibody of interest and signal peptide is not further considered for testing for improved secretion and expression in the expression system into which the vector encoding the antibody of interest was transfected. However, it does not exclude using the antibody as a negative control or further testing the antibody of interest in other expression systems, or modifying the antibody, for example, by mutating the signal peptide sequence that was used.

In a further example, there is provided the antibody as described herein comprising a heavy chain and a light chain, as described herein, wherein the N-domain of the heavy chain comprises an amino acid sequence of formula (II): M-$X_{aa1}$-$X_{aa2}$-$X_{aa3}$-$X_{aa4}$-$X_{aa5}$, wherein $X_{aa1}$ is any one of Asp, Asn or Lys; $X_{aa2}$ is any one of Phe, Leu, His or Trp; $X_{aa3}$ is any one of Gly, Leu or Thr; $X_{aa4}$ is Leu or Trp; $X_{aa5}$ is any one of Ser, Arg or Phe; and wherein the light chain comprises an amino acid sequence of the formula (V): M-$X_{bb1}$-$X_{bb2}$-$X_{bb3}$-$X_{bb4}$-$X_{bb5}$, wherein $X_{bb1}$ is Asp or Lys; $X_{bb2}$ is Met or Tyr; $X_{bb3}$ is Arg or Leu; $X_{bb4}$ is Val or Leu; $X_{bb5}$ is Pro; wherein the amino acid sequence of formula (II) and/or formula (V) has independently, optionally one or two mutations. In yet another example, provided herein is the antibody comprising a heavy chain and a light chain, as described herein, wherein the C-domain of the heavy chain signal peptide comprises an amino acid sequence of the formula (III), $X_{aa14}$-$X_{aa15}$-$X_{aa16}$-$X_{aa17}$-$X_{aa18}$, wherein $X_{aa14}$ is any one of Arg, Lys, Asp or Thr; $X_{aa15}$ is Gly or Trp; $X_{aa16}$ is Val or Ala; $X_{aa17}$ is any one of Glu, Leu, or His; $X_{aa18}$ is Cys or Ser; and wherein the light chain signal peptide comprises an amino acid sequence of the formula (VI): $X_{bb15}$-$X_{bb16}$-$X_{bb17}$-$X_{bb18}$-$X_{bb19}$-$X_{bb20}$-$X_{bb21}$, wherein $X_{bb15}$ is Ala or Trp; $X_{bb16}$ is Ala or Leu; $X_{bb17}$ is Ser or Glu; $X_{bb18}$ is Gly or Pro; $X_{bb19}$ is Ala; $X_{bb20}$ is Arg or Met; $X_{bb21}$ is Ala or Cys; and wherein the amino acid sequence of formula (III) and/or formula (VI) has independently, optionally one or two mutations.

Accordingly, in one example, there is provided the antibody, as described herein, wherein the amino acid sequence of the N-domain of the heavy chain signal peptide may comprise but is not limited to, MELGLS (SEQ ID NO: 293), MELGLR (SEQ ID NO: 294), MKHLWF (SEQ ID NO: 295), MDWTWR (SEQ ID NO: 296) and MEFGLS (SEQ ID NO: 297) and wherein the amino acid sequence of the light chain signal peptide may comprise MDMRVP (SEQ ID NO: 311) or MKYLLP (SEQ ID NO: 312). In a further example, there is provided the antibody as described herein, wherein the amino acid sequence of the C-domain of the heavy chain signal peptide may comprise but is not limited to KGVQC (SEQ ID NO: 298), EGVQC (SEQ ID NO: 299), RWVLS (SEQ ID NO: 300), TGAHS (SEQ ID NO: 301), TGVQS (SEQ ID NO: 302) and RGVQC (SEQ ID NO: 303) and wherein the amino acid sequence of the light chain signal peptide may further comprise SGARC (SEQ ID NO: 313) or QPAMA (SEQ ID NO: 314). In another example, there is provided the antibody, as described herein, wherein the amino acid sequence of the H-domain of the heavy chain signal peptide may comprise but is not limited to WIFLLAIL (SEQ ID NO: 304), WVFLVAIL (SEQ ID NO: 305), FLLLVAAP (SEQ ID NO: 306), ILFLVAAA (SEQ ID NO: 307), FLFVVAAA (SEQ ID NO: 308), WLFLVAIL (SEQ ID NO: 309) and WVFLVALF (SEQ ID NO: 310) and wherein the amino acid sequence of the light chain signal peptide is AQLLGLLLLWL (SEQ ID NO: 315) or TAAAGLLLLAA (SEQ ID NO: 316).

Thus, in one example there is provided the antibody of interest, as disclosed herein, comprising a heavy chain signal peptide, wherein the amino acid sequence of the heavy chain signal peptide comprises but is not limited to MELGLSWIFLLAILKGVQC (H1, SEQ ID NO: 5), MELGLRWVFLVAILEGVQC (H2, SEQ ID NO: 6), MKHLWFFLLLVAAPRWVLS (H3, SEQ ID NO: 7), MDWTWRILFLVAAATGAHS (H4, SEQ ID NO: 8), MDWTWRFLFVVAAATGVQS (H5, SEQ ID NO: 1), MEFGLSWLFLVAILKGVQC (H6, SEQ ID NO: 9), MEFGLSWVFLVALFRGVQC (H7, SEQ ID NO:3), MDLLHKNMKHLWFFLLLVAAPRWVLS (H8, SEQ ID NO: 10) and a light chain signal peptide, wherein the light chain of the antibody of interest is fused to a signal peptide comprising MDMRVPAQLLGLLLLWLSGARC (L1, SEQ ID NO: 2) or MKYLLPTAAAGLLLLAAQPAMA (L2, SEQ ID NO: 4).

Thus, in one example, the method, as disclosed herein, comprises the step of fusing polynucleotides encoding the heavy chain of the antibody to a polynucleotide encoding the heavy chain signal peptide selected, as described herein, and above thereby creating a recombinant heavy chain of the antibody of interest modified with a signal peptide. In another example, the method, as disclosed herein, comprises the step of fusing polynucleotides encoding the light chain of the antibody to a polynucleotide encoding the light chain signal peptide selected, as described herein, and above thereby creating a recombinant heavy chain of the antibody of interest modified with a signal peptide. Fusion of the polynucleotides may be performed using techniques known to the skilled artisan, such as enzymatic ligation, or polymerase chain reaction. The polynucleotides sequences may be obtained using publicly available information or by reverse translation of the amino acid sequences. It would be known to the person skilled in the art how to operably link the coding sequence of the signal peptide and the coding sequence of the antibody so that the resulting protein product is a functional protein product with the desired amino acid sequence. Therefore, the polynucleotide sequence of the signal peptide and the antibody need to be in frame.

The fusion may be performed in such a way that the encoded signal peptide is at the N-terminus of the light chain or at the N-terminus of the heavy chain. In a further example, the signal peptide may be linked to the N-terminus of the variable region of light chain or to the N-terminus of the variable region of the heavy chain of the antibody of interest. In one example, the signal peptide that is fused to the light chain may comprise a signal peptide selected from a cluster created based on dataset generated from the amino acid sequence available of signal peptide from the kappa light chain of antibodies. In another example, the signal peptide that is fused to the light chain may comprise a signal peptide selected from a cluster created based on dataset generated from the amino acid sequence available of signal peptide from the heavy chain of antibodies.

The fused polynucleotide may include a linker to separate the variable region from the signal peptide. The sequence of the signal peptide may include a specific cleavable sequence that may be recognized and specifically cleaved by a signal peptidase. The polynucleotide sequence encoding for the light chain or the heavy chain of the antibody of interest may comprise the full-sequence of the light chain or the heavy chain including the variable region and the constant region of the light chain or the heavy chain or a partial sequence of the light chain or the heavy chain that may encode for the region of the light chain or the heavy chain of the antibody that is of therapeutic interest.

The invention also provides for "derivatives" of the murine or chimeric antibodies, fragments, regions or derivatives thereof, which term includes those proteins encoded by truncated or modified genes to yield molecular species functionally resembling the immunoglobulin fragments. The modifications include, but are not limited to, the addition of genetic sequences coding for cytotoxic proteins such as plant and bacterial toxins. The fragments and derivatives can be produced from any of the hosts of this invention.

Fragments include, for example, Fab, Fab', F(ab')2 and Fv. These fragments lack the Fc fragment of intact antibody, clear more rapidly from the circulation, and can have less non-specific tissue binding than an intact antibody. These fragments are produced from intact antibodies using methods well known in the art, for example by proteolytic cleavage with enzymes such as papain (to produce Fab fragments) or pepsin (to produce F(ab')2 fragments).

In one example, the at least one polynucleotide encoding for the at least one signal peptide fused to a polynucleotide encoding for the light chain and/or the heavy chain is integrated in a vector. In view of the present disclosure, the nucleic acid molecule can be obtained using any molecular biology method known in the art. Those skilled in the art will know how to operably link the signal peptide coding sequence to a coding sequence for a heavy or light chain of an antibody of interest, to thereby obtain a nucleic acid molecule according to an embodiment of the present invention.

The cloning of the recombinant polynucleotide into a vector is well known to the person skilled in the art. A plurality of vectors is available to the skilled artisan to obtain expression of the recombinant light chain and/or heavy chain in the expression system of interest. In one example, at least one vector is created comprising the polynucleotide coding sequence for the signal peptide operably linked to the coding sequence of the heavy chain and/or the light chain of the antibody of interest. In one example, there is provided a vector encoding for at least one recombinant light chain comprising a signal peptide and a light chain which may further comprise a variable and a constant region and at least one recombinant heavy chain comprising a signal peptide and a heavy chain which may further comprise a variable and a constant region. In a further example, there is provided at least one vector encoding at least one recombinant light chain comprising a signal peptide and a light chain which may further comprise a variable and a constant region. In yet another example there is provided at least one vector encoding at least one recombinant heavy chain comprising a signal peptide and a light chain which may further comprise a variable and a constant region. It is meant herein by a "vector encoding", a nucleic acid molecule comprising the polynucleotide sequence of the recombinant antibody of interest that when introduced in a host cell is capable of expressing the recombinant antibody of interest (or the light chain and/or heavy chain thereof), thereby producing the amino acid sequence of the antibody of interest fused to a functional signal peptide. The nucleic acid molecule may be an expression vector.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element resulting in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

Oligonucleotides representing a portion of the variable region sequence are useful for screening for the presence of homologous genes and for the cloning of such genes encoding variable, or constant regions of an antibody of interest. Such probes preferably bind to portions of sequences which encode light chain or heavy chain variable regions which bind an epitope of an antigen of interest. Such techniques for synthesizing such oligonucleotides are well known and disclosed in the art.

Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody of interest or fragment. Such "codon usage rules" are disclosed in the art. Using the "codon usage rules" of Lathe, a single oligonucleotide, or a set of oligonucleotides, that contains a theoretical "most probable" nucleotide sequence capable of encoding antibody of interest variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide or set of oligonucleotides, containing the theoretical "most probable" sequence capable of encoding an antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region gene.

A suitable oligonucleotide, or set of oligonucleotides, which is capable of encoding a fragment of the variable or constant antibody region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing antibodies or variable or constant regions thereof. Single stranded oligonucleotide molecules complementary to the "most probable" variable or constant region peptide coding sequences can be synthesized using procedures which are well known to those of ordinary skill in the art. Additionally, DNA synthesis can be achieved through the use of automated synthesizers. Techniques of nucleic acid hybridization are disclosed. Techniques such as, or similar to, those described above have successfully enabled the cloning of genes for human aldehyde dehydrogenases, fibronectin, the human estrogen receptor gene, tissue-type plasminogen activator and human term placental alkaline phosphatase complementary DNA.

In an alternative way of cloning a polynucleotide encoding a variable or constant region, a library of expression vectors is prepared by cloning DNA or, more preferably, cDNA (from a cell capable of expressing an antibody or variable or constant region) into an expression vector. The library is then screened for members capable of expressing a protein which competitively inhibits the binding of an antibody, and which has a nucleotide sequence that is capable of encoding polypeptides that have the same amino acid sequence as antibodies of interest or fragments thereof. In this embodiment, DNA, or more preferably cDNA, is extracted and purified from a cell which is capable of expressing an antibody of interest or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). Once the nucleic acid sequence encoding such variable or constant regions is isolated, the nucleic acid sequence can be appropriately expressed in a host cell, along with other constant or variable heavy or light chain encoding nucleic acid, in order to provide recombinant MAbs. Such antibodies preferably include a murine or human variable region which contains a framework residue having complementarity determining residues which are responsible for antigen binding.

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including gamma, μ, α, δ or ε, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1), gamma 3 (IgG3), gamma 4 (IgG4), or μ (IgM).

The human $C_L$ region can be derived from human L chain isotype, kappa or lambda. Genes encoding human immunoglobulin C regions are obtained from human cells by standard cloning techniques. Human C region genes are readily available from known clones containing genes representing the two classes of L chains, the five classes of H chains and subclasses thereof. Chimeric antibody fragments, such as F(ab')2 and Fab, can be prepared by designing a chimeric H chain gene which is appropriately truncated. For example, a chimeric gene encoding an H chain portion of an F(ab')2 fragment would include DNA sequences encoding the CH1 domain and the hinge region of the H chain, followed by a translational stop codon to yield the truncated molecule.

Generally, the murine, human and chimeric antibodies, fragments and regions of the present invention are produced by cloning DNA segments encoding the H and L chain antigen-binding regions of an antibody of interest, and joining these DNA segments to DNA segments encoding $C_H$ and $C_L$ regions, respectively, to produce murine, human or chimeric immunoglobulin-encoding genes.

Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

In a further example, the method can comprise quantifying and comparing secretion of the antibody after transfection of at least one vector into an expression system to determine the combination of heavy and light chain signal peptides, as to which combinations enhance expression and secretion of the antibody the most. Introduction of the vector into the expression system may be achieved by transfection, electroporation or any technique known in the art. As used herein the term "expression system" relates to a system that allows protein expression, that is the way in which proteins are synthesized, modified and regulated in living organism. The term can refer to the system required to manufacture proteins. Recombinant protein production in living organisms will depend on using cellular machinery.

The expression system may be a host cell or a cell-free expression system. For the purpose of the present invention where secretion of the recombinant antibody is to be assessed the expression system may be a host cell. The vector can be introduced in a host cell to obtain a recombinant cell. The recombinant cell can be grown under conditions suitable for the expression and secretion of the antibody of interest.

Transfection may be a single transfection if the vector encodes for the recombinant heavy chain and the recombinant light chain or may be a co-transfection, to introduce at least two vectors independently encoding for a recombinant heavy chain comprising the heavy chain of the antibody of interest and the signal peptide to be tested and for a recombinant light chain comprising the light chain of the antibody of interest and the signal peptide to be tested. According to an example, transfection of the at least one vector in the expression system may be transient or stable. In case the transfection is a stable transfection, at least one vector may encode for a selectable marker, thereby allowing identification of expression system having the vector of interest.

Quantification of the secreted recombinant antibody may comprise but is not limited to IgG ELISA assay, Western Blotting, immunoprecipitation, immunofluorescence, mass spectrometry or Fluorescence activated cell sorting (FACS). The quantification of the secretion of the recombinant antibody may provide numerical values thereby allowing comparison between different recombinant antibodies comprising different signal peptides. Thus, the method allows determining which signal peptide enhances expression and secretion of the antibody of interest the most.

In one embodiment, the method as described above may further comprise mutating at least one amino acid of the signal peptide to be fused to the antibody of interest. For example, the signal peptide amino acid sequence may comprise at least one, at least two, at least three, at least four or at least five mutations. In one example, disclosed herein, is the antibody of interest, as disclosed herein, wherein the antibody of interest comprises the heavy chain signal peptide that may comprise one or two or three or four mutations in the heavy chain signal peptide. In another example, there is proved the antibody, as disclosed herein, wherein the antibody of interest comprises the light chain signal peptide comprising one or two or three or four mutations in the light chain signal peptide.

Mutating may comprise changing the nucleotide sequence of the signal peptide thereby changing the encoded amino acid (missense mutation), deleting an amino acid from the signal peptide sequence or inserting a new amino acid into the signal peptide sequence.

In a further example, the at least one amino acid is mutated after determining a consensus sequence as indicated above. The consensus sequence is created based on comparison of the amino acid signal peptide sequences within one of the groups clusters created as indicated above. In another example, the amino acid to be mutated within the signal peptide sequence is not an amino acid of the consensus sequence.

A chimeric antibody, such as a mouse-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

In some embodiments, the host cell may comprise a eukaryotic cell or a prokaryotic cell. The eukaryotic cell may comprise but is not limited to a mammalian cell, an avian cell, an insect cell, a fungal cell, a yeast cell and a plant cell. The prokaryotic cell can be a bacterial cell. In a further example, the expression system, as disclosed herein, can comprise, but is not limited to, a Chinese Hamster Ovary Cell (CHO cell), a baculovirus expression vector system, a *Leishmania tarentolae* expression system, a galline (chicken) cell, a yeast expression system, and a plant expression system. The person skilled in the art would know how to select a suitable expression system for the purpose of producing recombinant antibodies of interest.

In one example, the antibody of interest whose expression and secretion is monitored to determine the signal peptide which enhances the expression the most, comprises, but is not limited to, a monoclonal antibody, a chimeric antibody, an humanized antibody, derivatives, regions or fragments thereof. In one example, the method provides a monoclonal antibody.

The antibody (also referred to as immunoglobulins) as defined herein may have an isotype comprising but not limited to IgG, IgM, IgD, IgA and IgE. The isotype of the antibody is determined by the nature of its heavy chain. For example, in mammals there are five types of Ig heavy chains, denoted by the Greek letters gamma (γ), mu (μ), delta (δ), alpha (α) and epsilon (ε). As indicated herein, in mammals there are two types of immunoglobulin light chain, which are called lambda (λ) and kappa (κ).

Any antibody of interest can be expressed and secreted by the method, as disclosed herein. As will be seen herein, examples of antibody of interest may comprise recombinant therapeutic antibodies such as trastuzumab (Herceptin, CAS number 180288-69-1; Heavy Chain (H) SEQ ID NO: 11; Light Chain (L) SEQ ID NO: 16), bevacizumab (Avastin, CAS number 216974-75-3; (H) SEQ-ID NO:12; (L) SEQ ID NO: 17), infliximab (Remicade, CAS number 170277-31-3; (H) SEQ ID NO:13; (L) SEQ ID NO: 18), rituximab (Rituxan, CAS number 174722-31-7; (H) SEQ ID NO: 14; (L) SEQ ID NO: 19) and adalimumab (Humira, CAS number 331731-18-1; (H) SEQ ID NO: 15; (L) SEQ ID NO: 20).

As indicated above, the at least one vector encoding the recombinant antibody of interest may comprise, for example, the recombinant heavy chain comprising the heavy chain of the antibody of interest and the signal peptide and the recombinant light chain comprising the light chain of the antibody of interest and the signal peptide. For example, a first vector encoding the recombinant light chain of interest and a second vector encoding the recombinant heavy chain of interest may be co-transfected into the host cell.

Therefore, in one example, there is provided an antibody of interest that may comprise combinations of one heavy and one light chain signal peptide, as defined herein, and above for the heavy chain and for the light chain. In a further example, there is provided the antibody of interest may comprise combinations of one heavy and one light chain signal peptide wherein a signal peptide comprising, but not limited to, MELGLSWIFLLAILKGVQC (H1, SEQ ID NO: 5), MELGLRWVFLVAILEGVQC (H2, SEQ ID NO: 6), MKHLWFFLLLVAAPRWVLS (H3, SEQ ID NO: 7), MDWTWRILFLVAAATGAHS (H4, SEQ ID NO: 8), MDWTWRFLFVVAAATGVQS (H5, SEQ ID NO: 1), MEFGLSWLFLVAILKGVQC (H6, SEQ ID NO: 9), MEFGLSWVFLVALFRGVQC (H7, SEQ ID NO:3), MDLLHKNMKHLWFFLLLVAAPRWVLS (H8, SEQ ID NO: 10) for the heavy chain and a signal peptide, comprising but not limited to, MDMRVPAQLLGLLLLWLSGARC (L1, SEQ ID NO: 2) and MKYLLPTAAAGLLLLAAQPAMA (L2, SEQ ID NO: 4) for the light chain.

As indicated above, an antibody of interest may comprise a recombinant therapeutic antibody. Thus in one example, there is provided an antibody, as defined herein, wherein the antibody of interest comprises, but is not limited to, an antibody used for the treatment of breast cancer, colorectal cancer, lung cancer, glioblastoma, kidney cancer and ovarian cancer; an autoimmune disease, rheumatoid arthritis (RA), lymphoma, leukemia, and transplant rejection.

In one embodiment, there is provided the antibody of interest, as described herein, wherein the antibody of interest used for the treatment of breast cancer is trastuzumab ((H) SEQ ID NO: 11; (L) SEQ ID NO: 16) or bevacizumab ((H) SEQ ID NO:12; (L) SEQ ID NO: 17). In a further embodiment, there is provided the antibody, as described herein, wherein the antibody of interest used for the treatment of colorectal cancer, lung cancer, glioblastoma, kidney cancer and ovarian cancer is bevacizumab ((H) SEQ ID NO: 12; (L) SEQ ID NO: 17).

In yet another embodiment, there is provided the antibody, as described herein, and above, wherein the antibody of interest used for the treatment of an autoimmune disease and rheumatoid arthritis is infliximab ((H) SEQ ID No. 13; (L) SEQ ID NO: 18) or rituximab ((H) SEQ ID No. 14; (L) SEQ ID NO: 19) or adalimumab ((H) SEQ ID No. 15; (L) SEQ ID NO: 20). In an embodiment, there is provided the antibody, as described herein, wherein the autoimmune disease may comprise, but is not limited to, psoriasis, Crohn's disease, ankylosing spondylitis, psoriatic arthritis, rheumatoid arthritis, and ulcerative colitis. Thus, in one example, there is provided the antibody as described above, wherein the antibody of interest used for the treatment of lymphoma, leukemia and transplant rejection is rituximab ((H) SEQ ID No. 14; (L) SEQ ID NO: 19).

The present disclosure also provides a nucleotide sequence encoding the antibody of interest, as described herein. For example, the nucleotide sequence comprises, but is not limited to, the nucleotide sequence encoding for trastuzumab (Herceptin; (H) SEQ ID NO: 21; (L) SEQ ID NO: 26), bevacizumab (Avastin; (H) SEQ ID NO: 22; (L) SEQ ID NO: 27), infliximab (Remicade; (H) SEQ ID NO: 23; (L) SEQ ID NO: 28), rituximab (Rituxan; (H) SEQ ID NO: 24; (L) SEQ ID NO: 29) and adalimumab (Humira; (H) SEQ ID NO: 25; (L) SEQ ID NO: 30).

The present disclosure also provides a vector comprising the nucleotide sequence, as described herein. As indicated above, there is provided a host cell comprising the nucleotide sequence and/or the vector, as disclosed herein. The vector or nucleotide sequence may be introduced in the host cell, as disclosed above.

The techniques to raise antibodies of the present invention to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art.

Antibodies, fragments or derivatives having chimeric H chains and L chains of the same or different variable region binding specificity, can also be prepared by appropriate association of the individual polypeptide chains, according to known method steps.

With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains can be allowed to associate spontaneously in the culture medium, followed by recovery of the assembled immunoglobulin, fragment or derivative.

The hybrid cells are formed by the fusion of a non-human antibody of interest-producing cell, typically a spleen cell of an animal immunized against either natural or recombinant human ligand comprising the antigen, or a peptide fragment of the human epitope protein sequence. Alternatively, the non-human antibody of interest-producing cell can be a B lymphocyte obtained from the blood, spleen, lymph nodes or other tissue of an animal immunized with a ligand comprising the antigen.

The second fusion partner, which provides the immortalizing function, can be a lymphoblastoid cell or a plasmacytoma or myeloma cell, which is not itself an antibody producing cell, but is malignant. Preferred fusion partner cells include the hybridoma SP2/0-Ag14, abbreviated as SP2/0 (ATCC CRL1581) and the myeloma P3X63Ag8 (ATCC TIB9), or its derivatives.

Murine hybridomas, which produce mAbs specific for ligands, are formed by the fusion of a mouse fusion partner cell, such as SP2/0, and spleen cells from mice immunized against purified antigen containing protein, recombinant antigen containing protein, natural or synthetic antigen containing peptides, including peptides including 5 or more amino acids or other biological preparations comprising antigen containing protein. To immunize the mice, a variety of different conventional protocols can be followed. For example, mice can receive primary and boosting immunizations of antigen containing protein.

The antibody-producing cell contributing the nucleotide sequences encoding the antigen-binding region of the chimeric antibody of the present invention can also be produced by transformation of a non-human, such as a primate, or a human cell. For example, B lymphocyte can be transformed by providing a transforming gene or transforming gene product, as is well-known in the art.

The cell fusions are accomplished by standard procedures well known to those skilled in the field of immunology. Fusion partner cell lines and methods for fusing and selecting hybridomas, and screening for mAbs are well known in the art.

The antibody of interest-specific murine or chimeric mAbs of the present invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAbs from the cell culture medium or recombinantly, in eukaryotic or prokaryotic cells.

Thus in an example, there is provided a hybridoma cell line capable of producing the antibody of interest. In some examples, there is provided the amino acid sequence comprising the amino acid sequence for a recombinant therapeutic antibody of interest, a heavy chain signal peptide amino acid sequence fused to the heavy chain amino acid sequence of the antibody of interest, and a light chain amino acid sequence. In case the antibody heavy chain amino acid sequence already comprises an amino acid signal peptide sequence, then said amino acid signal peptide sequence is replaced by the optimized amino acid signal peptide sequence of the invention. Accordingly, in the specific non-limiting examples below it is understood that the amino acid sequence of the heavy or light chain of the exemplary antibodies of interest should not contain the amino acid sequence of a signal peptide. In case such an amino acid signal peptide sequence comprises the heavy or light amino acid sequence at the C-terminus of the molecule, then said amino acid signal peptide sequence should be replaced by an optimised amino acid signal peptide sequence.

In a further example, disclosed herein is an amino acid sequence comprising the amino acid sequence for trastuzumab (SEQ ID NO: 11); a heavy chain signal peptide of SEQ ID NO: 1 fused to the heavy chain amino acid sequence of trastuzumab; and a light chain signal peptide of SEQ ID NO: 2. In another example, there is provided an amino acid sequence comprising the amino acid sequence for bevacizumab, a heavy chain signal peptide of SEQ ID NO: 3 fused to the heavy chain amino acid sequence of bevacizumab (SEQ ID NO: 12), and a light chain signal peptide of SEQ ID NO: 5 fused to the light chain amino acid sequence of bevacizumab (SEQ ID NO: 16).

In a further example, there is provided an amino acid sequence comprising the amino acid sequence for infliximab, a heavy chain signal peptide of SEQ ID NO: 3 fused to the heavy chain amino acid sequence of infliximab (SEQ ID NO: 13), and a light chain signal peptide of SEQ ID NO: 4 fused to the light chain amino acid sequence of infliximab (SEQ ID NO: 18).

Disclosed herein is an amino acid sequence comprising the amino acid sequence for rituximab, a heavy chain signal peptide of SEQ ID NO: 3 fused to the heavy chain amino acid sequence of rituximab (SEQ ID NO: 14), and a light chain signal peptide of SEQ ID NO: 4 fused to the light chain amino acid sequence of rituximab (SEQ ID NO: 19).

Also disclosed herein, is an amino acid sequence comprising the amino acid sequence for adalimumab, a heavy chain signal peptide of SEQ ID NO: 3 fused to the heavy chain amino acid sequence of adalimumab (SEQ ID NO:

15), and a light chain signal peptide of SEQ ID NO: 5 fused to the light chain amino acid sequence of adalimumab (SEQ ID NO: 20).

Accordingly, there is provided a nucleotide sequence encoding an antibody as disclosed herein and above. There is also provided a vector comprising a nucleotide sequence as defined above.

Whilst the issue of secretion efficiency of heavy and light chains of recombinant antibodies of interest is primarily considered in relation to the signal peptides, the inventors also determined whether the secreted recombinant antibody conserved its activity. Cleavage heterogeneity may arise from nonspecific cleavage of the signal peptide by the signal peptidase. As this occurs within the variable region in the N-terminus of both the heavy and light chains, it may affect the specificity of the secreted antibody in view of antigen recognition. Another heterogeneity issue that may affect recombinant antibody production is the glycan heterogeneity present at the N-glycosylation site of the $C_{H2}$ constant domain of the heavy chains.

Thus, there is provided a method wherein the secreted recombinant antibody is analyzed by mass spectrometry to detect whether the cleaved signal peptide corresponds to the signal peptide that was fused to the heavy and/or light chain of the antibody of interest. The presence of the signal peptides that were originally fused indicates a homogenous cleavage, which further indicates that the cleavage by the signal peptidase is specific. Thus the secreted antibody maintains its integrity and specificity.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. It must be noted that as used herein and in the appended claims, the singular forms "a," "an," and "the" include plural reference unless the context clearly dictates otherwise.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims and non-limiting examples.

Experimental Section

Generation of Antibody Heavy Chain and Light Chain Constructs

Signal peptides from 173 human antibody heavy chains (SEQ ID NO: 1, 3, 5-10 and 43 to 214) were analyzed by a sequencing alignment. These antibodies include IgG, IgM, IgD, IgA and IgE. Signal peptides from 57 human kappa chains (SEQ ID NO: 2, 4 and 215 to 276) were also analyzed by sequencing alignment. The sequence alignment results are shown in FIG. 1. Based on these results, eight heavy chain signal peptides and two kappa light chain signal peptides (FIG. 2) were chosen and compared for their impact on antibody secretion. Five best-selling therapeutic recombinant antibodies, namely Avastin, Herceptin, Humira, Remicade and Rituxan, were used as model molecules. Each antibody heavy chain and light chain was fused to eight signal peptides and two signal peptides, respectively, by overlapping PCR and ligated into the vector pcDNA3.1 (Invitrogen). Each of the eight heavy chains was co-transfected with two different light chain constructs separately (FIG. 3). Therefore, for each antibody, 16 heavy chain- and light chain combinations were transfected into CHO-K1 cells as described below. Combinations of Rituxan with its original heavy chain and light chain signal peptides were also constructed in pcDNA3.1.

Transient Transfection of Antibody Constructs

Transient antibody expression using eight different heavy chain signal peptides and two light chain signal peptides were performed. Transfections were carried out in 6-well tissue culture plate using Fugene 6 (Roche, Indianapolis, Ind.). 2 mL of adherent CHO K1 cells at exponential phase were seeded at density of $3\times10^5$ cells/mL in 6-well plates 24 h prior to transfection. Duplicate transient transfections for each set of mAb vectors were performed using a Fugene 6 to plasmid ratio of 6 µL:2 µg. 1 ug of each light chain and heavy chain bearing plasmids was used in each transfection. To normalize transfection efficiency, a third transfection was carried out in parallel, with an added 0.2 µg of plasmid bearing a gene coding for green fluorescence protein (GFP), pMax-GFP (Amaxa, Gaithersburg, Md.). At 48 h post-transfection, supernatant from cultures transfected with only mAb vectors was collected for analysis of mAb concentration using ELISA, and cells from cultures co-transfected with GFP were collected to measure the fluorescence intensity using a FACS Calibur (Becton Dickinson, Bedford, Mass.). Results were normalized to the GFP expression and expression level of S1, the first heavy chain signal peptide.

Quantification of Secreted Antibody by IgG ELISA Assay

The enzyme-linked immunosorbent assay (ELISA) was carried out in 96-well flat bottom MaxiSorp immunoplates (NUNC). The plates were first coated with 50 µL of goat anti-human IgG+IgA+IgM (heavy chain and light chain) antibody (KPL) in PBS at 10 µg/mL for 1 h at 37° C., followed by washing three times with washing buffer (0.1% Tween-20 in PBS). Afterwards, the plates were incubated overnight in blocking solution (3% BSA in PBS) at 4° C. The following day, the plates were washed as above, and 50 µL of standard in-house purified human anti-Rhesus (D) antibody and 1:10 diluted supernatants from the transient transfection, all diluted in dilution buffer (1% BSA in PBS), were added in duplicates and incubated for 1 h at 37° C. Following another round of washes, 50 µL of alkaline phosphatase-conjugated anti-human IgG (Fc-specific) antibody (Sigma) were added to each well and incubated for 1 h at 37° C. After another three washes, 50 µL of SIGMA-FAST™ p-Nitrophenyl phosphate substrate were added to each well of the plates and incubated for 15 min at room temperature before the absorbance was read at a wavelength of 405 nm using VersaMax ELISA microplate reader (Molecular Devices). A reference wavelength of 620 nm was used.

Generation of Avastin Heavy Chain Constructs with Hybrid Signal Peptides

Based on the sequence alignment of the 8 IgG heavy chain signal peptides S1-S8, several conserved amino acid residues were observed. The inventors prepared six Avastin heavy chain constructs with hybrid leader peptides, that had one or more amino acid residues mutated from the parental H7, designated H7a-H7f. These were engineered using QuikChange II XL site-directed mutagenesis kit (Agilent), following the manufacturer's protocol.

The primer pairs used to generate each construct from the parental H7 (unless specified) were the following:

H7a, 5'-ccaccatggagtttgggtggagctgggttttcctcg-3' (SEQ ID NO: 31) and 5'-cgaggaaaacccagctccacccaaactccatggtgg-3' (SEQ ID NO: 32);

H7b, 5'-gagtttgggctgagctggctcttcctcgttgctcttttt-3' (SEQ ID NO: 33) and 5'-aaaaagagcaacgaggaaga gccagctcagcccaaactc-3' (SEQ ID NO: 34);

H7c 5'-ctgggttttcctcgttgctgcttttagaggtgtccgtagtgt-3' (SEQ ID NO: 35) and 5'-acactggacacctctaaaa gcagcaacgaggaaaacccag-3' (SEQ ID NO: 36);

H7d, 5'-tttttagaggtgtccagtccgaggttcagctggtggag-3' (SEQ ID NO: 37) and 5'-ctccaccagctgaacctc ggactggacacctctaaaaa-3' (SEQ ID NO: 38);

H7e, 5'-gccaccatggagtttgggtggagctggct cttcctcgttgctgctttt-3' (SEQ ID NO: 39) and 5'-aaaagcagcaac-gaggaagagccagctccacccaaactccatggtggc-3' (SEQ ID NO: 40) using the construct H7c as a template;

H7f, 5'-cttttagaggtgtccagtccgaggttcagctggtggag-3' (SEQ ID NO: 41) and 5'-ctccaccagctgaacctc ggactggacacctctaaaag-3' (SEQ ID NO: 42) by using construct H7e as a template, where the underlined bases are the mutated targets. Subsequently, two batches of the hybrid constructs and one batch of the Avastin light chain construct were prepared using QIAGEN Plasmid Maxi Kit (Qiagen, Basel, Switzerland).

Transient Transfection of the Hybrid Constructs

For each pair of Avastin light and heavy chain constructs, 2 mL of CHO-K1 cells were seeded onto each well of a 6-well plate at a concentration of $3 \times 10^5$ cells per mL. On the following day, transfection was carried out using FuGENE 6 transfection reagent (Roche Applied Science, Rotkreuz, Switzerland) at a reagent:light chain:heavy chain ratio of 6:1:1, following the manufacturer's protocol. Each transfection was performed in duplicate and a third well was transfected with 0.2 µg of GFP construct pmaxGFP® in addition to the Avastin constructs. This served as transfection efficiency control. After 48 h of incubation, the media were collected and centrifuged at 6,000×g for 10 min to remove cell debris, and the supernatant subsequently subjected to ELISA. For the wells transfected with GFP, the cells were trypsinised and subjected to flow cytometry analysis for green fluorescence.

Large Scale Transfection of the Antibody Constructs for Antibody Production and Purification For each of the antibodies, CHO-K1 cells were seeded into ten T-175 flasks and transfected on the following day with the constructs encoding the best signal peptides as determined by the IgG ELISA assay. Six hours after transfection, the cells were washed with DPBS and the medium replaced with chemically defined serum-free medium. Conditioned medium containing the secreted antibody was collected every 2-3 days over the course of 7 days. The antibodies were then purified with fast protein liquid chromatography (FPLC-AKTA purifier) system on a HiTrap Protein A HP column (GE Healthcare), equilibrated with 20 mM, pH 7.0 sodium phosphate buffer.

NanoLC-MS/MS Analysis

Diafiltration cartridges (30 kDa; Millipore, Billerica, Mass.) were used to concentrate 20 µg of each antibody into PBS. Antibodies were then supplemented with 20 mM triethylammonium bicarbonate, pH 8.5, reduced with 30 mM tris(2-carboxyethyl)phosphine (TCEP) at 60° C. for 1 h, and cysteine alkylated with 60 mM iodoacetamide at room temperature in the dark for 40 min. Digestion was carried out using sequencing-grade modified trypsin (1:25) (Promega, Madison, Wis.) overnight at 37° C. Peptide samples were dried down in Savant SpeedVac (Thermo Scientific, Asheville, N.C.), and resuspended with 25 µl buffer A (0.1% formic acid).

Nanoscale liquid chromatography (NanoLC) was performed on nanoACQUITY UPLC System (Waters, Milford, Mass.). Peptide sample (2 µl) was loaded onto Symmetry C18 trapping column, 5 µm, 180 µm×20 mm (Waters) and desalted for 8 min with 2% buffer B (0.1% formic acid in acetonitrile) at 8 µl/min. The trapping column was subsequently switched online to a nanoACQUITY UPLC BEH130 C18 column, 1.7 µm, 75 µm×150 mm (Waters), and the peptides were separated at a flow of 300 nl/min with a gradient consisting of 60 min 2-28% buffer B, 8 min 28-40% buffer B and 5 min 97% buffer B.

Mass spectrometer (MS) detection was performed on a LTQ Orbitrap Velos MS (Thermo Scientific) operating in CID top 10 mode, with nanoelectrospray potential at 1.7 kV. Full scan MS spectra (from m/z 300-1,800) were obtained by data dependent acquisition with the resolution set at 60,000. The 10 most intense peptide ions with charge state ≥2 were sequentially fragmented with normalised collision energy of 35 V. Minimum signal threshold for MS/MS was set at 500 counts, activation q value at 0.25 and activation time at 10 ms. Ion trap and orbitrap maximal injection times were set to 100 ms and 10 ms respectively.

Raw data files were processed by version 1.3.0.339 of Proteome Discoverer (Thermo Scientific) using SEQUEST algorithm, and searched against respective compiled databases consisting of sequentially shortened antibody sequences from the N-terminal.

Evaluation of Human Immunoglobulin Signal Peptides for Antibody Secretion in CHO Cells Sequences of human Ig heavy chains and kappa chains with complete coding regions were collected from the PubMed database. In total, 173 human Ig heavy chains and 62 human kappa chains were gathered. Majority of the heavy chain signal peptides contain 19 amino acids and all of the kappa light chain signal peptides contain 22 amino acids. A database of signal peptide sequences was built using these heavy chains and light chains. The signal peptides were then clustered according to sequence similarity and the phylogenetic tree is shown in FIG. 1. Based on the phylogenetic tree, eight heavy chain signal peptides (H1-H8) and two kappa light chain signal peptides (L1 and L2) were selected. The amino acid sequences and the DNA sequences of these selected signal peptides are shown in the table in FIG. 2. These signal peptides were then assessed for their impact on antibody secretion in CHO-K1 cells.

The variable regions and the constant regions of the heavy chain and light chain of Herceptin, Avastin, Remicade, Rituxan and Humira were generated based on publicly available information. Each antibody heavy chain was then fused to any one of the eight signal peptides (H1-H8) to generate eight different heavy chain constructs. Each antibody light chain was fused to two signal peptides (L1 & L2) to generate two different light chain constructs (Table in FIG. 2).

For analyzing the impact of signal peptides on the secretion of each antibody, 16 heavy and light chain combinations were transfected into CHO-K1 cells. Duplicate transfections for each pair of heavy and light chain were performed. To normalize transfection efficiency, a third transfection was also performed. In this transfection, in addition to the same pair of heavy and light chain constructs, a construct expressing GFP was also included in the transfection as the control for transfection efficiency as known in the art. The antibody concentrations were determined 2 days after transfection by ELISA. The FIGS. 3 to 8 (A and C) show the raw data of the ELISA and the expression level of GFP. The Figures labeled A and C assessed the secretion efficiency of L1 and L2 light chain respectively. Within each box, the secretion efficiency of the H1 to H8 was compared. GFP fluorescence was also assessed in each of the samples as a control for transfection efficiency.

Taking the heavy chain signal peptide 1 (H1) as a reference as explained above, the relative productivity of each antibody was plotted and shown in FIGS. 3 to 8 (B and D). As clearly shown, the amount of the antibody in the media is highly dependent on the signal peptide used. Interestingly, the heavy chain signal peptide 7 (H7) resulted in a significantly increased secretion for Avastin, Remicade, Rituxan and Humira. This observation was seen with the use of both light chain signal peptides L1 and L2. For Herceptin, the light chain signal peptide factored in more significantly with respect to increasing the titre of the antibody. The inventors discovered that several combinations of heavy chain/light chain signal peptides lead to increased secretion of the Herceptin antibody, namely H4/L1, H5/L1, H8/L1, H1/L2 and H7/L2.

Figure 6:
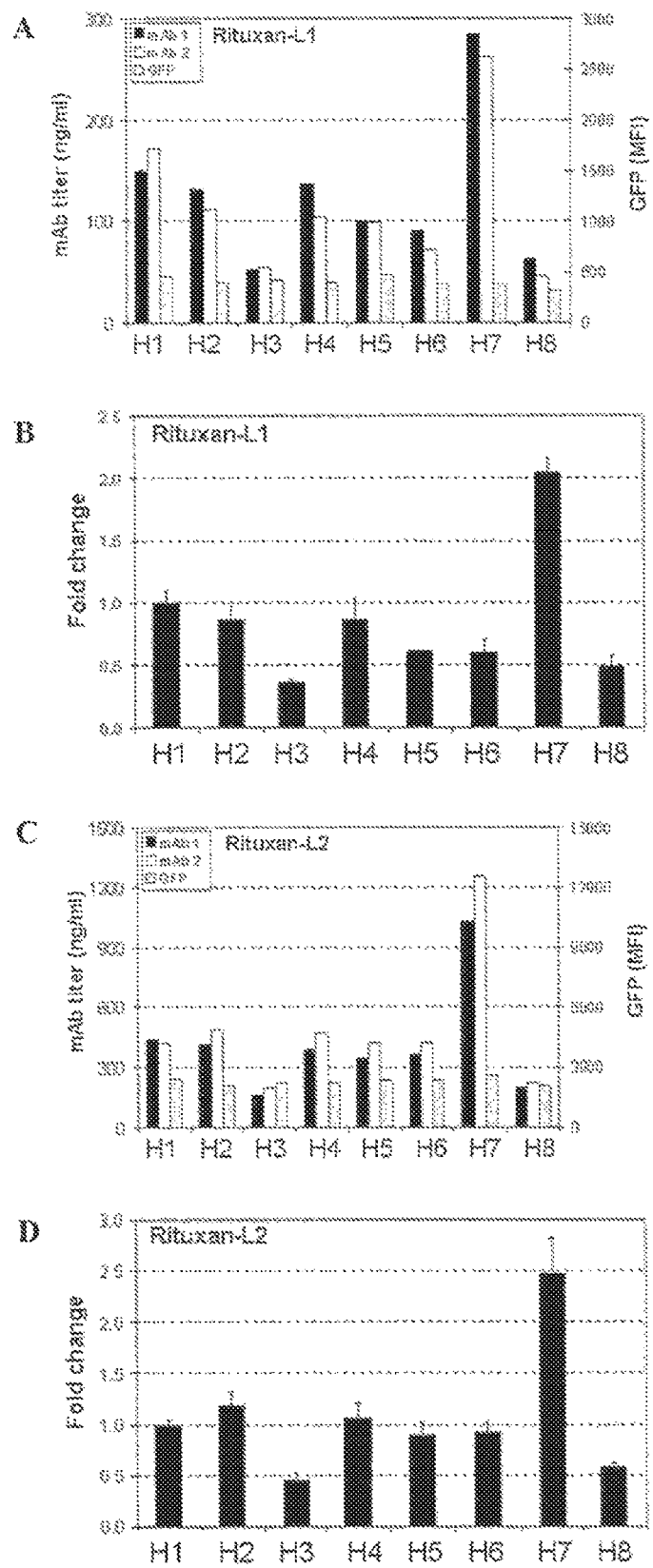
FIG. 6 is a series of histogram plots showing the amount of Rituxan heavy chain produced when different signal peptides were used as indicated above. A and C: ELISA results. Bottom panel: relative productivity normalized to H1.
Figure 7:
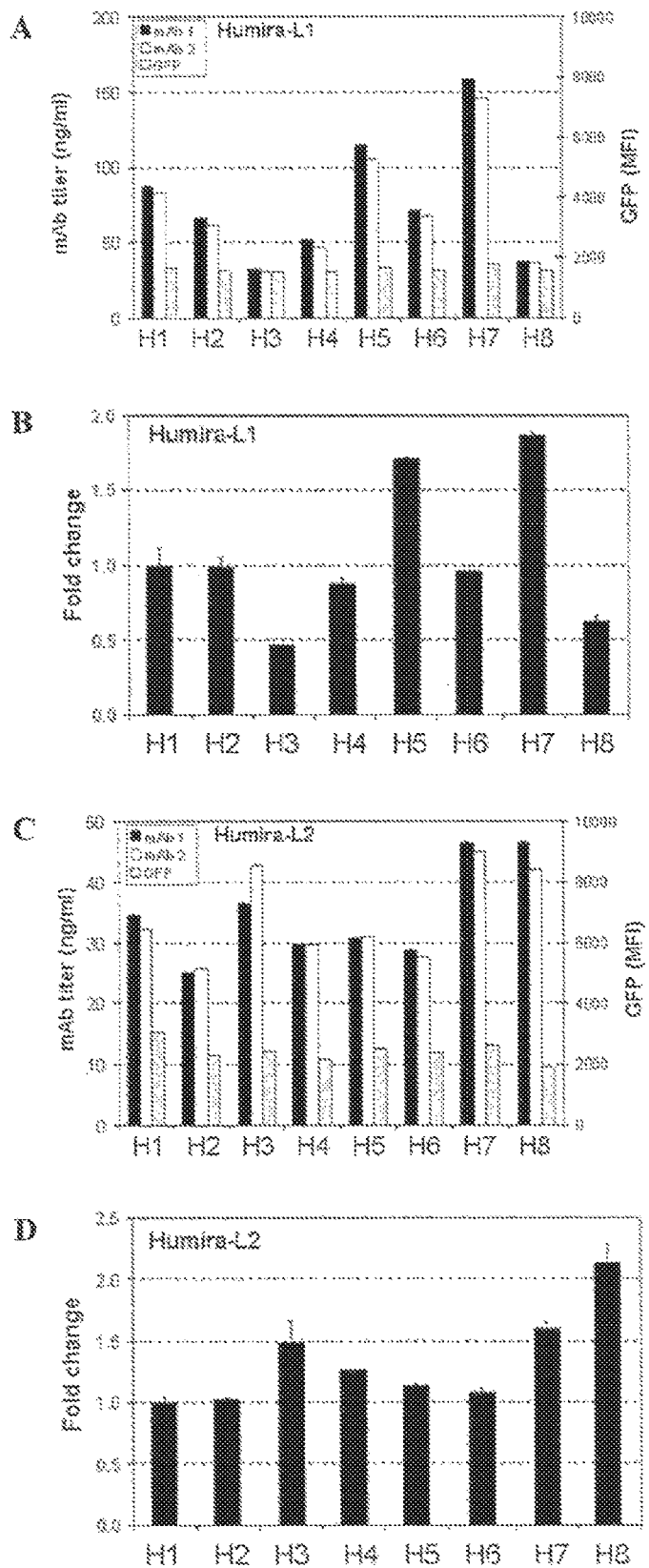
FIG. 7 is a series of histogram plots showing the amount of Humira heavy chain produced when different signal peptides were used.

However, the impact of the light chain signal peptides (L1 & L2) could not be conclusively determined in FIG. 6 A to D. As shown in FIGS. 6 A and C, the amount of Rituxan antibody produced by H7/L1 was significantly different from that produced by H7/L2. The GFP levels between these two sets of transfection were also very different, suggesting differences in transfection efficiencies. To further confirm these results, combinations of signal peptide H7 with either L1 or L2 were tested for their impacts on the production of Avastin, Remicade and Rituxan, in one single experiment. The signal peptides H1, H5 and H7 in combination with L1 or L2, were assessed for the ability to increase production of Herceptin.

Figure 8:
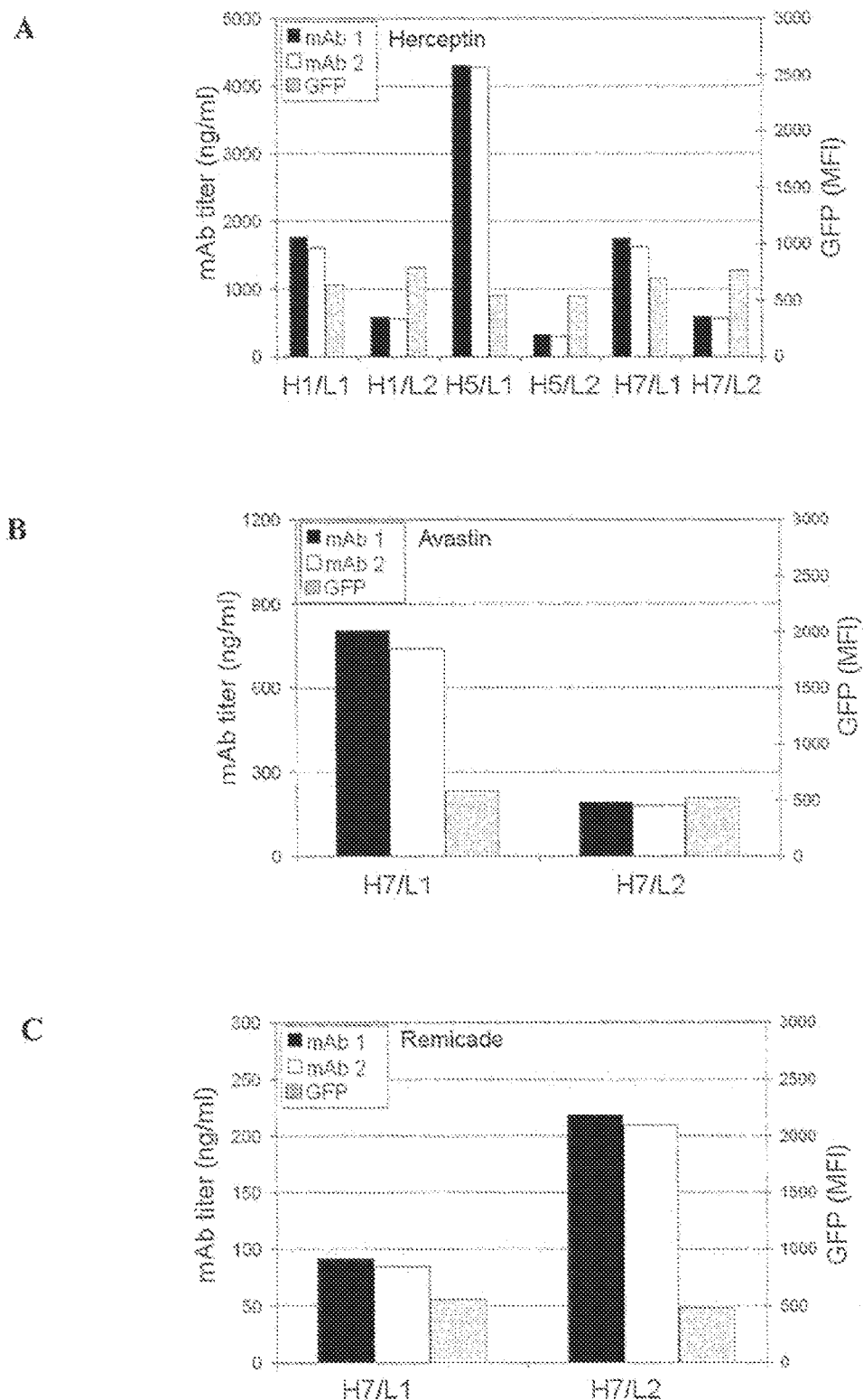
FIG. 8 is a series of histogram plots comparing the efficiency of secretions according to the light chain L1 or L2 that was used, for each of the indicated five therapeutic antibodies. Based on the results obtained in FIGS. 3 to 7, the heavy chain of the antibody of interest with a heavy chain signal peptide combination with the highest secretion was selected. The selected construct was co-expressed in CHO cells with the light chain signal peptide L1 or L2 fused with the light chain of said antibody of interest. The titers of the produced antibody were measured by IgG ELISA and the values thus obtained compared. The comparison allows the selection of the pair of heavy chain/signal peptide and corresponding light chain/signal peptide that gives the best production/secretion for the antibody of interest.
Figure 8:
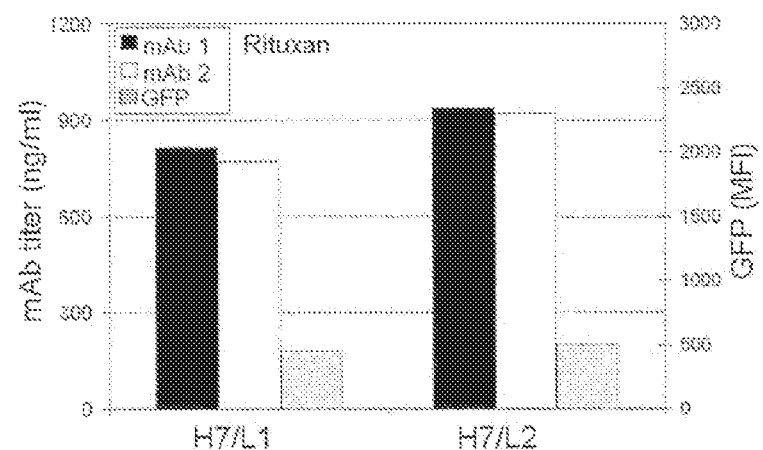
Figure 8:
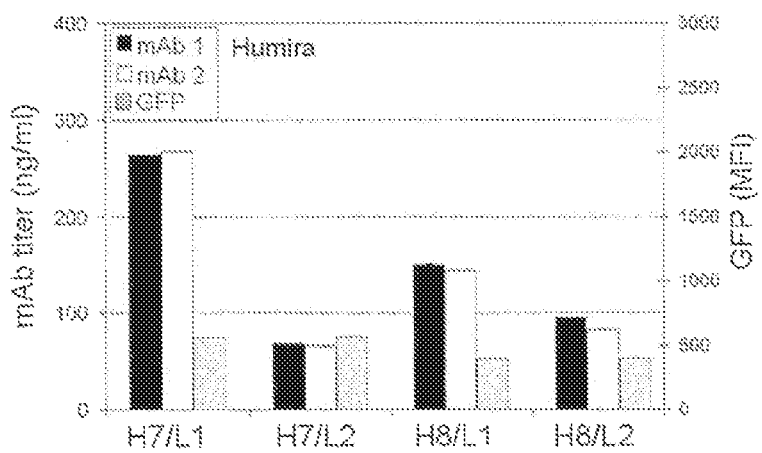

The results in FIG. 8 correlate well with that of FIG. 6 which allowed the inventors to identify the ideal signal peptide combinations for increased production of specific antibodies. The signal peptide combination for Herceptin, Avastin, Remicade, Rituxan and Humira were H5/L1, H7/L1, H7/L2, H7/L2 and H7/L1 respectively. Based on the results of the transient transfection of these antibodies in the CHO cell expression system, it was determined that Herceptin is produced most efficiently, followed by Rituxan, Avastin, Humira, and lastly Remicade.

Assessing the Impact of the Optimized Rituxan Signal Peptides Against the Original Peptides Among the five antibodies, Rituxan is the only antibody for which heavy and light chain signal peptide sequence information is available in public database. However, the availability of the information does not entail that the original signal peptides are optimal for the secretion of the antibody in CHO cells. Rituxan's original light chain signal peptide is MDFQVQIISFLLISASVIMSRG (SEQ ID NO: 317), while the original heavy chain signal peptide is MGWSLILLFLVAVATRVLS (SEQ ID NO: 318). As indicated above, the H7/L2 is the optimal signal peptides combination for Rituxan (FIG. 8D). In order to compare the effects of the original signal peptide with the optimized peptides, the original heavy and light chain signal peptides were fused to Rituxan and transfected into CHO-K1 cells. As a control, Rituxan H1/L2 constructs were also transfected into CHO-K1 cells. Two days after transfection, conditioned media was harvested and the titre of Rituxan heavy chain was determined with ELISA. The results in FIG. 4 showed that the optimized signal peptides (H7/L2) resulted in more than a two-fold increase in antibody titre compared to the original signal peptides.

Sequence Comparisons of the Eight Ig Heavy Chain Signal Peptides

Three domains were defined in the signal peptides, the positively charged N-terminal domain (N-domain), the hydrophobic domain (H-domain) and the polar C-terminal domain (C-domain). The eight heavy chain signal peptides identified in this study show certain common features and yet each of them is quite different from others. As the sequence alignment shown in FIG. 10A, all the signal peptides contain 19 amino acids except for H8, which contains 26. In all the signal peptides except for H3, the amino acid that follows the translation starting methionine (M) is a negatively charged glutamic acid or aspartic acid (E or D), however, it is a lysine (K) at the same position in H3. In fact, in almost all of Ig heavy chains in our database, the second amino acid is either E or D. The second amino acid is a K in almost all signal peptides in cluster 3 represented by H3 (FIG. 1C, bottom panel). Amino acids 7 to 14 form the hydrophobic H-domain and amino acids 15 to 19 form the C-domain. Four signal peptides (H1, H2, H6, H7) terminate with a cysteine (C), whereas others terminate with a serine (S). There is only one negatively charged amino acid (E), and no positively charged amino acid; in the N-domains of the signal peptide clusters 1, 6 and 7 (represented by H1, H6 and H7). Therefore, not all N-domains of the signal peptides are positively charged.

Characterization of the Optimal Signal Peptide for Avastin (H7)

As discussed above, H7 is shown to be the most optimal signal peptide for the heavy chains in 4 out of 5 antibodies studied. Avastin was used as the model molecule to further optimize the amino acid sequence of H7. A sequence comparison of all signal peptides used in the present invention (H1-H8) showed several highly conserved amino acids: M*W/LLFLVAAGVQS/C (SEQ ID NO: 319). (FIG. 10A). The alignment of this highly conserved sequence with H7 (MEFGLSWVFLVALFRGVQC: SEQ ID NO: 3), revealed that three amino acid residues in H7 (underlined) were divergent from the highly conserved sequence. To investigate the functional significance of these amino acids, three H7 mutants were generated by individually mutating each of the amino acids. As shown in FIG. 10B, H7a carries a L5W mutation, H7b carries a V8L mutation and H7c carries a L13A mutation. To compare the difference between C and S at the cleavage site, we generated H7d which carries a C19S mutation. In H7e, all three amino acids in H7 were mutated to investigate the combinatory effect of these three amino acids. In H7f, four amino acids were mutated, including a C to S mutation (FIG. 10**B).

These mutated signal peptides fused to the Avastin heavy chains were co-transfected with L1 Avastin light chain into CHO-K1 cells. Two days after transfection, the amount of antibody in each conditioned medium was determined by ELISA. Interestingly, the results show that the substitution of any of the three amino acids (H7a, H7b and H7c) dramatically reduced the amount of Avastin heavy chain secreted into the medium (FIG. 10C), suggesting that each of these three amino acids on H7 is important for its function as a signal peptide H7 for Avastin. This is despite the fact that these 3 amino acids were highly conserved in many heavy chain signal peptides. Substituting all three amino acids together (H7e and H7f) further reduced the secretion of Avastin. In contrast, substitution of cysteine to serine (H7d) at the cleavage site does not affect the secretion of the antibody, suggesting that both amino acids are equally effective at the cleavage site.

Analysis of Antibody Heterogeneity Due to N-Terminal Processing and Cleavage of the Signal Peptides In addition to improving secretion efficiency, the inventors also provided some surprising results in view of cleavage heterogeneity problem which occurs as a result of non-specific cleavage of the signal peptide by SPP. This phenomenon leads to the elongation or truncation of the N-terminus of the heavy and light chains which can have a direct effect on the antigen recognition site of the antibody. Such antibodies with variable heterogeneities may not be suitable for biopharmaceutical therapeutics. To determine whether the best signal peptides presently identified can be cleaved efficiently at their expected sites, large scale transfections of each recombinant antibody were performed. Antibodies were harvested from the conditioned media and purified by protein A affinity chromatography. Purified antibodies were subsequently digested by trypsin, and the resultant peptides analysed by mass spectrometry.

Detection of alternative cleavage sites of the N-terminal peptides of both heavy and light chains of each antibody were carried out by tryptic peptide mapping using LC-MS/MS. N-terminal peptides were identified by high-resolution tandem mass spectrometry (MS/MS), and corresponding peptide precursor peak areas from extracted ion chromatograms (XICs) were used for relative quantification.

The results obtained for Avastin showed that the correct heavy chain N-terminal peptide EVQLVESGGGLVQPGG-SLR (m/z 941.51) accounted for 99.4% of total heavy chain N-terminal peptides detected, while an erroneously processed peptide ESGGGLVQPGGSLR (m/z 657.35), cleaved 5 residues downstream of the expected cleavage site, accounted for 0.6% (FIGS. 11A & B). For the light chain, only the correctly processed N-terminal peptide DIQMTQSPSSLSASVGDR (m/z of 939.95) was detected (FIG. 11C), thus suggesting the absence of alternative cleavage site in signal peptide processing. N-terminal peptides from all antibodies were similarly identified and quantified in triplicate mass spectrometry analyses. The results are summarized in Table 2 below and the detailed breakdown is shown in Table 3. As depicted, the optimized signal sequences used in the expression of the antibodies did not give rise to significant cleavage heterogeneity of the signal peptides. Efficacy of N-terminal processing at the expected cleavage site ranged from ~99.2% to 100%, while N-terminal peptides resulting from erroneous cleavage, when present and summed, accounted for less than 1% of total N-terminal peptide population.

TABLE 2

Proportion of N-terminal peptide(s) quantified by triplicate analyses using mass spectrometry.

| Antibody | Sequence (N-terminal) | Percentage (%) |
|---|---|---|
| Avastin - LC | ...RC▼DIQMTQSPSSLSASVGDR (SEQ ID NO: 320) | 100.00 |
| Avastin - HC | ...QC▼EVQLVESGGGLVQPGGSLR (SEQ ID NO: 321) | 99.38 |
|  | ...QCEVQLV▼ESGGGLVQPGGSLR (SEQ ID NO: 321) | 0.62 |
| Herceptin - LC | ...RC▼DIQMTQSPSSLSASVGDR (SEQ ID NO: 322) | 99.18 |
|  | ...RCDIQMTQ▼SPSSLSASVGDR (SEQ ID NO: 322) | 0.71 |
|  | ...RCDIQMTQSP▼SSLSASVGDR (SEQ ID NO: 322) | 0.11 |
| Herceptin - HC | ...QS▼EVQLVESGGGLVQPGGSLR (SEQ ID NO: 323) | 99.91 |
|  | ...QSEVQ▼LV▼ES▼GG▼GLVQPGGSLR (SEQ ID NO: 323) | 0.09 |
| Humira - LC | ...RC▼DIQMTQSPSSLSASVGDR (SEQ ID NO: 324) | 100.00 |
| Humira - HC | ...QC▼EVQLVESGGGLVQPGR (SEQ ID NO: 325) | 100.00 |
| Rituxan - LC | ...RC▼QIVLSQSPAILSASPGEK (SEQ ID NO: 326) | 98.95 |
|  | ...RCQIVL▼SQSPAILSASPGEK (SEQ ID NO: 326) | 0.90 |
|  | ...RCQIVLSQ▼SP▼AILSASPGEK (SEQ ID NO: 326) | 0.15 |
| Rituxan - HC | ...QC▼QVQLQQPGAELVKPGASVK (SEQ ID NO: 327) | 99.82 |
|  | ...QCQVQ▼L▼QQP▼G▼A▼ELVKPGASVK (SEQ ID NO: 327) | 0.18 |
| Rituxan_k01 - LC | ...MA▼QIVLSQSPAILSASPGEK (SEQ ID NO: 328) | 99.81 |
|  | ...MAQ▼I▼VLSQSPAI▼LSASPGEK (SEQ ID NO: 328) | 0.19 |
| Rituxan_k01 - HC | ...LS▼QVQLQQPGAELVKPGASVK (SEQ ID NO: 329) | 99.62 |
|  | ...LSQVQL▼QQ▼PGAELVKPGASVK (SEQ ID NO: 329) | 0.38 |
| Remicade - LC | ...RC▼DILLTQSPAILSVSPGER (SEQ ID NO: 330) | 100.00 |
| Remicade - HC | ...QC▼EVK↓LEESGGGLVQPGGSMK (SEQ ID NO: 331) | *100.00 |

The translocation of secretory proteins into the lumen of the ER represents a rate limiting step within the classical secretory pathway. Several studies have shown that protein production can be enhanced through the use of alternative signal peptides. This work is the first systematic analysis for identifying the best signal peptides for recombinant antibody production. Advantageously, the strategy for selecting optimal signal peptides begins by generating a database of known antibody signal peptides of human Ig heavy chains and kappa light chains from complete cDNA sequences in the public database. The present exemplary signal peptides collected in the database described herein are only signal peptides of human origin, partly due to the fact that majority of antibody drugs are now either humanized or fully human antibodies.

TABLE 3

Proportion of N-terminal peptide(s) quantified by triplicate analyses using mass spectrometry (detailed breakdown).

| Antibody | Sequence (N-terminal) | Proportion (%) 1 | 2 | 3 | Average (%) |
|---|---|---|---|---|---|
| Avastin-LC | . . . RC▼DIQMTQSPSSLSASVGDR (SEQ ID NO: 320) | 100.00 | 100.00 | 100.00 | 100.00 |
| Avastin-HC | . . . QC▼EVQLVESGGGLVQPGGSLR (SEQ ID NO: 321) | 99.41 | 99.29 | 99.43 | 99.38 |
| | . . . QCEVQLV▼ESGGGLVQPGGSLR (SEQ ID NO: 321) | 0.59 | 0.71 | 0.57 | 0.62 |
| Herceptin-LC | . . . RC▼DIQMTQSPSSLSASVGDR (SEQ ID NO: 322) | 99.16 | 99.34 | 99.06 | 99.18 |
| | . . . RC DIQMTQ▼SPSS LSASVGDR (SEQ ID NO: 322) | 0.68 | 0.59 | 0.84 | 0.71 |
| | ...RC DIQMTQSP▼SSLSASVGDR (SEQ ID NO: 322) | 0.16 | 0.07 | 0.10 | 0.11 |
| Herceptin-HC | . . . QS▼EVQLVESGGGLVQPGGSLR (SEQ ID NO: 323) | 99.91 | 99.92 | 99.90 | 99.91 |
| | . . . QS EVQ▼LVESGGGLVQPGGSLR (SEQ ID NO: 323) | 0.02 | 0.02 | 0.02 | 0.02 |
| | . . . QS EVQLV▼ESGGGLVQPGGSLR (SEQ ID NO: 323) | 0.03 | 0.02 | 0.03 | 0.03 |
| | . . . QS EVQLVES▼GGGLVQPGGSLR (SEQ ID NO: 323) | 0.03 | 0.02 | 0.04 | 0.03 |
| | . . . QS EVQLVESGG▼GLVQPGGSLR (SEQ ID NO: 323) | 0.01 | 0.02 | 0.01 | 0.01 |
| Humira-LC | . . . RC▼DIQMTQSPSSLSASVGDR (SEQ ID NO: 324) | 100.00 | 100.00 | 100.00 | 100.00 |
| Humira-HC | . . . QC▼EVQLVESGGGLVQPGR (SEQ ID NO: 325) | 100.00 | 100.00 | 100.00 | 100.00 |
| Rituxan-LC | . . . RC▼IVLSQSPAILSASPGEK (SEQ ID NO: 326) | 98.86 | 99.09 | 98.89 | 98.95 |
| | . . . RC QIVL▼SQSPAILSASPGEK (SEQ ID NO: 326) | 0.96 | 0.77 | 0.96 | 0.90 |
| | (SEQ ID NO: 326) | 0.10 | 0.08 | 0.09 | 0.09 |
| | . . . RC QIVLSQ▼SPAILSASPGEK (SEQ ID NO: 326) | 0.08 | 0.05 | 0.05 | 0.06 |
| | . . . RC QIVLSQSP▼AILSASPGEK (SEQ ID NO: 326) | 99.80 | 99.84 | 99.81 | 99.82 |
| Rituxan-HC | QC▼QVQLQQPGAELKPGASVK (SEQ ID NO: NO: 327) | 0.00 | 0.00 | 0.01 | 0.00 |
| | . . . QC QVQL▼QQPGAELVKPGASVK (SEQ ID NO: NO: 327) | 0.02 | 0.02 | 0.02 | 0.02 |
| | . . . QC QVQL▼QQPGAELVKPGASVK (SEQ ID NO: NO: 327) | 0.01 | 0.00 | 0.00 | 0.01 |
| | . . . QC QVQLQQP▼GAELVKPGASVK (SEQ ID NO: NO: 327) | 0.01 | 0.00 | 0.00 | 0.00 |
| | . . . QC QVQLQQPG▼AELVKPGASVK (SEQ ID NO: NO: 327) | 0.16 | 0.14 | 0.15 | 0.15 |
| | . . . QC QVQLQQPGA▼ELVKPGASVK (SEQ ID NO: NO: 327) | | | | |
| Rituxan_k01-LC | . . . MA▼QIVLSQSPAILSASPGEK (SEQ ID NO: 328) | 99.94 | 99.74 | 99.74 | 99.81 |
| | . . . MA Q▼IVLSQSPAILSASPGEK (SEQ ID NO: 328) | 0.03 | 0.02 | 0.11 | 0.05 |
| | . . . MA QI▼VLSQSPAILSASPGEK (SEQ ID NO: 328) | 0.01 | 0.05 | 0.14 | 0.07 |
| | . . . MA QIVLSQSPAI▼LSASPGEK (SEQ ID NO: 328) | 0.01 | 0.19 | 0.01 | 0.07 |

TABLE 3-continued

Proportion of N-terminal peptide(s) quantified by triplicate analyses using mass spectrometry (detailed breakdown).

| Antibody | Sequence (N-terminal) | Proportion (%) | | | Average (%) |
|---|---|---|---|---|---|
| | | 1 | 2 | 3 | |
| Rituxan_k01-HC | ...LS▼QVQLQQPGAELVKPGASVK (SEQ ID NO: 329) | 99.53 | 99.71 | 9.61 | 99.62 |
| | ...LS QVQL∇QQPGAELVKPGASVK (SEQ ID NO: 329) | 0.38 | 0.25 | 0.27 | 0.30 |
| | ...LS QVQLQQ∇PGAELVKPGASVK (SEQ ID NO: 329) | 0.09 | 0.05 | 0.13 | 0.09 |
| Remicade-LC | ...RC▼DILLTQSPAILSVSPGER (SEQ ID NO: 330) | 100.00 | 92.87 | 95.91 | } 100.00 |
| | ...RC▼DILLTQSPAILSVSPGERVSFSCR (SEQ ID NO: 330) | absent | 7.13 | 4.09 | |
| Remicade-HC | ...QC▼EVKLEESGGGLVQPGGSMK (SEQ ID NO: 331) | 2.13 | 100.00 | 100.00 | } *100.00 |
| | ...QC EVK↓LEESGGGLVQPGGSMK (SEQ ID NO: 331) | 97.87 | absent | absent | |

Light chain (LC); heavy chain (HC); signal peptide processing site: actual N-terminal (▼); erroneous N-terminal (∇); tryptic site (↓). Signal peptide sequences are depicted in smaller font size.
*The presence of a trypic site near the N-terminal of Remicade-HC required reliance on an N-terminal peptide with one missed cleavage for identification and quantification. As such, estimation of the proportion of N-terminal peptides is likely to be unreliable, as the majority of the N-terminal peptides would have been processed at the tryptic site, leading to difficulties in identifying any erroneous N-terminal peptides that, if present, would have been at low concentrations to begin with. Note that Remicade sample-1 was digested under normal conditions as decribed while sample-2 and -3 were digested under conditions that favoured partial digestion (at pH 7.4, room temperature for 4 hr).

Based on sequence similarities, eight heavy chain and two light chain signal peptides were fused to each of the five antibodies for secretion efficiency analysis. Our results showed that some antibodies can tolerate different signal peptides, whereas others are more restricted. The best signal peptide combination identified for Herceptin, Avastin, Remicade, Rituxan, and Humira were H5/L1, H7/L1, H7/L2, H7/L2, and H7/L1, respectively. In the case of Avastin, Remicade and Rituxan, the impacts of heavy chain signal peptides on the production of these antibodies showed similar patterns, with H7 being the most optimal signal peptide (FIG. 2). For some antibodies such as Herceptin, Avastin and Humira, the antibody productivity was higher when the L1 light chain was produced, whereas for others (Rituxan and Remicade), the L2 light chain resulted in higher productivity of the antibody (FIG. 3 to 10), suggesting that, when used in combination the light chain signal peptide also affects the overall productivity of the antibody.

As Rituxan is the only antibody with its heavy and light chain signal peptide information available in public database, the secretion efficiency of its native mouse signal peptides was compared with that of human signal peptides and the result showed that the latter improved the production of a chimeric Rituxan by a factor of 2. Advantageously, the method for signal peptide optimization, as disclosed herein, may improve the production of recombinant antibodies.

In summary, the inventors identified the best signal peptide pairs for each of five therapeutic antibody drugs from a collective pool of 230 human IgG signal peptides. Additionally, the method of the invention may be used to identify the best signal peptides for producing new antibody drugs.

The invention claimed is:

1. An optimized heavy chain signal peptide and light chain signal peptide for a recombinant antibody, wherein said recombinant antibody is selected from the group consisting of trastuzumab (Herceptin, CAS number 180288-69-1), bevacizumab (Avastin, CAS number 216974-75-3), infliximab (Remicade, CAS number 170277-31-3), rituximab (Rituxan, CAS number 174722-31-7) and adalimumab (Humira, CAS number 331731-18-1); wherein a C-terminal end of said heavy chain signal peptide is fused to a heavy chain of said recombinant antibody, wherein said heavy chain signal peptide comprises an amino acid sequence selected from the group consisting of MELGLSWIFLLAILKGVQC (H1, SEQ ID NO: 5), MELGLRWVFLVAILEGVQC (H2, SEQ ID NO: 6), MDWTWRFLFVVAAATGVQS (H5, SEQ ID NO: 1), MEFGLSWLFLVAILKGVQC (H6, SEQ ID NO: 9), MEFGLSWVFLVALFRGVQC (H7, SEQ ID NO: 3) and MDLLHKNMKHLWFFLLLVAAPRWVLS (H8, SEQ ID NO: 10); and wherein a C-terminal end of said light chain signal peptide is fused to a light chain of the recombinant antibody, wherein the N-terminus of said light chain signal peptide comprises an amino acid sequence selected from the group consisting of MDMRVP (SEQ ID NO: 311) and MKYLLP (SEQ ID NO: 312).

2. The optimized heavy chain signal peptide and light chain signal peptide for recombinant antibody according to claim 1, wherein the C-terminus of said light chain signal peptide comprises SGARC (SEQ ID NO: 313) or QPAMA (SEQ ID NO: 314).

3. The optimized heavy chain signal peptide and light chain signal peptide for recombinant antibody of claim 1, wherein the heavy chain signal peptide comprises an amino acid sequence of SEQ ID NO: 1, and wherein the recombinant antibody is trastuzumab (Herceptin, CAS number 180288-69-1).

4. The optimized heavy chain signal peptide and light chain signal peptide for recombinant antibody of claim 1, wherein the heavy chain signal peptide comprises an amino acid sequence of SEQ ID NO: 3, and wherein the recombinant antibody is bevacizumab (Avastin, CAS number 216974-75-3).

5. The optimized heavy chain signal peptide and light chain signal peptide for recombinant antibody of claim 1, wherein the heavy chain signal peptide comprises an amino acid sequence of SEQ ID NO: 3, and wherein the recombinant antibody is infliximab (Remicade, CAS number 170277-31-3).

6. The optimized heavy chain signal peptide and light chain signal peptide for recombinant antibody of claim 1, wherein the heavy chain signal peptide comprises an amino acid sequence of SEQ ID NO: 3, and wherein the recombinant antibody is rituximab (Rituxan, CAS number 174722-31-7).

7. The optimized heavy chain signal peptide and light chain signal peptide for recombinant antibody of claim 1, wherein the heavy chain signal peptide comprises an amino acid sequence of SEQ ID NO: 3, and wherein the recombinant antibody is adalimumab (Humira, CAS number 331731-18-1).

8. The optimized heavy chain signal peptide and light chain signal peptide for recombinant antibody of claim 1, wherein the light chain signal peptide comprises an amino acid sequence selected from the group consisting of SEQ ID NO: 2 and SEQ ID NO: 4.

9. The optimized heavy chain signal peptide and light chain signal peptide for recombinant antibody of claim 8, wherein the light chain signal peptide comprises an amino acid sequence of SEQ ID NO: 2, and wherein the antibody of interest is adalimumab (Humira, CAS number 331731-18-1).

10. A polynucleotide sequence encoding the optimized heavy chain signal peptide and light chain signal peptide for recombinant antibody of claim 1.

11. An amino acid sequence comprising
a) the amino acid sequence for trastuzumab (Herceptin, CAS number 180288-69-1);
b) a heavy chain signal peptide of SEQ ID NO: 1, wherein a C-terminal end of said heavy chain signal peptide is fused to the heavy chain amino acid sequence of trastuzumab; and
c) a light chain signal peptide of SEQ ID NO: 2, wherein a C-terminal end of said light chain signal peptide is fused to the light chain amino acid sequence of trastuzumab.

12. A polynucleotide sequence encoding the amino acid sequence according to claim 11.

13. An amino acid sequence comprising
a) the amino acid sequence for bevacizumab (Avastin, CAS number 216974-75-3);
b) a heavy chain signal peptide of SEQ ID NO: 3, wherein a C-terminal end of said heavy chain signal peptide is fused to the heavy chain amino acid sequence of bevacizumab; and
c) a light chain signal peptide of SEQ ID NO: 2, wherein a C-terminal end of said light chain signal peptide is fused to the light chain amino acid sequence of bevacizumab.

14. An amino acid sequence comprising
a) the amino acid sequence for infliximab (Remicade, CAS number 170277-31-3);
b) a heavy chain signal peptide of SEQ ID NO: 3, wherein a C-terminal end of said heavy chain signal peptide is fused to the heavy chain amino acid sequence of infliximab; and
c) a light chain signal peptide of SEQ ID NO: 4, wherein a C-terminal end of said light chain signal peptide is fused to the light chain amino acid sequence of infliximab.

15. An amino acid sequence comprising
a) the amino acid sequence for rituximab (Rituxan, CAS number 174722-31-7);
b) a heavy chain signal peptide of SEQ ID NO: 3, wherein a C-terminal end of said heavy chain signal peptide is fused to the heavy chain amino acid sequence of rituximab; and c) a light chain signal peptide of SEQ ID NO: 4, wherein a C-terminal end of said light chain signal peptide is fused to the light chain amino acid sequence of rituximab.

16. An amino acid sequence comprising
a) the amino acid sequence for adalimumab (Humira, CAS number 331731-18-1);
b) a heavy chain signal peptide of SEQ ID NO: 3, wherein a C-terminal end of said heavy chain signal peptide is fused to the heavy chain amino acid sequence of adalimumab; and
c) a light chain signal peptide of SEQ ID NO: 2, wherein a C-terminal end of said light chain signal peptide is fused to the light chain amino acid sequence of adalimumab.

* * * * *